(12) United States Patent
Hooker et al.

(10) Patent No.: US 11,890,356 B2
(45) Date of Patent: *Feb. 6, 2024

(54) HDAC6 INHIBITORS AND IMAGING AGENTS

(71) Applicant: The General Hospital Corporation, Boston, MA (US)

(72) Inventors: Jacob Hooker, Belmont, MA (US); Changning Wang, Melrose, MA (US); Martin Georg Strebl-Bantillo, Somerville, MA (US); Johanna Kaarina Rokka, Boston, MA (US)

(73) Assignee: The General Hospital Corporation, Boston, MA (US)

(*) Notice: Subject to any disclaimer, the term of this patent is extended or adjusted under 35 U.S.C. 154(b) by 89 days.

This patent is subject to a terminal disclaimer.

(21) Appl. No.: 17/455,170

(22) Filed: Nov. 16, 2021

(65) Prior Publication Data

US 2022/0133916 A1 May 5, 2022

Related U.S. Application Data

(63) Continuation of application No. 16/603,746, filed as application No. PCT/US2018/027077 on Apr. 11, 2018, now Pat. No. 11,207,431.

(60) Provisional application No. 62/484,207, filed on Apr. 11, 2017.

(51) Int. Cl.
*A61K 51/04* (2006.01)
*C07C 259/10* (2006.01)

(52) U.S. Cl.
CPC ............ *A61K 51/04* (2013.01); *C07C 259/10* (2013.01); *C07B 2200/05* (2013.01); *C07C 2602/42* (2017.05); *C07C 2603/74* (2017.05)

(58) Field of Classification Search
CPC .. A61K 51/04; C07C 259/10; C07C 2602/42; C07C 2603/74; C07B 2200/05
USPC ........................................................ 424/1.89
See application file for complete search history.

(56) References Cited

U.S. PATENT DOCUMENTS

| | | | |
|---|---|---|---|
| 4,205,085 | A | 5/1980 | Shepherd |
| 11,207,431 | B2 * | 12/2021 | Hooker ................ C07D 213/79 |
| 2006/0052599 | A1 | 3/2006 | Ishibashi et al. |
| 2011/0212969 | A1 | 9/2011 | Blackburn et al. |
| 2014/0128408 | A1 | 5/2014 | Kozikowski et al. |
| 2015/0359794 | A1 | 12/2015 | Benz et al. |
| 2016/0271276 | A1 | 9/2016 | Hooker et al. |

FOREIGN PATENT DOCUMENTS

| | | |
|---|---|---|
| JP | 2013-542994 | 11/2013 |
| WO | WO 2010/043953 | 4/2010 |
| WO | WO 2011/058582 | 5/2011 |
| WO | WO 2012/068109 | 5/2012 |
| WO | WO 2013/059582 | 4/2013 |
| WO | WO 2014/059306 | 4/2014 |
| WO | WO 2015/058106 | 4/2015 |
| WO | WO 2016/018795 | 2/2016 |

OTHER PUBLICATIONS

Strebl et al. ACS Chem. Neurosci. 2015, supporting information, 1-40. (Year: 2015).*
Perekalin et al. Eur. J. Inorg. Chem. 2013, 481-492. (Year: 2013).*
Neumann et al. Nature 2016, 369-373. (Year: 2016).*
Neumann et al. Nature 2016, supporting information, 1-225. (Year: 2016).*
Konovalov et al. Chem. Commun. 2015, 51, 13527-13530. (Year: 2015).*
Amengual et al., "Dual Targeting of Protein Degradation Pathways with the Selective HDAC6 Inhibitor ACY-1215 and Bortezomib Is Synergistic in Lymphoma," Clinical Cancer Research, 2015, 21(20):4663-4675.
Anderson et al, "Quantification of histone deacetylase isoforms in human frontal cortex, human retina, and mouse brain," PLOS ONE, 2015, 10(5):e0126592.
Auzzas et al., "Non-Natural Macrocyclic Inhibitors of Histone Deacetylases: Design, Synthesis, and Activity," J. Med. Chem., 2010, 53:8387-8399.
Basant et al., "Discovery of a Novel HDAC2 Inhibitor by a Scaffold-Merging Hybrid Query," Comb Chem High Throughput Screen., 2015, 18(7):693-700, Author Manuscript.
Bergman et al., "Selective Histone Deacetylase 6 Inhibitors Bearing Substituted Urea Linkers Inhibit Melanoma Cell Growth," J. Med. Chem., 2012, 55:9891-9899.
Blackburn et al., "Potent Histone Deacetylase Inhibitors Derived from 4-(Aminomethyl)-N-hydroxybenzamide with High Selectivity for the HDAC6 Isoform," J. Med. Chem., 2013, 56:7201-7211.
Brindisi et al., "Phenylpyrrole-based HDAC inhibitors: synthesis, molecular modeling and biological studies," Future Med. Chem., 2016, 8(13):1573-1587.
Buggy et al., "CRA-024781: a novel synthetic inhibitor of histone deacetylase enzymes with antitumor activity in vitro and in vivo," Mol Cancer Ther., 2006, 5:1309-1317.
Butler et al, "Rational Design and Simple Chemistry Yield a Superior, Neuroprotective HDAC6 Inhibitor, Tubastatin A," JACS, Aug. 2010,132:10842-10846.
Butler et al., "Chemical Origins of Isoform Selectivity in Histone Deacetylase Inhibitors," Current Pharmaceutical Design, 2008, 14:505-528.
Butler et al., "Rational Design and Simple Chemistry Yield a Superior, Neuroprotective HDAC6 Inhibitor, Tubastatin A," J. Am. Chem. Soc., 2010, 132:10842-10846.

(Continued)

*Primary Examiner* — Michael G. Hartley
*Assistant Examiner* — Sean R Donohue
(74) *Attorney, Agent, or Firm* — Fish & Richardson P.C.

(57) ABSTRACT

Provided herein are compounds useful for binding to one or more histone deacetylase enzymes (HDACs). The present application further provides radiolabeled compounds useful as a radiotracer for position emission tomography imaging of HDAC. Methods for prepared unlabeled and labeled compounds, diagnostic methods, and methods of treating diseases associated HDAC are also provided.

17 Claims, 6 Drawing Sheets

(56) References Cited

OTHER PUBLICATIONS

Butler et al., "Stereoselective HDAC Inhibition from Cysteine-Derived Zinc-Binding Groups," ChemMedChem, 2009, 4:1292-1301.
Chen et al., "A Series of Potent and Selective, Triazolylphenyl-Based Histone Deacetylases Inhibitors with Activity against Pancreatic Cancer Cells and Plasmodium falciparum," J. Med. Chem., 2008, 51:3437-3448.
Chen et al., "Chemistry and biology of mercaptoacetamides as novel histone deacetylase inhibitors," Bioorg. Med. Chem. Lett., 2005, 15:1389-1392.
Chen et al., "Studies of Benzamide- and Thiol-Based Histone Deacetylase Inhibitors in Models of Oxidative-Stress-Induced Neuronal Death: Identification of Some HDAC3-Selective Inhibitors," ChemMedChem, 2009, 4:842-852.
Cho et al., "Discovery of Pyridone-Based Histone Deacetylase Inhibitors: Approaches for Metabolic Stability," ChemMedChem, 2013, 8:272-279.
Choi et al., "The structural requirements of histone deacetylase inhibitors: Suberoylanilide hydroxamic acid analogs modified at the C3 position display isoform selectivity," Bioorg. Med. Chem. Lett., 2011, 21:6139-6142.
Cuadrado-Tejedor et al, "A First-in-Class Small-Molecule that Acts as a Dual Inhibitor of HDAC and PDE5 and that Rescues Hippocampal Synaptic Impairment in Alzheimer's Disease Mice," Neuropsychopharmacology, 2017, 42(2):524-539.
D'Ydewalle et al, "HDAC6 at the Intersection of Neuroprotection and Neurodegeneration," Traffic, Jun. 2012, 13(6):771-779.
De Vreese et al., "Exploration of thiaheterocyclic hHDAC6 inhibitors as potential antiplasmodial agents," Future Med. Chem., 2017, 9(4):357-364.
De Vreese et al., "Synthesis and applications of benzohydroxamic acid-based histone deacetylase inhibitors," European Journal of Medicinal Chemistry, 2017, 135:174-195.
Delépine et al, "Altered microtubule dynamics and vesicular transport in mouse and human MeCP2-deficient astrocytes," Human Molecular Genetics, Jan. 2016, 25(1):146-157.
Di Micco et al., "Structural basis for the design and synthesis of selective HDAC inhibitors," Bioorganic & Medicinal Chemistry, 2013, 21:3795-3807.
Diedrich et al., "Rational design and diversity-oriented synthesis of peptoid-based selective HDAC6 inhibitors," Chem. Commun., 2016, 52:3219-3222.
Ding et al., "Synthesis and investigation of novel 6-(1,2,3-triazol-4-yl)-4-aminoquinazolin derivatives possessing hydroxamic acid moiety for cancer therapy," Bioorganic & Medicinal Chemistry, 2017, 25:27-37.
Dow et al., "Antimalarial Activity of Phenylthiazolyl-Bearing Hydroxamate-Based Histone Deacetylase Inhibitors," Antimicrob. Agents Chemother., 2008, 52(10):3467-3477.
Du et al, "Histone deacetylase 6 regulates cytotoxic α-synuclein accumulation through induction of the heat shock response," Neurobiology of Aging, 2014, 35(10):2316-2328.
Duan et al., "Design, Synthesis, and Antitumor Evaluation of Novel Histone Deacetylase Inhibitors Equipped with a Phenylsulfonylfuroxan Module as a Nitric Oxide Donor," J. Med. Chem., 2015, 58:4325-4338.
Estiu et al., "On the inhibition of histone deacetylase 8," Bioorganic & Medicinal Chemistry, Jun. 2010, 18(11):4103-4110.
Estiu et al., "Structural origin of selectivity in class II-selective histone deacetylase inhibitors," Journal of Medicinal Chemistry, May 2008, 51(10):2898-2906.
Feng et al., "Novel N-hydroxyfurylacrylamide-based histone deacetylase (HDAC) inhibitors with branched CAP group (Part 2)," Bioorganic & Medicinal Chemistry, 2013, 21:5339-5354.
Fiskus et al., "Hydroxamic Acid Analogue Histone Deacetylase Inhibitors Attenuate Estrogen Receptor-A Levels and Transcriptional Activity: A Result of Hyperacetylation and Inhibition of Chaperone Function of Heat Shock Protein 90," Clin Cancer Res., 2007, 13(16):4882-4890.
Gaisina et al., "Identification of HDAC6-Selective Inhibitors of Low Cancer Cell Cytotoxicity," ChemMedChem, 2016, 11:81-92.
Galletti et al., "Azetidinones as Zinc-Binding Groups to Design Selective HDAC8 Inhibitors," ChemMedChem, 2009, 4:1991-2001.
Giannini et al., "N-Hydroxy-(4-oxime)-cinnamide: A versatile scaffold for the synthesis of novel histone deacetilase (HDAC) inhibitors," Bioorg. Med. Chem. Lett., 2009, 19:2346-2349.
Gold et al, "MeCP2 deficiency is associated with reduced levels of tubulin acetylation and can be restored using HDAC6 inhibitors," Journal of Molecular Medicine, Jan. 2015, 93(1):63-72.
Goracci et al., "A Rational Approach for the Identification of Non-Hydroxamate HDAC6-Selective Inhibitors," Scientific Reports, 2016, 6:29086, 12 pages.
Guandalini et al., "Design, synthesis and preliminary evaluation of a series of histone deacetylase inhibitors carrying a benzodiazepine ring," European Journal of Medicinal Chemistry, 2013, 66:56-68.
Haggarty et al., "Domain-selective small-molecule inhibitor of histone deacetylase 6 (HDAC6)-mediated tubulin deacetylation," PNAS, 2003, 100(8):4389-4394.
Hai et al., "Histone deacetylase 6 structure and molecular basis of catalysis and inhibition," Nat. Chem. Biol., 2016, 12:741-747.
Hooker et al., "Histone Deacetylase Inhibitor MS-275 Exhibits Poor Brain Penetration: Pharmacokinetic Studies of [11C]MS-275 using Positron Emission Tomography," ACS Chem. Neurosci., 2010, 1:65-73.
Itoh et al., "Design, Synthesis, Structure-Selectivity Relationship, and Effect on Human Cancer Cells of a Novel Series of Histone Deacetylase 6-Selective Inhibitors," J. Med. Chem., 2007, 50:5425-5438.
Jadhavar et al., "Targeting prostate cancer with compounds possessing dual activity as androgen receptor antagonists and HDAC6 inhibitors," Bioorg. Med. Chem. Lett., 2016, 26:5222-5228.
Jochems et al, "Antidepressant-like properties of novel HDAC6-selective inhibitors with improved brain bioavailability," Neuropsychopharmacology, Oct. 2014, 39(2):389-400.
Jose et al., "Toward an HDAC6 inhibitor: synthesis and conformational analysis of cyclic hexapeptide hydroxamic acid designed from -tubulin sequence," Bioorganic & Medicinal Chemistry, 2004, 12:1351-1356.
Jung et al., "Novel HDAC Inhibitors with Radiosensitizing Properties," Radiation Research, 2005, 163(5):488-493.
Jung et al., "Rational Design and Development of Radiation-Sensitizing Histone Deacetylase Inhibitors," Chemistry & Biodiversity, 2005, 2:1452-1461.
Kalin et al., "Chiral Mercaptoacetamides Display Enantioselective Inhibition of Histone Deacetylase 6 and Exhibit Neuroprotection in Cortical Neuron Models of Oxidative Stress," ChemMedChem, 2012, 7:425-439.
Kim et al., "Whole-body pharmacokinetics of HDAC inhibitor drugs, butyric acid, valproic acid and 4-phenylbutyric acid measured with carbon-11 labeled analogs by PET," Nuclear Medicine and Biology, 2013, 40:912-918.
Kozikowski et al., "Chemistry, Biology, and QSAR Studies of Substituted Biaryl Hydroxamates and Mercaptoacetamides as HDAC inhibitors—Nanomolar Potency Inhibitors of Pancreatic Cancer Cell Growth," ChemMedChem, 2008, 3(3):487-501, Author Manuscript.
Kozikowski et al., "Functional Differences in Epigenetic Modulators—Superiority of Mercaptoacetamide-Based Histone Deacetylase Inhibitors Relative to Hydroxamates in Cortical Neuron Neuroprotection Studies," J. Med. Chem., 2007, 50:3054-3061.
Kozikowski et al., "Searching for Disease Modifiers—PKC Activation and HDAC Inhibition—A Dual Drug Approach to Alzheimer's Disease that Reduces Aβ Production while Blocking Oxidative Stress," ChemMedChem, 2009, 4(7):1095-1105, Author Manuscript.
Kozikowski et al., "Use of the Nitrile Oxide Cycloaddition (NOC) Reaction for Molecular Probe Generation: A New Class of Enzyme

(56) References Cited

OTHER PUBLICATIONS

Selective Histone Deacetylase Inhibitors (HDACIs) Showing Picomolar Activity at HDAC6," J. Med. Chem., 2008, 51:4370-4373.
Krieger et al., "Design, Multicomponent Synthesis, and Anticancer Activity of a Focused Histone Deacetylase (HDAC) Inhibitor Library with Peptoid-Based Cap Groups," J. Med. Chem., 2017, 60:5493-5506.
Li et al, "Histone deacetylase 6 promotes growth of glioblastoma through inhibition of SMAD2 signaling," Tumor Biology, Dec. 2015, 36(12):9661-9665.
Li et al., "Discovery of the First N-Hydroxycinnamamide-Based Histone Deacetylase 1/3 Dual Inhibitors with Potent Oral Antitumor Activity," J. Med. Chem., 2014, 57:3324-3341.
Lin et al., "Design and Synthesis of Orally Bioavailable Aminopyrrolidinone Histone Deacetylase 6 Inhibitors," J. Med. Chem., 2015, 58:2809-2820.
Liu et al., "Design, synthesis and evaluate of novel dual FGFR1 and HDAC inhibitors bearing an indazole scaffold," Bioorganic & Medicinal Chemistry, 2018, 26:747-757.
Lucio-Eterovic et al, "Differential expression of 12 histone deacetylase (HDAC) genes in astrocytomas and normal brain tissue: class II and IV are hypoexpressed in glioblastomas," BMC Cancer, Dec. 2008, 8(1):243.
Manku et al., "Synthesis and evaluation of lysine derived sulfamides as histone deacetylase inhibitors," Bioorg. Med. Chem. Lett., 2009, 19:1866-1870.
Mendoza-Sanchez et la., "Design, synthesis and evaluation of antiestrogen and histone deacetylase inhibitor molecular hybrids," Bioorganic & Medicinal Chemistry, 2015, 23:7597-7606.
Mottamal et al, "Histone deacetylase inhibitors in clinical studies as templates for new anticancer agents," Molecules (Basel, Switzerland), Mar. 2015, 20(3):3898-3941.
Muthyala et al., "Discovery of 1-hydroxypyridine-2-thiones as selective histone deacetylase inhibitors and their potential application for treating leukemia," Bioorg. Med. Chem. Lett., 2015, 25:4320-4324.
Olsen et al., "Macrocyclic Peptoid-Peptide Hybrids as Inhibitors of Class I Histone Deacetylases," ACS Med. Chem. Lett., 2012, 3:749-753.
Pangborn et al, "Safe and Convenient Procedure for Solvent Purification," Organometallics, 1996, 15:1518-1520.
PCT International Preliminary Report on Patentability in International Appln. No. PCT/US2018/027077, dated Oct. 15, 2019, 6 pages.
PCT International Search Report and Written Opinion in International Appln. No. PCT/US2018/027077, dated Jul. 5, 2018, 11 pages.
Pham-The et al., "Quantitative structure-activity relationship analysis and virtual screening studies for identifying HDAC2 inhibitors from known HDAC bioactive chemical libraries," SAR and QSAR in Environmental Research, 2017, 28(3):199-220.
Raji et al., "Design, synthesis and evaluation of antiproliferative activity of melanoma-targeted histone deacetylase inhibitors," Bioorg. Med. Chem. Lett., 2017, 27:744-749.
Reid et al., "Evaluation of 6-([18F]fluoroacetamido)-1-hexanoicanilide for PET imaging of histone deacetylase in the baboon brain," Nuclear Medicine and Biology, 2009, 36:247-258.
Rivieccio et al., "HDAC6 is a target for protection and regeneration following injury in the nervous system," PNAS, 2009, 106(46):19599-19604.
Rodrigues et al., "Beyond the Selective Inhibition of Histone Deacetylase 6," Mini-Reviews in Medicinal Chemistry, 2016, 16:1175-1184.
Rodrigues et al., "Design, Synthesis, and Pharmacological Evaluation of Novel N-Acylhydrazone Derivatives as Potent Histone Deacetylase 6/8 Dual Inhibitors," J. Med. Chem., 2016, 59:655-670.
Rodríguez-Fonseca et al., "Design, Synthesis and Biological Evaluation of a Phenyl Butyric Acid Derivative, N-(4-chlorophenyl)-4-phenylbutanamide: A HDAC6 Inhibitor with Anti-proliferative Activity on Cervix Cancer and Leukemia Cells," Anti-Cancer Agents in Medicinal Chemistry, 2017, 17(10):1441-1454.
Santo et al, "Preclinical activity, pharmacodynamic, and pharmacokinetic properties of a selective HDAC6 inhibitor, ACY-1215, in combination with bortezomib in multiple myeloma," Blood, Mar. 2012, 119(11):2579-2589.
Schroeder et al., "PET Imaging Demonstrates Histone Deacetylase Target Engagement and Clarifies Brain Penetrance of Known and Novel Small Molecule Inhibitors in Rat," ACS Chem. Neurosci., 2014, 5:1055-1062.
Seo et al., "Image-guided synthesis reveals potent blood-brain barrier permeable histone deacetylase inhibitors," ACS Chem. Neurosci. Jul. 2014, 5(7):588-596.
Seo et al., "Radionuclide labeling and evaluation of candidate radioligands for PET imaging of histone deacetylase in the brain," Bioorg. Med. Chem. Lett., 2013, 23:6700-6705.
Sixto-López et al., "Searching the conformational complexity and binding properties of HDAC6 through docking and molecular dynamic simulations," Journal of Biomolecular Structure and Dynamics, 2017, 35(13):2794-2814.
Smil et al., "Novel HDAC6 isoform selective chiral small molecule histone deacetylase inhibitors," Bioorg. Med. Chem. Lett., 2009, 19:688-692.
Strebl et al., "Development of a Fluorinated Class-I HDAC Radiotracer Reveals Key Chemical Determinants of Brain Penetrance," ACS Chem. Neurosci., 2016, 7:528-533.
Strebl et al., "HDAC6 brain mapping with [18f] bavarostat enabled by a Ru-mediated deoxyfluorination," ACS Cent. Sci., Sep. 2017, 3(9):1006-1014.
Su et al, "HDAC6 regulates aggresome-autophagy degradation pathway of α-synuclein in response to MPP+-induced stress," Journal of Neurochemistry, Apr. 2011, 117(1):112-120.
Suzuki et al., "Highly Potent and Selective Histone Deacetylase 6 Inhibitors Designed Based on a Small-Molecular Substrate," J. Med. Chem., 2006, 49:4809-4812.
Tago et al., "Advances in the Development of PET Ligands Targeting Histone Deacetylases for the Assessment of Neurodegenerative Diseases," Molecules, 2018, 23(2):300, 27 pages.
Tan et al., "Design, synthesis and tumor cell growth inhibitory activity of 3-nitro-2H-cheromene derivatives as histone deacetylaes inhibitors," Bioorganic & Medicinal Chemistry, 2017, 25:4123-4132.
Tang et al., "Novel Inhibitors of Human Histone Deacetylase (HDAC) Identified by QSAR Modeling of Known Inhibitors, Virtual Screening, and Experimental Validation," J. Chem. Inf. Model., 2009, 49:461-476.
Tapadar et al., "Isoxazole moiety in the linker region of HDAC inhibitors adjacent to the Zn-chelating group: Effects on HDAC biology and antiproliferative activity," Bioorg. Med. Chem. Lett., 2009, 19:3023-3026.
Tashima et al., "Design and synthesis of novel and highly-active pan-histone deacetylase (pan-HDAC) inhibitors," Bioorganic & Medicinal Chemistry, 2014, 22:3720-3731.
Tavares et al., "Synthesis and Pharmacological Evaluation of Selective Histone Deacetylase 6 Inhibitors in Melanoma Models," ACS Med. Chem. Lett., 2017, 8:1031-1036.
Uba et al., "Exploration of the binding pocket of histone deacetylases: the design of potent and isoform-selective inhibitors," Turk J Biol . . . , 2017, 41: 901-918.
Vermeulen et al., "Evaluation of [11C]KB631 as a PET tracer for in vivo visualisation of HDAC6 in B16.F10 melanoma," Nuclear Medicine and Biology, 2019, 74-75:1-11.
Wagner et al., "Potent and Selective Inhibition of Histone Deacetylase 6 (HDAC6) Does Not Require a Surface-Binding Motif," J. Med. Chem., 2013, 56:1772-1776.
Wang et al, "Computational studies on the histone deacetylases and the design of selective histone deacetylase inhibitors," 2009, 9(3):241-256).
Wang et al, "HDAC6 promotes cell proliferation and confers resistance to temozolomide in glioblastoma," Cancer Letters, Aug. 2016, 379(1):134-142.

(56) References Cited

OTHER PUBLICATIONS

Wang et al., "Acylurea connected straight chain hydroxamates as novel histone deacetylase inhibitors: Synthesis, SAR, and in vivo antitumor activity," Bioorg. Med. Chem. Lett., 2010, 20:3314-3321.

Wang et al., "Design, synthesis and biological evaluation of thienopyrimidine hydroxamic acid based derivatives as structurally novel histone deacetylase (HDAC) inhibitors," European Journal of Medicinal Chemistry, 2017, 128:293-299.

Wang et al., "Design, synthesis, and evaluation of hydroxamic acid-based molecular probes for in vivo imaging of histone deacetylase (HDAC) in brain," Am J Nucl Med Mol Imaging, 2014, 4(1):29-38.

Wang et al., "In Vivo Imaging of Histone Deacetylases (HDACs) in the Central Nervous System and Major Peripheral Organs," J. Med. Chem., 2014, 57:7999-8009.

Wen et al., "Identification of N-(6-mercaptohexyl)-3-(4-pyridyl)-1H-pyrazole-5-carboxamide and its disulfide prodrug as potent histone deacetylase inhibitors with in vitro and in vivo anti-tumor efficacy," European Journal of Medicinal Chemistry, 2016, 109:350-359.

Wey et al., "Insights into neuroepigenetics through human histone deacetylase PET imaging," Sci Transl Med., 2016, 8(351):351ra106, 23 pages, Author Manuscript.

Wey et al., "Kinetic Analysis and Quantification of [11C]Martinostat for in Vivo HDAC Imaging of the Brain," ACS Chem. Neurosci., 2015, 6:708-715.

Wong et al., "Structural Biasing Elements for In-Cell Histone Deacetylase Paralog Selectivity," J. Am. Chem. Soc., 2003, 125:5586-5587.

Yang et al., "Design and Synthesis of Janus Kinase 2 (JAK2) and Histone Deacetlyase (HDAC) Bispecific Inhibitors Based on Pacritinib and Evidence of Dual Pathway Inhibition in Hematological Cell Lines," J. Med. Chem., 2016, 59:8233-8262.

Yang et al., "Design, synthesis and biological evaluation of 4-anilinothieno[2,3-d]pyrimidine-based hydroxamic acid derivatives as novel histone deacetylase inhibitors," Bioorganic & Medicinal Chemistry, 2014, 22:6146-6155.

Yang et al., "Design, synthesis and biological evaluation of novel hydroxamic acid based histone deacetylase 6 selective inhibitors bearing phenylpyrazol scaffold as surface recognition motif," Bioorganic & Medicinal Chemistry, 2018, 26:1418-1425.

Yang et al., "Discovery of Selective Histone Deacetylase 6 Inhibitors Using the Quinazoline as the Cap for the Treatment of Cancer," J. Med. Chem., 2016, 59:1455-1470.

Yoo et al., "Computer-aided identification of new histone deacetylase 6 selective inhibitor with anti-sepsis activity," European Journal of Medicinal Chemistry, 2016, 116:126-135.

Yoshida et al., "From Discovery to the Coming Generation of Histone Deacetylase Inhibitors," Current Medicinal Chemistry, 2003, 10:2351-2358.

Yuan et al., "Design, synthesis and anticancer potential of NSC-319745 hydroxamic acid derivatives as DNMT and HDAC inhibitors," European Journal of Medicinal Chemistry, 2017, 134:281-292.

Zhang et al., "Histone Deacetylase Inhibitors with Enhanced Enzymatic Inhibition Effects and Potent in vitro and in vivo Antitumor Activities," ChemMedChem, 2014, 9:638-648.

Zwick et al., "Synthesis of a selective HDAC6 inhibitor active in neuroblasts," Bioorg. Med. Chem. Lett., 2016, 26:4955-4959.

Office Action in Chinese Appln. No. 201880038278.4, dated Mar. 30, 2022, 16 pages (with English translation).

CAS No. 1332894-18-4, "Benzamide, N-hydroxy-4-[(1R)-1-[[(1-methlcyclohexyl)methyl]amino]ethyl]," dated Sep. 20, 2011, 1 page.

CAS No. 1860746-44-6, "3-Pyridinecarboxamide, 6-(cyclopropylamino)-N-hydroxy-," dated Feb. 5, 2016, 1 page.

CAS No. 1875612-53-5, "3-Pyridinecarboxamide, 6-[(cyclopropymethyl)amino]-N-hydroxy-," dated Feb. 28, 2016, 1 page.

CAS No. 73779-41-6, "Benzamide, 4-(cyclohexylamino)-N-hydroxy-," dated Nov. 16, 1984, 1 page.

Hendricks et al., "In vivo PET imaging of histone deacetylases by 18F-suberoylanilide hydroxamic acid(18F-SAHA)," Journal of Medical Chemistry, Jul. 2011, 54(15):5576-5582.

Kattar et al., "Parallel medicinal chemistry approaches to selective HDAC1/HDAC2 inhibitor(SHI-1:2) optimization," Bioorganic & Medicinal Chemistry Letters, Dec. 2008, 19(4):1168-1172.

Office Action in Japanese Appln. No. 2019-555586, dated Dec. 21, 2021, 16 pages (with English translation).

* cited by examiner

HDAC6 INHIBITORS AND IMAGING AGENTS

CROSS-REFERENCE TO RELATED APPLICATIONS

This application is a continuation of U.S. patent application Ser. No. 16/603,746, filed Oct. 8, 2019, which is a § 371 National Stage Application of PCT/US2018/027077, filed Apr. 11, 2018, which claims the benefit of U.S. Provisional Application Ser. No. 62/484,207, filed Apr. 11, 2017, the disclosure of which is incorporated herein by reference in its entirety.

FEDERALLY SPONSORED RESEARCH OR DEVELOPMENT

This invention was made with Government support under Grant No. R01 NS099250 awarded by the National Institutes of Health. The Government has certain rights in the invention.

TECHNICAL FIELD

The present application provides compounds useful for inhibiting a histone deacetylase (HDAC) enzyme. The present application further provides compounds (e.g., labeled or unlabeled compounds) useful for treating diseases associated with abnormal expression levels and/or activity of a histone deacetylase (HDAC) enzyme and methods of imaging an HDAC enzyme using radiolabeled compounds.

BACKGROUND

Histone deacetylases (HDACs) are a family of chromatin modifying enzymes that modulate DNA packaging, gene expression and have been linked to biological functions from differentiation at the cellular level to higher-order brain function via behavioral changes at the organismal level. Evidence increasingly supports that targeting epigenetic mechanisms and chromatin-mediated neuroplasticity may improve treatments for neuropsychiatric diseases.

SUMMARY

The present application provides, inter alia, a compound of Formula I:

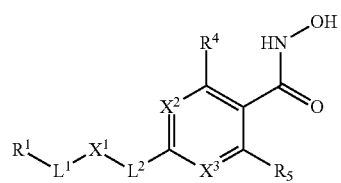

I or a pharmaceutically acceptable salt thereof, wherein:
$X^1$ is —N($R^N$)— or —CH($R^C$)—;
$X^2$ is $CR^2$ or N;
$X^3$ is $CR^3$ or N;
$R^N$ is selected from the group consisting of H, $C_{1-6}$ alkyl, and $C_{1-6}$ haloalkyl;
$R^C$ is selected from the group consisting of H, $C_{1-6}$ alkyl, and $C_{1-6}$ haloalkyl;
$L^1$ is a bond or is selected from the group consisting of a $C_{1-6}$ alkylene group, a linking $C_{3-10}$ cycloalkyl group, and a linking 4-10 membered heterocycloalkyl group, wherein the 4-10 membered heterocycloalkyl group is optionally substituted by 1 or 2 independently $C_{1-6}$ alkyl groups;
$L^2$ is a bond or is a $C_{1-6}$ alkylene group;
$R^1$ is selected from the group consisting of $C_{1-6}$ alkyl, $C_{1-6}$ alkoxy, $C_{3-10}$ cycloalkyl, and $C_{6-10}$ aryl, wherein the $C_{3-10}$ cycloalkyl and $C_{6-10}$ aryl are each optionally substituted by 1 or 2 independently selected halo groups;
$R^2$, $R^3$, $R^4$, and $R^5$ are each independently selected from the group consisting of H, halo, and $C_{1-6}$ haloalkyl.

In some embodiments, $X^1$ is —N($R^N$)—. In some embodiments, $R^N$ is selected from the group consisting of H and methyl.

In some embodiments, $X^1$ is —CH($R^C$)—. In some embodiments, $R^C$ is H.

In some embodiments, $L^1$ is a bond. In some embodiments, $L^1$ is selected from the group consisting of a $C_{1-6}$ alkylene group, a linking $C_{3-10}$ cycloalkyl group, and a linking 4-10 membered heterocycloalkyl group, wherein the 4-10 membered heterocycloalkyl group is optionally substituted by 1 or 2 independently $C_{1-6}$ alkyl groups. In some embodiments, $L^1$ is selected from the group consisting of methylene,

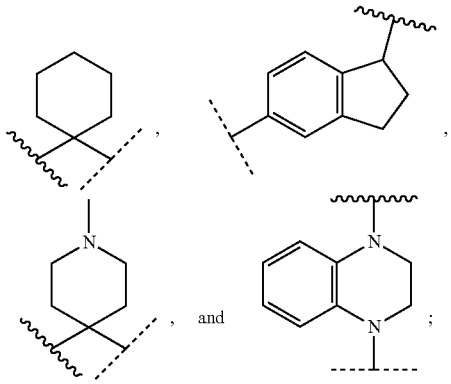

wherein:
〜〜〜 indicates the bond between $L^1$ and $X^1$; and
---- indicates the bond between $L^1$ and $R^1$.

In some embodiments, $L^2$ is a bond. In some embodiments, $L^2$ is methylene.

In some embodiments, $R^1$ is selected from the group consisting of $C_{1-3}$ alkyl, $C_{1-3}$ alkoxy, $C_{6-10}$ cycloalkyl, and phenyl, wherein the phenyl is optionally substituted by 1 or 2 independently selected halo groups. In some embodiments, $R^1$ is selected from the group consisting of methyl, methoxy, cyclohexyl, adamantyl, norbornyl, phenyl, and 3-fluorophenyl.

In some embodiments, $X^2$ is N. In some embodiments, $X^2$ is $CR^2$. In some embodiments, $R^2$ is H or F. In some embodiments, $R^2$ is F.

In some embodiments, $X^3$ is N. In some embodiments, $X^3$ is $CR^3$. In some embodiments, $R^3$ is H or F. In some embodiments, $R^3$ is H.

In some embodiments, $X^2$ and $X^3$ are each N. In some embodiments, $X^2$ is $CR^2$ and $X^3$ is $CR^3$. In some embodiments, $R^2$ is F and $R^3$ is H.

In some embodiments, $R^4$ is H or $CF_3$. In some embodiments, $R^4$ is H.

In some embodiments, $R^5$ is H or $CF_3$.

In some embodiments, $R^5$ is H.

In some embodiments, $R^2$ is F and $R^3$, $R^4$, and $R^5$ are each H.

In some embodiments:

$X^1$ is —N($R^N$)— or —$CH_2$—;

$X^2$ is $CR^2$ or N;

$X^3$ is $CR^3$ or N;

$R^N$ is selected from the group consisting of H and methyl;

$L^1$ is a bond or selected from the group consisting of a $C_{1-3}$ alkylene group, a linking $C_{6-10}$ cycloalkyl group, and a linking 4-10 membered heterocycloalkyl group, wherein the 4-10 membered heterocycloalkyl group is optionally substituted by 1 or 2 independently $C_{1-3}$ alkyl groups;

$L^2$ is a bond or methylene;

$R^1$ is selected from the group consisting of $C_{1-3}$ alkyl, $C_{1-3}$ alkoxy, $C_{6-10}$ cycloalkyl, and phenyl, wherein the phenyl is optionally substituted by 1 or 2 independently selected halo groups;

$R^2$ is selected from the group consisting of H and halo; and $R^3$, $R^4$, and $R^5$ are each H.

In some embodiments:

$X^1$ is —N($R^N$)— or —$CH_2$—;

$X^2$ is $CR^2$ or N;

$X^3$ is $CR^3$ or N;

$R^N$ is selected from the group consisting of H and methyl;

$L^1$ is a bond or is selected from the group consisting of methylene,

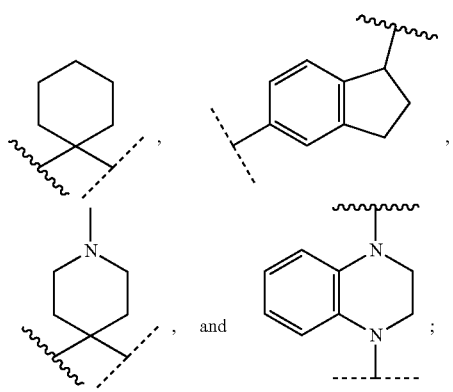

wherein:

〰 indicates the bond between $L^1$ and $X^1$; and

---- indicates the bond between $L^1$ and $R^1$;

$L^2$ is a bond or methylene;

$R^1$ is selected from the group consisting of $C_{1-3}$ alkyl, $C_{1-3}$ alkoxy, $C_{6-10}$ cycloalkyl, and phenyl, wherein the phenyl is optionally substituted by 1 or 2 independently selected halo groups;

$R^2$ is selected from the group consisting of H and halo; and $R^3$, $R^4$, and $R^5$ are each H.

In some embodiments, the compound of Formula I is a compound of Formula II:

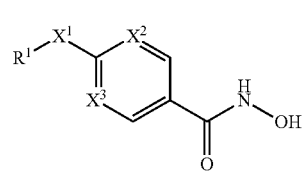

or a pharmaceutically acceptable salt thereof.

In some embodiments, the compound of Formula I is a compound of Formula III:

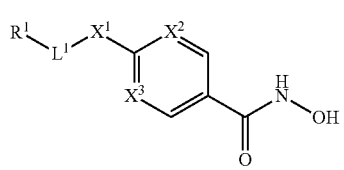

or a pharmaceutically acceptable salt thereof.

In some embodiments, the compound of Formula I is a compound of Formula IV:

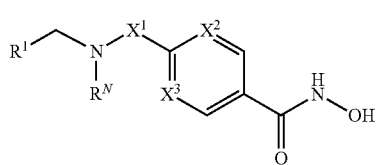

or a pharmaceutically acceptable salt thereof.

In some embodiments, the compound of Formula I is a compound of Formula V:

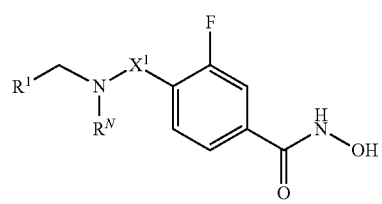

or a pharmaceutically acceptable salt thereof.

In some embodiments, the compound or pharmaceutically acceptable salt provided herein comprises at least one radioisotope. In some embodiments, the compound or pharmaceutically acceptable salt provided herein comprises at least one radioisotope selected from the group consisting of $^{11}C$ and $^{18}F$. In some embodiments, the compound or pharmaceutically acceptable salt provided herein comprises at least one $^{18}F$ radioisotope.

In some embodiments, the compound of Formula I is a compound of Formula VI:

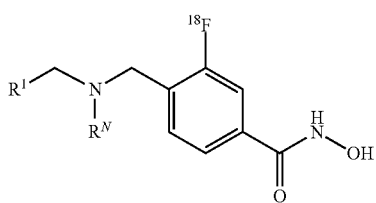

or a pharmaceutically acceptable salt thereof.

In some embodiments, the compound of Formula I is a compound selected from the group consisting of:

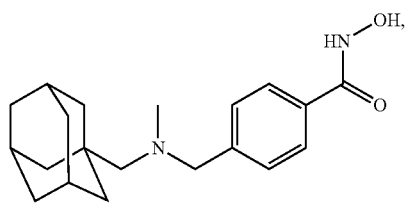

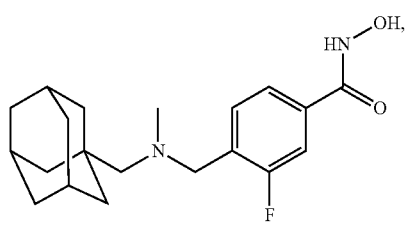

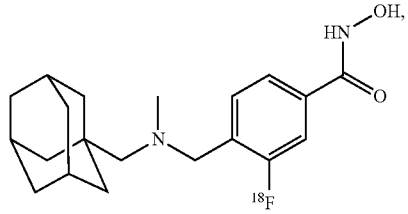

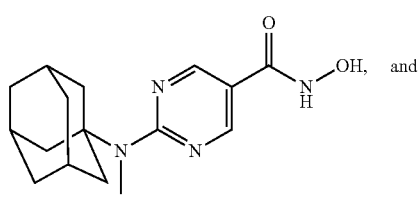

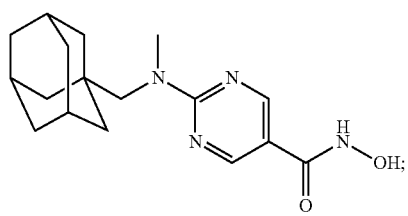

or a pharmaceutically acceptable salt thereof.

In some embodiments, the compound of Formula I is selected from the group consisting of:

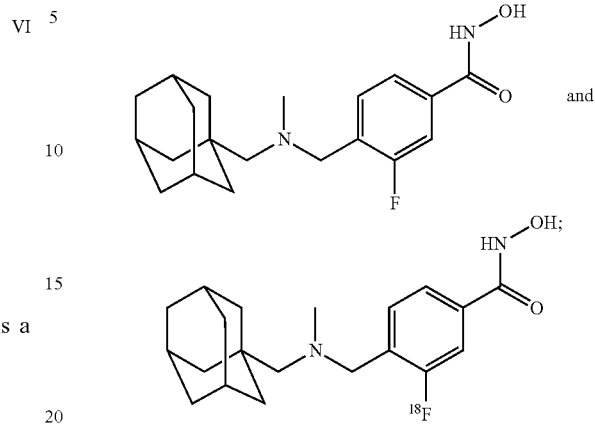

or a pharmaceutically acceptable salt thereof.

The present application further provides a pharmaceutical composition, comprising compound provided herein, or a pharmaceutically acceptable salt thereof, and at least one pharmaceutically acceptable carrier.

The present application further provides a method of inhibiting an activity of a histone deacetylase (HDAC) enzyme, comprising contacting the HDAC enzyme with a compound provided herein, or a pharmaceutically acceptable salt thereof. In some embodiments, inhibiting an activity of a histone deacetylase (HDAC) enzyme comprises deregulating the histone deacetylase (HDAC) enzyme. In some embodiments, the histone deacetylase (HDAC) enzyme is HDAC6. In some embodiments, the compound selectively inhibits HDAC6 one or more of HDAC1, HDAC2, HDAC3, HDAC4, HDAC5, HDAC7, HDAC8, HDAC9, HDAC10, and HDAC11.

In some embodiments, the method is an in vitro method. In some embodiments, the method is an in vivo method.

The present application further provides a method of imaging a subject, comprising:
i) administering to the subject a radiolabeled compound provided herein, or a pharmaceutically acceptable salt thereof; and
ii) imaging the subject with an imaging technique.

The present application further provides a method of imaging a histone deacetylase (HDAC) enzyme in a cell or tissue, comprising:
i) contacting the cell or tissue with a radiolabeled compound provided herein, or a pharmaceutically acceptable salt thereof; and
ii) imaging the cell or tissue with an imaging technique.

The present application further provides a method of imaging a histone deacetylase (HDAC) enzyme in a subject, comprising:
i) administering to the subject a radiolabeled compound provided herein, or a pharmaceutically acceptable salt thereof; and
ii) imaging the subject with an imaging technique.

The present application further provides a method of imaging a disease associated with abnormal expression or abnormal activity of a histone deacetylase (HDAC) enzyme in a subject, the method comprising:
i) administering to the subject a radiolabeled compound provided herein, or a pharmaceutically acceptable salt thereof; and
ii) imaging the subject with an imaging technique.

The present application further provides a method of monitoring treatment of a disease associated with abnormal expression or abnormal activity of a histone deacetylase (HDAC) enzyme in a subject, comprising:
  i) imaging the subject with an imaging technique;
  ii) administering to the subject a therapeutically effective amount of a compound provided herein, or a pharmaceutically acceptable salt thereof,
  iii) imaging the subject with an imaging technique; and
  iv) comparing the image of step i) and the image of step iii).

In some embodiments, the imaging technique is selected from the group consisting of single-photon emission computed tomography, positron emission tomography imaging, computed tomography, positron emission tomography with computed tomography imaging, positron emission tomography with magnetic resonance imaging. In some embodiments, the imaging technique is positron emission tomography imaging. In some embodiments, the histone deacetylase (HDAC) enzyme is HDAC6.

The present application further provides a method of imaging the brain in a subject, comprising:
  i) administering to the subject a radiolabeled compound provided herein, or a pharmaceutically acceptable salt thereof; and
  ii) imaging the subject with an imaging technique.

The present application further provides a method of treating a disease in a subject in need thereof, the method comprising administering to the subject a therapeutically effective amount of a compound provided herein, or a pharmaceutically acceptable salt thereof, wherein the disease is selected from the group consisting of cancer, a disease of the central nervous system, and an inflammatory autoimmune disease.

In some embodiments, the disease is cancer. In some embodiments, cancer comprises a solid tumor. In some embodiments, the cancer is selected from the group consisting of glioma, glioblastoma, and non-small cell lung cancer. In some embodiments, the cancer is a hematological cancer. In some embodiments, the hematological cancer is selected from the group consisting of leukemia and lymphoma. In some embodiments, the cancer is associated with abnormal expression or abnormal activity of a histone deacetylase (HDAC) enzyme. In some embodiments, the cancer is associated with abnormal expression or abnormal activity of HDAC6.

In some embodiments, the disease is a disease of the central nervous system. In some embodiments, the disease of the central nervous system comprises a neurodegenerative disease. In some embodiments, the disease of the central nervous system is depression. In some embodiments, the disease of the central nervous system is selected from the group consisting of schizophrenia, bipolar disorder, Alzheimer's disease, and Huntington's disease. In some embodiments, the disease of the central nervous system further comprises depression. In some embodiments, the disease of the central nervous system is associated with abnormal expression or abnormal activity of a histone deacetylase (HDAC) enzyme. In some embodiments, the disease of the central nervous system is associated with abnormal expression or abnormal activity of HDAC6.

In some embodiments, the disease is an inflammatory autoimmune disease. In some embodiments, the inflammatory autoimmune disease is associated with abnormal expression or abnormal activity of a histone deacetylase (HDAC) enzyme. In some embodiments, the inflammatory autoimmune disease is associated with abnormal expression or abnormal activity of HDAC6.

In some embodiments, about 0.1% to about 5% of the compound administered crosses the blood brain barrier. In some embodiments, the compound administered has a brain:plasma ratio of from at least about 1:1 to at least about 50:1.

The present application further provides a method of treating a cancer in a subject, comprising:
  i) identifying the cancer as being associated with abnormal activity or abnormal expression of a histone deacetylase (HDAC) enzyme; and
  ii) administering to the subject a therapeutically effective amount of a compound provided herein, or a pharmaceutically acceptable salt thereof.

The present application further provides a method of treating a disease of the central nervous in a subject, comprising:
  i) identifying the disease of the central nervous system as being associated with abnormal activity or abnormal expression of a histone deacetylase (HDAC) enzyme; and
  ii) administering to the subject a therapeutically effective amount of a compound provided herein, or a pharmaceutically acceptable salt thereof.

The present application further provides a method of treating an inflammatory autoimmune disease in a subject, the method comprising:
  i) identifying the inflammatory autoimmune disease as being associated with abnormal activity or abnormal expression of a histone deacetylase (HDAC) enzyme; and
  ii) administering to the subject a therapeutically effective amount of a compound provided herein, or a pharmaceutically acceptable salt thereof.

In some embodiments, the histone deacetylase (HDAC) enzyme is HDAC6.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

DESCRIPTION OF DRAWINGS

FIG. 7B, Top Panel: Example 2, no competitor; Middle Panel: Example 2+Example 1; Bottom Panel: Example 2+tubastatin A.

DETAILED DESCRIPTION

Figure 1:
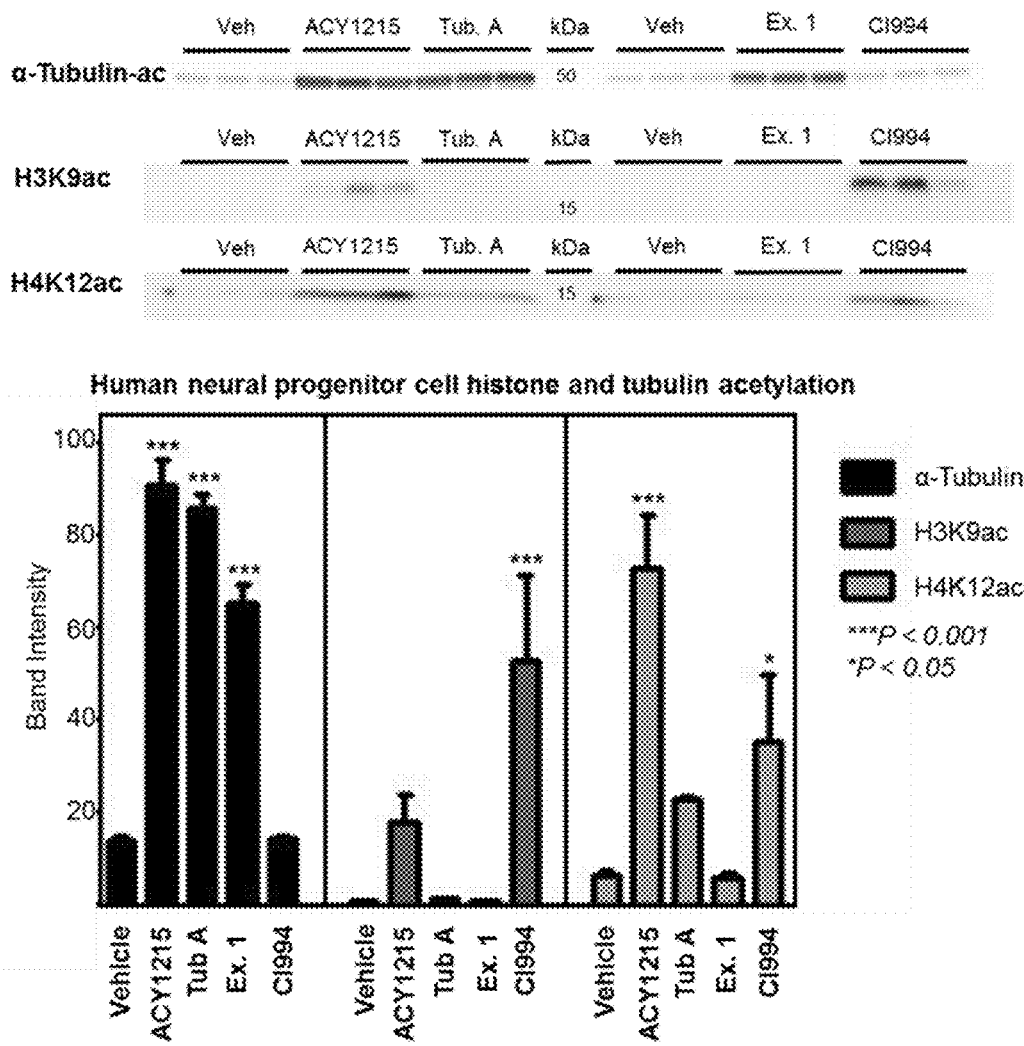
FIG. 1 shows results of a human neural progenitor cell histone and tubulin acetylation assay.

Histone Deacetylases have emerged as a pharmaceutical target with a range of promising indications. Several pan-HDAC inhibitors, which target multiple of the 11 isoforms of Zn-dependent HDACs, are approved by the FDA or are currently in clinical trials (see e.g., Mottamal et al, *Molecules* (Basel, Switzerland), 2015, 20(3):3898-3941). However, these non-selective agents typically lead to undesired side effects (see e.g., Estiu et al, *Bioorganic & Medicinal Chemistry*, 2010, 18(11):4103-4110; Estiu et al, *Journal of Medicinal Chemistry*, 2008, 51(10):2898-2906; and Difei et al, *Current Topics in Medicinal Chemistry*, 2009, 9(3):241-256).

The cytosolic location and structure of HDAC6 is unique among the isoforms and HDAC6-selective treatment regimens have shown promise to avoid many of the side effects of first-generation pan-HDAC inhibitors (see e.g., Santo et al, *Blood*, 2012, 119(11):2579-2589). Isoform selectivity is difficult to engineer and HDAC6 is structurally different from other isoforms to offer a starting point for rational design of selective inhibitors.

Aberrant HDAC6 expression levels have been implicated in the pathophysiology of glioblastoma multiforme (see e.g., Li et al, *Tumor Biology*, 2015, 36(12):9661-9665; Wang et al, *Cancer Letters*, 2016, 379(1):134-142; and Lucio-Eterovic et al, *BMC Cancer*, 2008, 8(1):243), Rett syndrome (see e.g., Delépine et al, *Human Molecular Genetics*, 2015, 25(1):146-157; and Gold et al, *Journal of Molecular Medicine*, 2015, 93(1):63-72), Alzheimer's disease (see e.g., Anderson et al, *PLOS ONE*, 2015, 10(5):e0126592; and Cuadrado-Tejedor et al, *Neuropsychopharmacology*, 2017, 42(2):524-539) and Parkinson's disease (see e.g., d'Ydewalle et al, *Traffic*, 2012, 13(6):771-779; Su et al, *Journal of Neurochemistry*, 2011, 117(1):112-120; and Du et al, *Neurobiology of Aging*, 2014, 35(10):2316-2328), but the understanding of these correlations in the living human brain remains limited. Furthermore, the design of brain-penetrant HDAC6 selective agents has proven challenging, and high doses are often needed to achieve functional effects of HDAC6 inhibition (see e.g., Jochems et al, *Neuropsychopharmacology*, 2014, 39(2):389-400).

Positron emission tomography (PET) has potential to increase the understanding of human neuroepigenetics and related processes, and a probe to study HDAC6 has potential for gaining insight into the molecular underpinnings of brain function and disease, and in the validation of therapeutic targets and therapeutic small molecules. Accordingly, the present application describes the development of a brain penetrant, selective HDAC6-inhibitor, and its application in PET imaging.

Compounds

The present application provides a compound of Formula I:

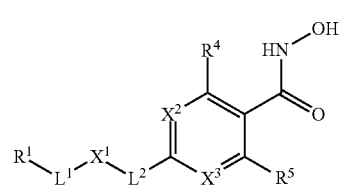

or a pharmaceutically acceptable salt thereof, wherein:
$X^1$ is —N($R^N$)— or —CH($R^C$)—;
$X^2$ is $CR^2$ or N;
$X^3$ is $CR^3$ or N;
$R^N$ is selected from the group consisting of H, $C_{1-6}$ alkyl, and $C_{1-6}$ haloalkyl;
$R^C$ is selected from the group consisting of H, $C_{1-6}$ alkyl, and $C_{1-6}$ haloalkyl;
$L^1$ is a bond or is selected from the group consisting of a $C_{1-6}$ alkylene group, a linking $C_{3-10}$ cycloalkyl group, and a linking 4-10 membered heterocycloalkyl group, wherein the 4-10 membered heterocycloalkyl group is optionally substituted by 1 or 2 independently $C_{1-6}$ alkyl groups;
$L^2$ is a bond or is a $C_{1-6}$ alkylene group;
$R^1$ is selected from the group consisting of $C_{1-6}$ alkyl, $C_{1-6}$ alkoxy, $C_{3-10}$ cycloalkyl, and $C_{6-10}$ aryl, wherein the $C_{3-10}$ cycloalkyl and $C_{6-10}$ aryl are each optionally substituted by 1 or 2 groups independently selected from $C_{1-6}$ alkyl and halo;
$R^2$, $R^3$, $R^4$, and $R^5$ are each independently selected from the group consisting of H, $C_{1-6}$alkyl, halo, and $C_{1-6}$ haloalkyl.

In some embodiments, the compound of Formula I is not a compound selected from the group consisting of:

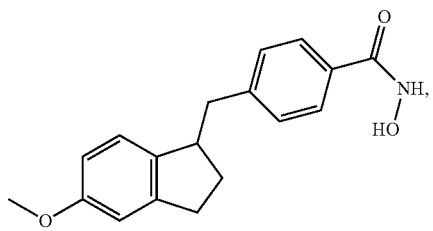

-continued

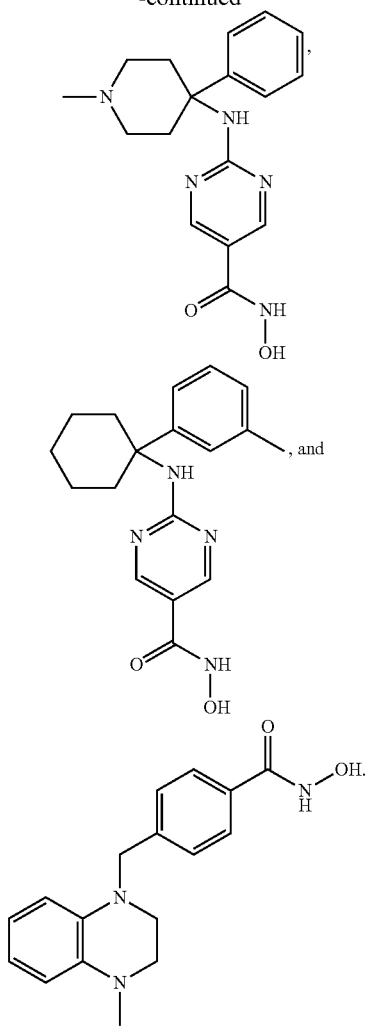

or a pharmaceutically acceptable salt thereof.

In some embodiments:
X$^1$ is —N(R$^N$)— or —CH(R$^C$)—;
X$^2$ is CR$^2$ or N;
X$^3$ is CR$^3$ or N;
R$^N$ is selected from the group consisting of H, C$_{1-6}$ alkyl, and C$_{1-6}$ haloalkyl;
R$^C$ is selected from the group consisting of H, C$_{1-6}$ alkyl, and C$_{1-6}$ haloalkyl;
L$^1$ is a bond or is a C$_{1-6}$ alkylene group;
L$^2$ is a bond or is a C$_{1-6}$ alkylene group;
R$^1$ is selected from the group consisting of C$_{1-6}$ alkyl, C$_{1-6}$ alkoxy, C$_{3-10}$ cycloalkyl, and C$_{6}$-10 aryl, wherein the C$_{3-10}$ cycloalkyl and C$_6$-10 aryl are each optionally substituted by 1 or 2 groups independently selected from C$_{1-6}$ alkyl and halo;
R$^2$, R$^3$, R$^4$, and R$^5$ are each independently selected from the group consisting of H, C$_{1-6}$ alkyl, halo, and C$_{1-6}$ haloalkyl.

In some embodiments:
X$^1$ is —N(R$^N$)— or —CH(R$^C$)—;
X$^2$ is CR$^2$ or N;
X$^3$ is CR$^3$ or N;
R$^N$ is selected from the group consisting of H, C$_{1-6}$ alkyl, and C$_{1-6}$ haloalkyl;
R$^C$ is selected from the group consisting of H, C$_{1-6}$ alkyl, and C$_{1-6}$ haloalkyl;
L$^1$ is a bond or is selected from the group consisting of a C$_{1-6}$ alkylene group, a linking C$_{3-10}$ cycloalkyl group, and a linking 4-10 membered heterocycloalkyl group, wherein the 4-10 membered heterocycloalkyl group is optionally substituted by 1 or 2 independently C$_{1-6}$ alkyl groups;
L$^2$ is a bond or is a C$_{1-6}$ alkylene group;
R$^1$ is selected from the group consisting of C$_{1-6}$ alkyl, C$_{1-6}$ alkoxy, C$_{3-10}$ cycloalkyl, and C$_{6-10}$ aryl, wherein the C$_{3-10}$ cycloalkyl and C$_{6-10}$ aryl are each optionally substituted by 1 or 2 independently selected halo groups;
R$^2$, R$^3$, R$^4$, and R$^5$ are each independently selected from the group consisting of H, halo, and C$_{1-6}$ haloalkyl.

In some embodiments, X$^1$ is —N(R$^N$)—. In some embodiments, R$^N$ is selected from the group consisting of H, C$_{1-3}$ alkyl, and C$_{1-3}$ haloalkyl. In some embodiments, R$^N$ is selected from the group consisting of H and C$_{1-3}$ alkyl. In some embodiments, R$^N$ is selected from the group consisting of H and methyl. In some embodiments, R$^N$ is C$_{1-6}$ alkyl. In some embodiments, R$^N$ is selected from the group consisting of methyl and pentyl (e.g. n-pentyl). In some embodiments, R$^N$ is selected from the group consisting of H, methyl, and pentyl.

In some embodiments, X$^1$ is —CH(R$^C$)—.

In some embodiments, R$^C$ is selected from the group consisting of H, C$_{1-3}$ alkyl, and C$_{1-3}$ haloalkyl. In some embodiments, R$^C$ is selected from the group consisting of H and C$_{1-3}$ alkyl. In some embodiments, R$^C$ is H.

In some embodiments, L$^1$ is a bond. In some embodiments, L$^1$ is selected from the group consisting of a C$_{1-6}$ alkylene group, a linking C$_{3-10}$ cycloalkyl group, and a linking 4-10 membered heterocycloalkyl group, wherein the 4-10 membered heterocycloalkyl group is optionally substituted by 1 or 2 independently C$_{1-6}$ alkyl groups. In some embodiments, L$^1$ is selected from the group consisting of a C$_{1-3}$ alkylene group, a linking C$_{6-10}$ cycloalkyl group, and a linking 4-10 membered heterocycloalkyl group, wherein the 4-10 membered heterocycloalkyl group is optionally substituted by 1 or 2 independently C$_{1-3}$ alkyl groups.

In some embodiments, L$^1$ is a C$_{1-6}$ alkylene group. In some embodiments, L$^1$ is a C$_{1-3}$ alkylene group. In some embodiments, L$^1$ is selected from the group consisting of methylene and propylene (e.g., —CH$_2$CH(CH$_3$)— or —CH(CH$_2$CH$_3$)—).

In some embodiments, L$^1$ is selected from the group consisting of methylene, propylene,

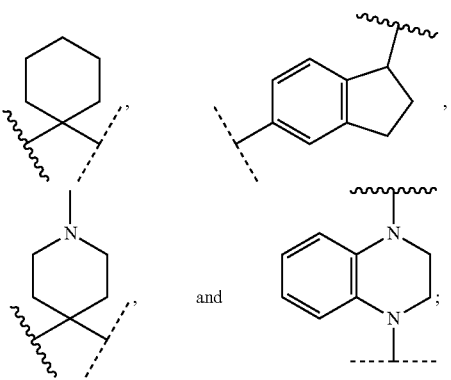

wherein:
  ⌇⌇⌇ indicates the bond between $L^1$ and $X^1$; and
  ---- indicates the bond between $L^1$ and $R^1$.
In some embodiments, $L^1$ is selected from the group consisting of methylene,

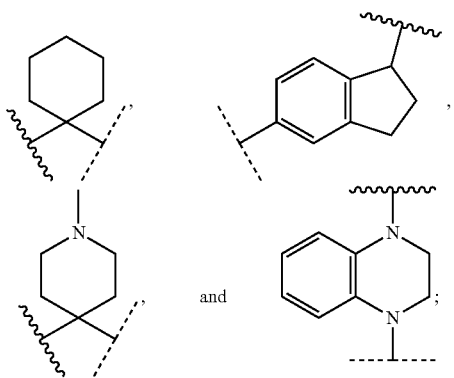

wherein:
  ⌇⌇⌇ indicates the bond between $L^1$ and $X^1$; and
  ---- indicates the bond between $L^1$ and $R^1$.

In some embodiments, $L^2$ is a bond. In some embodiments, $L^2$ is a $C_{1-3}$ alkylene group. In some embodiments, $L^2$ is methylene.

In some embodiments, $R^1$ is selected from the group consisting of $C_{1-3}$ alkyl, $C_{1-3}$ alkoxy, $C_{6-10}$ cycloalkyl, and phenyl, wherein the $C_{6-10}$ cycloalkyl and phenyl are optionally substituted by 1 or 2 groups independently selected from $C_{1-3}$ alkyl and halo. In some embodiments, $R^1$ is selected from the group consisting of $C_{1-3}$ alkyl, $C_{1-3}$ alkoxy, $C_{6-10}$ cycloalkyl, and phenyl, wherein the $C_{6-10}$ cycloalkyl and phenyl are optionally substituted by 1 or 2 groups independently selected from methyl and fluoro. In some embodiments, $R^1$ is selected from the group consisting of $C_{1-3}$ alkyl, $C_{1-3}$ alkoxy, $C_{6-10}$ cycloalkyl, and phenyl, wherein the phenyl is optionally substituted by 1 or 2 independently selected halo groups. In some embodiments, $R^1$ is selected from the group consisting of $C_{1-3}$ alkyl, $C_{1-3}$ alkoxy, $C_{6-10}$ cycloalkyl, and phenyl, wherein the phenyl is optionally substituted by 1 or 2 fluoro groups.

In some embodiments, $R^1$ is selected from the group consisting of $C_{6-10}$ cycloalkyl and phenyl, wherein the $C_{6-10}$ cycloalkyl and phenyl are each optionally substituted by 1 or 2 groups independently selected from the group consisting of $C_{1-6}$ alkyl and halo. In some embodiments, $R^1$ is selected from the group consisting of $C_{6-10}$ cycloalkyl and phenyl, wherein the $C_{6-10}$ cycloalkyl and phenyl are each optionally substituted by 1 or 2 groups independently selected from the group consisting of $C_{1-3}$ alkyl and fluoro. In some embodiments, $R^1$ is $C_{6-10}$ cycloalkyl, which is optionally substituted by 1 or 2 groups independently selected $C_{1-6}$ alkyl groups. In some embodiments, $R^1$ is $C_{6-10}$ cycloalkyl, which is optionally substituted by 1 or 2 groups independently selected CL-3 alkyl groups.

In some embodiments, $R^1$ is selected from the group consisting of methyl, methoxy, cyclohexyl, adamantyl, norbornyl, phenyl, 6,6-dimethylbicyclo[3.1.1]heptanyl (e.g., 6,6-dimethylbicyclo[3.1.1]heptan-3-yl), and 3-fluorophenyl. In some embodiments, $R^1$ is selected from the group consisting of methyl, methoxy, cyclohexyl, adamantyl, norbornyl, phenyl, and 3-fluorophenyl. In some embodiments, $R^1$ is adamantyl or 6,6-dimethylbicyclo[3.1.1]heptanyl (e.g., 6,6-dimethylbicyclo[3.1.1]heptan-3-yl). In some embodiments, $R^1$ is adamantyl. In some embodiments, $R^1$ is 6,6-dimethylbicyclo[3.1.1]heptanyl (e.g., 6,6-dimethylbicyclo[3.1.1]heptan-3-yl).

In some embodiments, $X^2$ is N.
In some embodiments, $X^2$ is $CR^2$.
In some embodiments, $R^2$ is H or F. In some embodiments, $R^2$ is F. In some embodiments, $R^2$ is H. In some embodiments, $R^2$ is selected from the group consisting of H, $C_{1-6}$ alkyl, and halo. In some embodiments, $R^2$ is selected from the group consisting of H, methyl, F, Cl, and Br. In some embodiments, $R^2$ is selected from the group consisting of H, methyl, and F.

In some embodiments, $X^3$ is N.
In some embodiments, $X^3$ is $CR^3$.
In some embodiments, $R^3$ is H or F. In some embodiments, $R^3$ is H. In some embodiments, $R^3$ is selected from the group consisting of H, $C_{1-6}$ alkyl, and halo. In some embodiments, $R^3$ is selected from the group consisting of H, methyl, F, Cl, and Br. In some embodiments, $R^3$ is selected from the group consisting of H, methyl, and F.

In some embodiments, $X^2$ and $X^3$ are each N.
In some embodiments, $X^2$ is $CR^2$ and $X^3$ is $CR^3$.
In some embodiments, $X^2$ is N and $X^3$ is $CR^3$.
In some embodiments, $X^2$ is $CR^2$ and $X^3$ is N.

In some embodiments, $R^2$ is F and $R^3$ is H. In some embodiments, $R^2$ and $R^3$ are each H. In some embodiments, $R^2$ and $R^3$ are each halo. In some embodiments, $R^2$ and $R^3$ are each F.

In some embodiments, $R^4$ is selected from the group consisting of H, halo, and $C_{1-3}$ fluoroalkyl. In some embodiments, $R^4$ is selected from the group consisting of H, F, and $CF_3$. In some embodiments, $R^4$ is H.

In some embodiments, $R^5$ is selected from the group consisting of H, halo, and $C_{1-3}$ fluoroalkyl. In some embodiments, $R^5$ is selected from the group consisting of H, F, and $CF_3$. In some embodiments, $R^5$ is H.

In some embodiments, at least one of $R^2$, $R^3$, $R^4$, and $R^5$ is a $C_{1-6}$ alkyl, halo, or $C_{1-6}$ haloalkyl group. In some embodiments, at least one of $R^2$, $R^3$, $R^4$, and $R^5$ is a halo or $C_{1-6}$ haloalkyl group. In some embodiments, at least one of $R^2$, $R^3$, $R^4$, and $R^5$ is a halo group. In some embodiments, at least one of $R^2$, $R^3$, $R^4$, and $R^5$ is a $C_{1-6}$alkyl group. In some embodiments, at least one of $R^2$, $R^3$, $R^4$, and $R^5$ is F. In some embodiments, at least one of $R^2$, $R^3$, $R^4$, and $R^5$ is methyl. In some embodiments, one of $R^2$, $R^3$, $R^4$, and $R^5$ is F and the other variables are each H. In some embodiments, one of $R^2$, $R^3$, $R^4$, and $R^5$ is methyl and the other variables are each H. In some embodiments, one of $R^2$, $R^3$, $R^4$, and R is $^{18}F$ and the other variables are each H. In some embodiments, $R^2$ is F and $R^3$, $R^4$, and $R^5$ are each H.

In some embodiments:
  $X^1$ is —N($R^N$)— or —$CH_2$—;
  $X^2$ is $CR^2$ or N;
  $X^3$ is $CR^3$ or N;
  $R^N$ is selected from the group consisting of H and $C_{1-6}$ alkyl;
  $L^1$ is a bond or selected from the group consisting of a $C_{1-3}$ alkylene group, a linking $C_{6-10}$ cycloalkyl group, and a linking 4-10 membered heterocycloalkyl group, wherein the 4-10 membered heterocycloalkyl group is optionally substituted by 1 or 2 independently $C_{1-3}$ alkyl groups;
  $L^2$ is a bond or methylene;
  $R^1$ is selected from the group consisting of $C_{1-3}$ alkyl, $C_{1-3}$ alkoxy, $C_{6-10}$ cycloalkyl, and phenyl, wherein the $C_{6-10}$ cycloalkyl and phenyl are optionally substituted by 1 or 2 groups independently selected from $C_{1-3}$ alkyl and halo;

$R^2$ is selected from the group consisting of H, $C_{1-6}$ alkyl, and halo; and $R^3$, $R^4$, and $R^5$ are each H.

In some embodiments:

$X^1$ is —N($R^N$)— or —CH$_2$—;
$X^2$ is $CR^2$ or N;
$X^3$ is $CR^3$ or N;
$R^N$ is selected from the group consisting of H and methyl;
$L^1$ is a bond or selected from the group consisting of a $C_{1-3}$ alkylene group, a linking $C_{6-10}$ cycloalkyl group, and a linking 4-10 membered heterocycloalkyl group, wherein the 4-10 membered heterocycloalkyl group is optionally substituted by 1 or 2 independently $C_{1-3}$ alkyl groups;
$L^2$ is a bond or methylene;
$R^1$ is selected from the group consisting of $C_{1-3}$ alkyl, $C_{1-3}$ alkoxy, $C_{6-10}$ cycloalkyl, and phenyl, wherein the phenyl is optionally substituted by 1 or 2 independently selected halo groups;
$R^2$ is selected from the group consisting of H and halo; and
$R^3$, $R^4$, and $R^5$ are each H.

In some embodiments:

$X^1$ is —N($R^N$)— or —CH$_2$—;
$X^2$ is $CR^2$ or N;
$X^3$ is $CR^3$ or N;
$R^N$ is selected from the group consisting of H and $C_{1-6}$ alkyl;
$L^1$ is a bond or is selected from the group consisting of methylene, propylene,

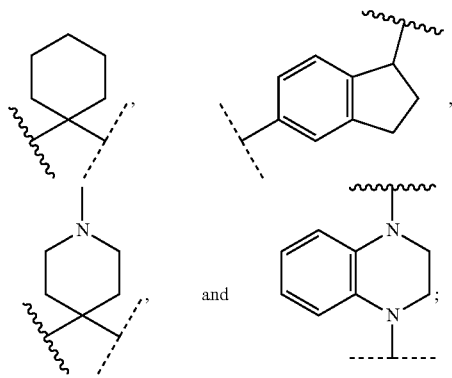

wherein:
 ∿∿ indicates the bond between $L^1$ and $X^1$; and
 ---- indicates the bond between $L^1$ and $R^1$;
$L^2$ is a bond or methylene;
$R^1$ is selected from the group consisting of $C_{1-3}$ alkyl, $C_{1-3}$ alkoxy, $C_{6-10}$ cycloalkyl, and phenyl, wherein the $C_{6-10}$ cycloalkyl and phenyl are optionally substituted by 1 or 2 groups independently selected from $C_{1-6}$ alkyl and halo;
$R^2$ is selected from the group consisting of H, $C_{1-6}$ alkyl, and halo; and
$R^3$, $R^4$, and $R^5$ are each H.

In some embodiments:

$X^1$ is —N($R^N$)— or —CH$_2$—;
$X^2$ is $CR^2$ or N;
$X^3$ is $CR^3$ or N;
$R^N$ is selected from the group consisting of H and methyl;
$L^1$ is a bond or is selected from the group consisting of methylene,

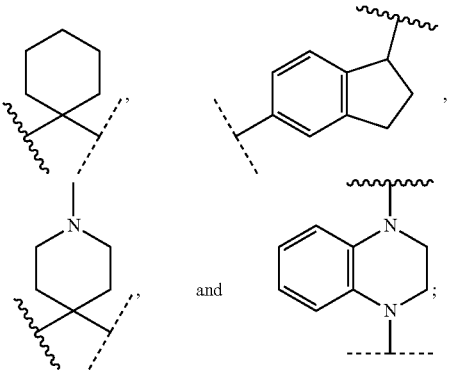

wherein:
 ∿∿ indicates the bond between $L^1$ and $X^1$; and
 ---- indicates the bond between $L^1$ and $R^1$;
$L^2$ is a bond or methylene;
$R^1$ is selected from the group consisting of $C_{1-3}$ alkyl, $C_{1-3}$ alkoxy, $C_{6-10}$ cycloalkyl, and phenyl, wherein the phenyl is optionally substituted by 1 or 2 independently selected halo groups;
$R^2$ is selected from the group consisting of H and halo; and
$R^3$, $R^4$, and $R^5$ are each H.

In some embodiments:

$X^1$ is —N($R^N$)— or —CH$_2$—;
$X^2$ is $CR^2$ or N;
$X^3$ is $CR^3$ or N;
$R^N$ is selected from the group consisting of H and methyl;
$L^1$ is a bond or is selected from the group consisting of methylene,

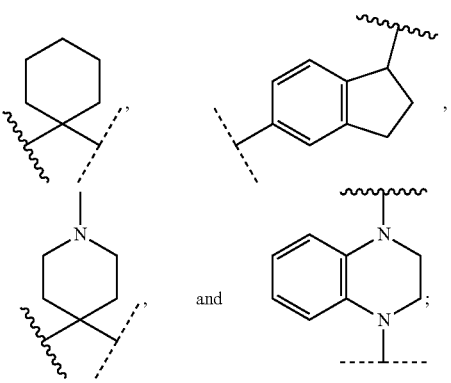

wherein:
 ∿∿ indicates the bond between $L^1$ and $X^1$; and
 ---- indicates the bond between $L^1$ and $R^1$;
$L^2$ is a bond or methylene;
$R^1$ is selected from the group consisting of methyl, methoxy, cyclohexyl, adamantyl, norbornyl, phenyl, and 3-fluorophenyl;
$R^2$ is selected from the group consisting of H and halo; and
$R^3$, $R^4$, and $R^5$ are each H.

In some embodiments:
$X^1$ is —N($R^N$)—;
$X^2$ is $CR^2$;
$X^3$ is $CR^3$;
$R^N$ is $C_{1-3}$ alkyl;
$L^1$ and $L^2$ are each an independently selected $C_{1-3}$ alkylene group;
$R^1$ is a $C_{6-10}$ cycloalkyl group;
$R^2$ and $R^3$ are each independently selected from the group consisting of H and halo; and
$R^4$ and $R^5$ are each H.

In some embodiments:
$X^1$ is —N($R^N$)—;
$X^2$ is $CR^2$;
$X^3$ is $CR^3$;
$R^N$ is $C_{1-3}$ alkyl;
$L^1$ and $L^2$ are each an independently selected $C_{1-3}$ alkylene group;
$R^1$ is adamantyl or 6,6-dimethylbicyclo[3.1.1]heptanyl (e.g., 6,6-dimethylbicyclo[3.1.1]heptan-3-yl);
$R^2$ and $R^3$ are each independently selected from the group consisting of H and halo; and
$R^4$ and $R^5$ are each H.

In some embodiments:
$X^1$ is —N($R^N$)— or —$CH_2$—;
$X^2$ is $CR^2$ or N;
$X^3$ is $CR^3$ or N;
$R^N$ is selected from the group consisting of H and methyl;
$L^1$ is a bond or a $C_{1-3}$ alkylene group;
$L^2$ is a bond or methylene;
$R^1$ is selected from the group consisting of $C_{6-10}$ cycloalkyl and phenyl, wherein the $C_{6-10}$ cycloalkyl and phenyl are each optionally substituted by 1 or 2 groups independently selected from $C_{1-3}$ alkyl and halo;
$R^2$ is selected from the group consisting of H and halo;
$R^3$, $R^4$, and $R^5$ are each H.

In some embodiments:
$X^1$ is —N($R^N$)— or —$CH_2$—;
$X^2$ is $CR^2$ or N;
$X^3$ is $CR^3$ or N;
$R^N$ is selected from the group consisting of H and methyl;
$L^1$ is a bond or is selected from the group consisting of methylene and propylene, $L^2$ is a bond or methylene;
$R^1$ is selected from the group consisting of $C_{6-10}$ cycloalkyl and phenyl, wherein the $C_{6-10}$ cycloalkyl and phenyl are each optionally substituted by 1 or 2 groups independently selected from $C_{1-3}$ alkyl and halo;
$R^2$ is selected from the group consisting of H and halo;
$R^3$, $R^4$, and $R^5$ are each H.

In some embodiments, the compound of Formula I is a compound of Formula II:

II or a pharmaceutically acceptable salt thereof, wherein variables $R^1$, $X^1$, $X^2$, and $X^3$ are defined according to the definitions provided herein for compounds of Formula I.

In some embodiments, the compound of Formula I is a compound of Formula III:

III or a pharmaceutically acceptable salt thereof, wherein variables $R^1$, $L^1$, $X^1$, $X^2$, and $X^3$ are defined according to the definitions provided herein for compounds of Formula I.

In some embodiments, the compound of Formula I is a compound of Formula IV:

IV or a pharmaceutically acceptable salt thereof, wherein variables $R^1$, $R^N$, $X^2$, and $X^3$ are defined according to the definitions provided herein for compounds of Formula I.

In some embodiments, the compound of Formula I is a compound of Formula V:

V or a pharmaceutically acceptable salt thereof, wherein variables $R^1$ and $R^N$ are defined according to the definitions provided herein for compounds of Formula I.

Unless specifically defined, compounds and salts provided herein can also include all isotopes of atoms occurring in the intermediates or final compounds. Isotopes include those atoms having the same atomic number but different mass numbers.

In some embodiments, a compound provided herein (e.g., a compound of any of Formulas I-V) or pharmaceutically acceptable salt thereof, comprises at least one radioisotope. As used herein, the term "radioisotope" refers to an atom having an atomic mass or mass number different from the atomic mass or mass number typically found in nature (i.e., naturally occurring). A "radiolabeled" compound is a compound provided herein where one or more atoms are replaced or substituted by an atom having an atomic mass or mass number different from the atomic mass or mass number typically found in nature (i.e., naturally occurring). Example radioisotopes include, but are not limited to, $^{11}C$, $^{13}N$, $^{15}O$, $^{18}F$, $^{34m}Cl$, $^{38}K$, $^{45}Ti$, $^{51}Mn$, $^{52m}Mn$ $^{52}Fe$, $^{55}Co$, $^{60}Cu$, $^{61}Cu$, $^{62}Cu$, $^{64}Cu$, $^{66}Ga$, $^{67}Ga$, $^{68}Ga$, $^{71}As$, $^{72}As$, $^{74}As$, $^{75}Br$, $^{76}Br$, $^{82}Rb$, $^{86}Y$, $^{89}Zr$, $^{90}Nb$, $^{94m}Tc$, $^{99m}Tc$, $^{110m}In$, $^{111}In$, $^{118}Sb$, $^{120}I$, $^{121}I$, $^{122}I$, $^{123}I$, $^{124}I$, $^{124}I$, $^{131}I$, and $^{201}Tl$.

In some embodiments, the radioisotope is a positron emitter. As used herein the term "positron emitter" refers to a radioisotope wherein a proton is converted to a neutron, thereby releasing a positron and an electron neutrino. In some embodiments, the positron emitter is $^{11}C$ or $^{18}F$.

In some embodiments, the compound or pharmaceutically acceptable salt provided herein comprises at least one radioisotope selected from the group consisting of $^{11}C$ and $^{18}F$. In some embodiments, the compound or pharmaceutically acceptable salt comprises at least one $^{18}F$ radioisotope. In some embodiments, at least one halo group of a compound provided herein is a radioisotope. In some embodiments at least one halo group of a compound provided herein is $^{18}F$. In some embodiments, at least one haloalkyl or fluoroalkyl group of a compound provided herein comprises at least one radioisotope.

In some embodiments, at least one haloalkyl or fluoroalkyl group of a compound provided herein comprises at least one $^{18}F$ radioisotope.

In some embodiments, $R^N$ comprises at least one radioisotope. In some embodiments, $R^N$ comprises one radioisotope. In some embodiments, $R^N$ comprises one $^{18}F$ radioisotope.

In some embodiments, $R^C$ comprises at least one radioisotope. In some embodiments, $R^C$ comprises one radioisotope. In some embodiments, $R^C$ comprises one $^{18}F$ radioisotope.

In some embodiments, $R^1$ comprises at least one radioisotope. In some embodiments, $R^1$ comprises one radioisotope. In some embodiments, $R^1$ comprises one $^{18}F$ radioisotope.

In some embodiments, $R^2$ comprises at least one radioisotope. In some embodiments, $R^2$ comprises one radioisotope. In some embodiments, $R^2$ comprises one $^{18}F$ radioisotope.

In some embodiments, $R^3$ comprises at least one radioisotope. In some embodiments, $R^3$ comprises one radioisotope. In some embodiments, $R^3$ comprises one $^{18}F$ radioisotope.

In some embodiments, $R^4$ comprises at least one radioisotope. In some embodiments, $R^4$ comprises one radioisotope. In some embodiments, $R^4$ comprises one $^{18}F$ radioisotope.

In some embodiments, $R^5$ comprises at least one radioisotope. In some embodiments, $R^5$ comprises one radioisotope. In some embodiments, $R^5$ comprises one $^{18}F$ radioisotope.

In some embodiments, the compound of Formula I is a compound of Formula VI:

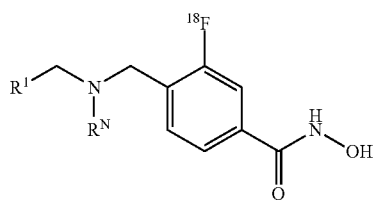

VI or a pharmaceutically acceptable salt thereof, wherein variables $R^1$ and $R^N$ are defined according to the definitions provided herein for compounds of Formula I.

Unless otherwise stated, when an atom is designated as an isotope or radioisotope (e.g., deuterium, $^{11}C$, $^{18}F$), the atom is understood to comprise the isotope or radioisotope in an amount at least greater than the natural abundance of the isotope or radioisotope.

For example, when an atom is designated as "D" or "deuterium", the position is understood to have deuterium at an abundance that is at least 3000 times greater than the natural abundance of deuterium, which is 0.015% (i.e., at least 45% incorporation of deuterium).

As used herein, the term "Ci", refers to "Curie", a unit of radioactivity.

As used herein, the term "specific activity" refers to the activity of a given radioisotope per unit mass, for example, Ci/g.

In some embodiments, the compound of Formula I is a compound selected from the group consisting of:

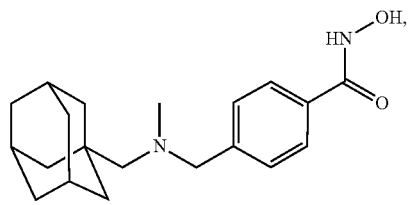

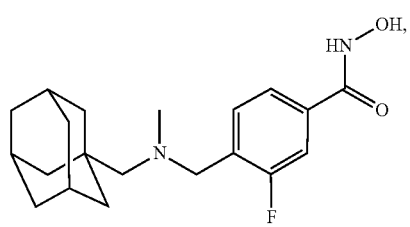

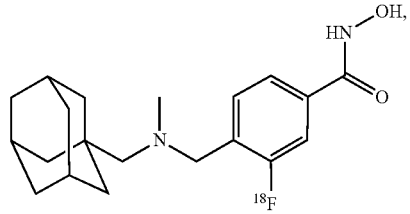

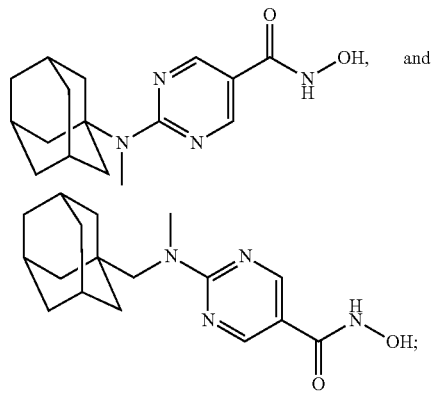

or a pharmaceutically acceptable salt thereof.

In some embodiments, the compound of Formula I is a compound selected from the group consisting of:
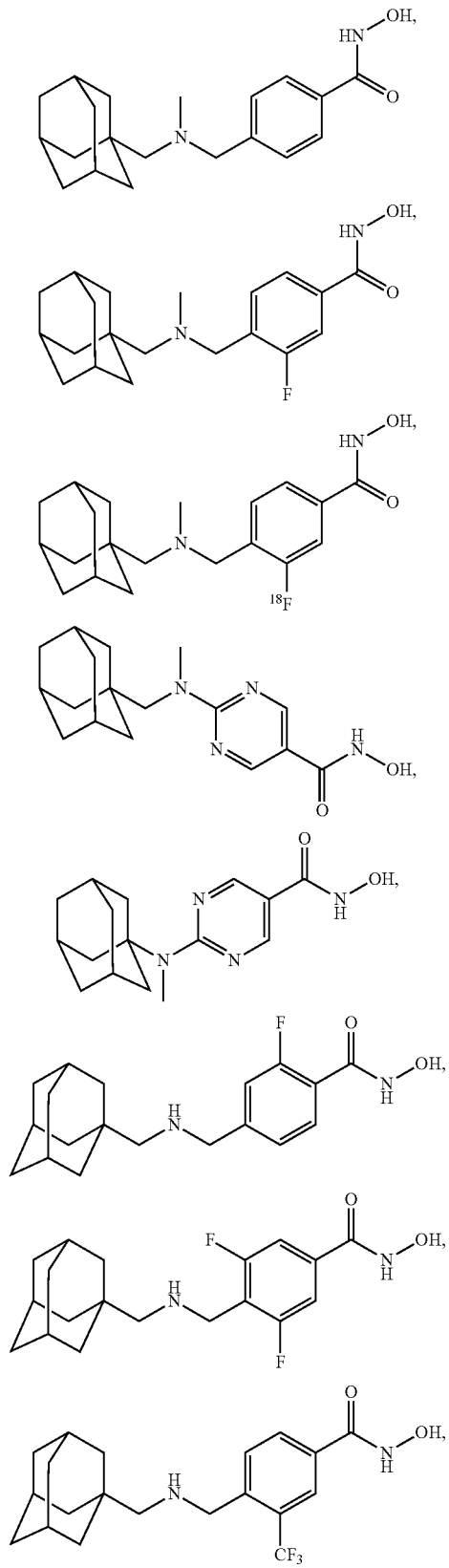
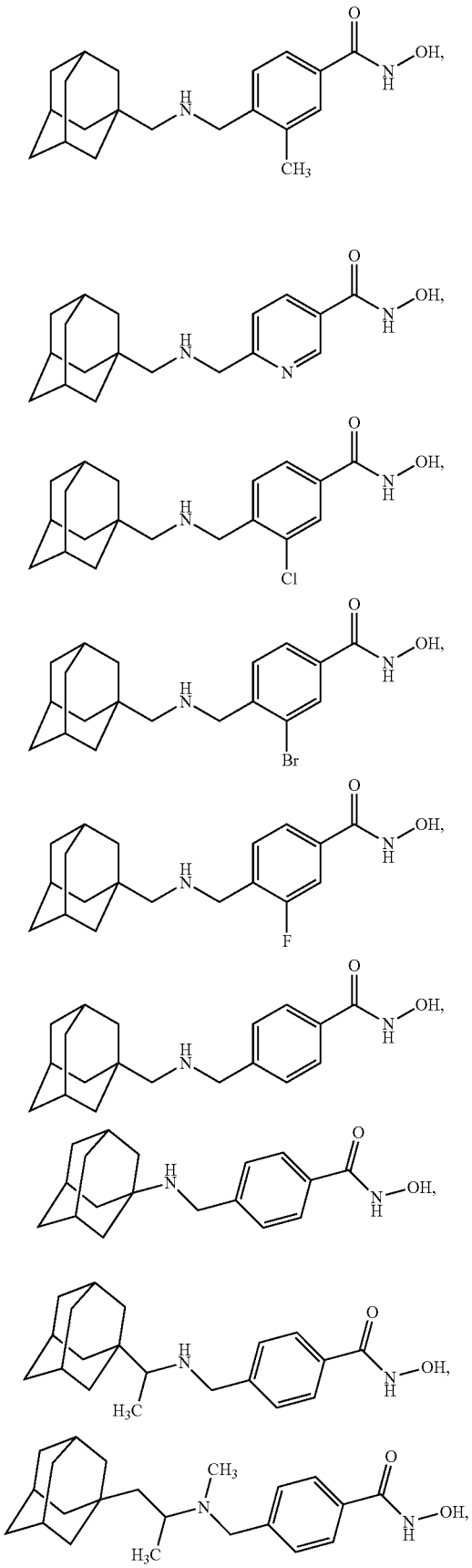

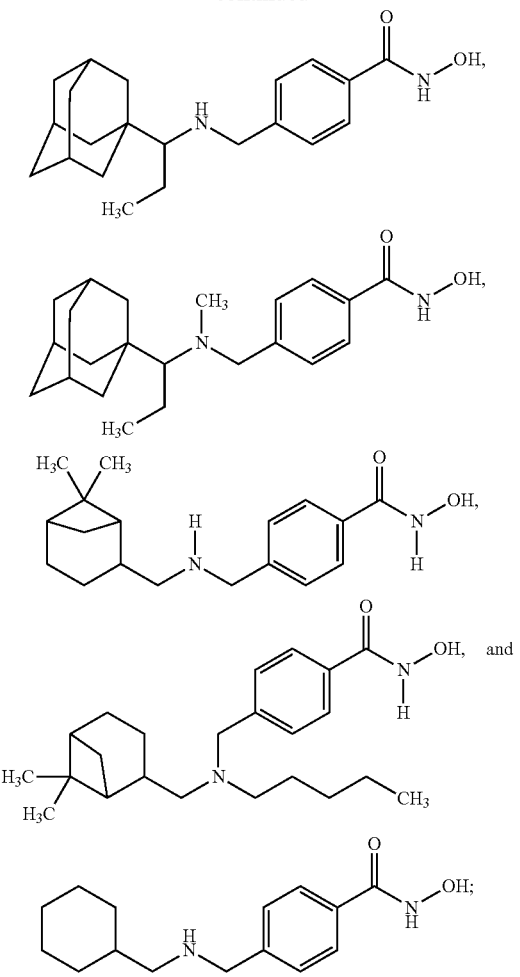
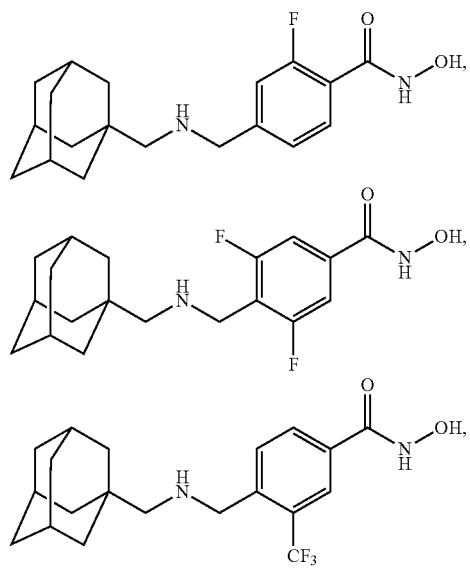
or a pharmaceutically acceptable salt thereof.
In some embodiments, the compound of Formula I is a compound selected from the group consisting of:
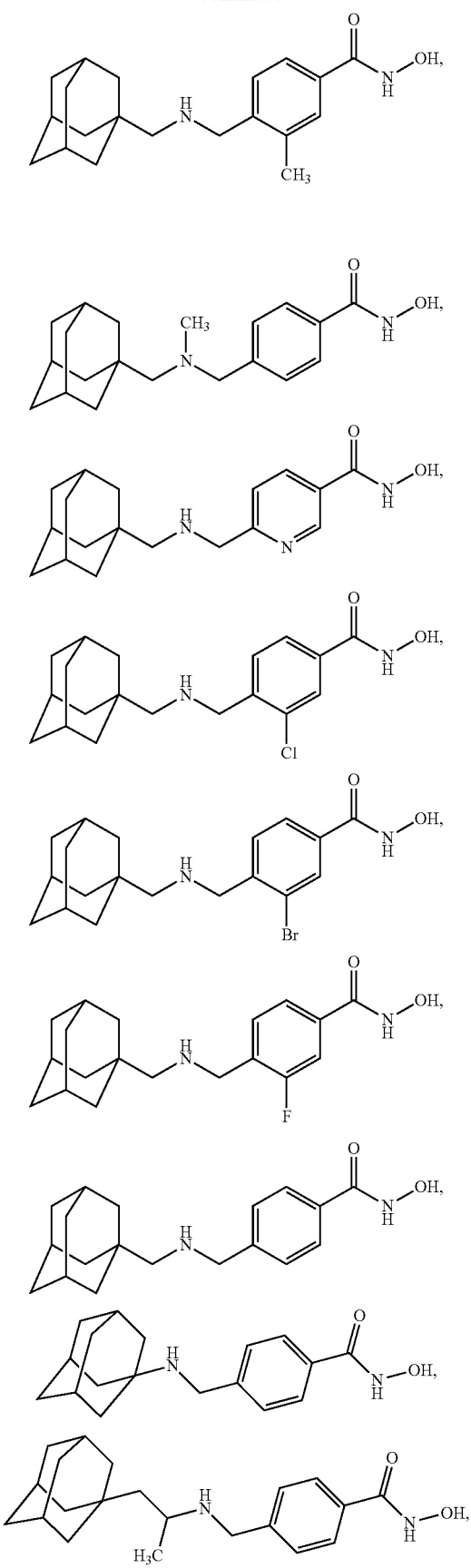

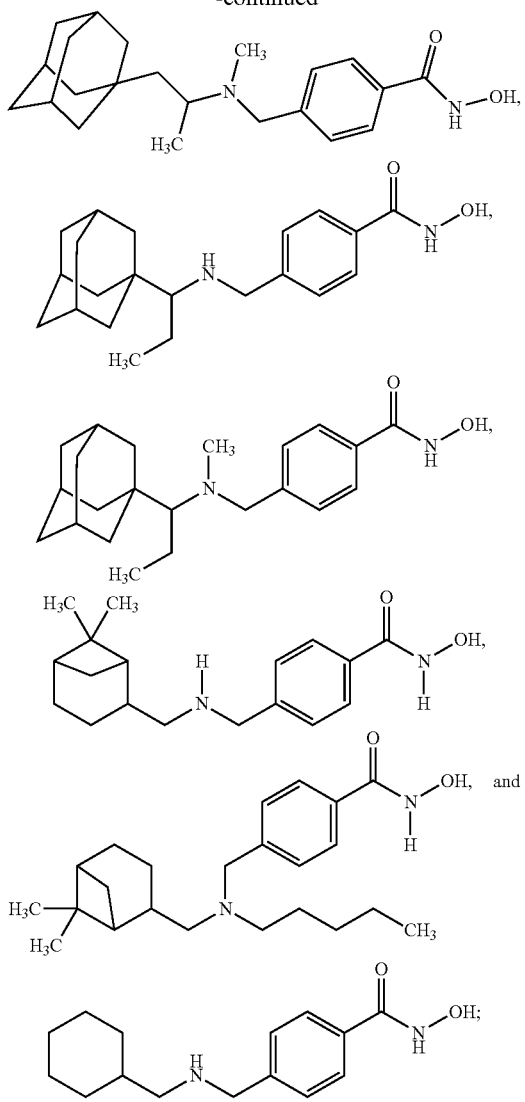

or a pharmaceutically acceptable salt thereof.

In some embodiments, the compound of Formula I is selected from the group consisting of:

or a pharmaceutically acceptable salt thereof.

Synthesis

As will be appreciated, the compounds provided herein, including salts thereof, can be prepared using known organic synthesis techniques and can be synthesized according to any of numerous possible synthetic routes.

The compounds provided herein can be prepared, for example, according to the representative procedure shown in Scheme 1. For example, using an air-stable Ruthenium-complex, an $\eta^6$-coordinated phenol precursor was prepared and used without further purification as an eluent to elute [$^{18}$F]fluoride from an anion exchange cartridge.

The labeling typically proceeded with high conversion (>70% by TLC). Subsequent transacylation in the same pot afforded the final radiolabeled product (e.g., Example 2).

Scheme 1.

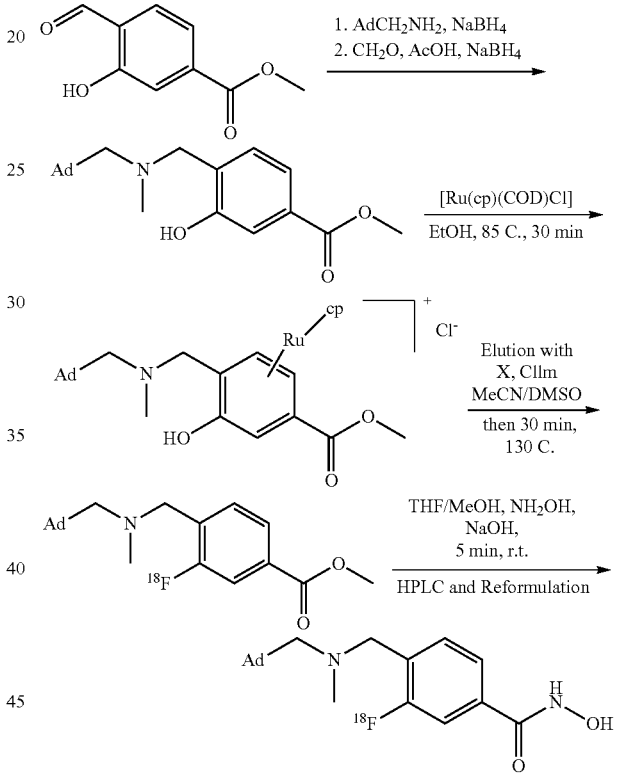

Additional synthetic methods for incorporating radioisotopes into organic compounds are well known in the art, and one of ordinary skill in the art will readily recognize other methods applicable for preparing the radiolabeled compounds and salts provided herein.

It will be appreciated by one skilled in the art that the processes described are not the exclusive means by which compounds provided herein may be synthesized and that a broad repertoire of synthetic organic reactions is available to be potentially employed in synthesizing compounds provided herein. The person skilled in the art knows how to select and implement appropriate synthetic routes. Suitable synthetic methods of starting materials, intermediates and products may be identified by reference to the literature, including reference sources such as: *Advances in Heterocyclic Chemistry, Vols.* 1-107 (Elsevier, 1963-2012); *Journal of Heterocyclic Chemistry Vols.* 1-49 (*Journal of* Heterocyclic Chemistry, 1964-2012); Carreira, et al. (Ed.) *Science of*

*Synthesis, Vols.* 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (*Elsevier,* $2^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry*: Reactions, *Mechanisms, and Structure,* $6^{th}$ Ed. (Wiley, 2007); Trost et al. (Ed.), *Comprehensive Organic Synthesis* (Pergamon Press, 1991).

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis,* $3^{rd}$ Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

At various places in the present specification, divalent linking substituents are described. It is specifically intended that each divalent linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups.

As used herein, the phrase "optionally substituted" means unsubstituted or substituted. As used herein, the term "substituted" means that a hydrogen atom is removed and replaced by a substituent. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkylene" refers to a divalent alkyl linking group having n to m carbons. Examples of alkylene groups include, but are not limited to, methylene, ethan-1,2-diyl, propan-1,3-diyl, propan-1,2-diyl, and the like. In some embodiments, the alkylene moiety contains 1 to 6, 1 to 3, or 1 to 2 carbon atoms.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, the term "$C_{n-m}$ alkoxy", employed alone or in combination with other terms, refers to a group of formula —O-alkyl, wherein the alkyl group has n to m carbons. Example alkoxy groups include methoxy, ethoxy, propoxy (e.g., n-propoxy and isopropoxy), tert-butoxy, and the like. In some embodiments, the alkyl group has 1 to 6, 1 to 4, or 1 to 3 carbon atoms.

As used herein, "halo" refers to F, Cl, Br, or I. In some embodiments, the halo is F, Cl, or Br. In some embodiments, the halo is F. In some embodiments, the halo is $^{18}$F.

As used herein, the term "$C_{n-m}$ haloalkyl" refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only (e.g., a $C_{1-6}$ fluoroalkyl group). In some embodiments, the alkyl group has 1 to 6, 1 to 4, or 1 to 3 carbon atoms. In some embodiments, the haloalkyl group comprises one or more $^{18}$F radioisotopes. In some embodiments, the haloalkyl group comprises one $^{18}$F radioisotope.

As used herein, the term "aryl" refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups have from 6 to about 20 carbon atoms, from 6 to about 15 carbon atoms, or from 6 to about 10 carbon atoms. In some embodiments, the aryl group is a substituted or unsubstituted phenyl.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Cycloalkyl groups can have 3, 4, 5, 6, 7, 8, 9, or 10 ring-forming carbons (i.e., a $C_{3-10}$ cycloalkyl group). Ring-forming carbon atoms of a cycloalkyl group can be optionally substituted by oxo or sulfido (e.g., C(=O) or C(=S)). Example cycloalkyl groups include, but are not limited to, cyclopropyl, cyclobutyl, cyclopentyl, cyclohexyl, cycloheptyl, cyclopentenyl, cyclohexenyl, cyclohexadienyl, cycloheptatrienyl, norbornyl, adamantly, and the like. In some embodiments, the cycloalkyl is selected from the group consisting of cyclopropyl, cyclobutyl, cyclopentyl, cyclohexyl, cycloheptyl, cyclooctyl, cyclononyl, and adamantyl. In some embodiments, the cycloalkyl has 6-10 ring-forming carbon atoms (i.e., a $C_{6-10}$ cycloalkyl group). In some embodiments, the cycloalkyl has 3-6 ring-forming carbon atoms (i.e., a $C_{3-6}$ cycloalkyl group). In some embodiments, the cycloalkyl group is an adamantyl group.

As used herein, the term "linking cycloalkyl" refers to a divalent cycloalkyl linking group. A linking cycloalkyl group can include mono- or polycyclic (e.g., having 2, 3 or 4 fused rings) groups and spirocycles. Cycloalkyl groups can have 3, 4, 5, 6, 7, 8, 9, or 10 ring-forming carbons (i.e., a $C_{3-10}$ cycloalkyl group). Also included in the definition of cycloalkyl are moieties that have one or more aromatic rings fused (i.e., having a bond in common with) to the cycloalkyl ring, for example, benzo derivatives of cyclopentane, cyclohexane, and the like. Exemplary linking cycloalkyl groups include, but are not limited to, 1,3-cyclobutylene, 1,4-cyclohexylene, 1,3-cyclohexylene, 1,1-cyclohexylene, and the like. Exemplary polycyclic linking cycloalkyl groups include, but are not limited to:

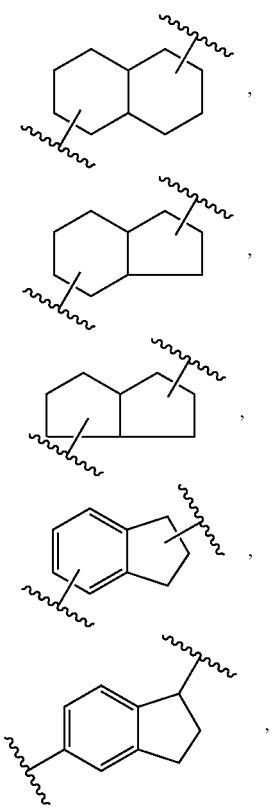

1,4-piperidinylene, 4,4-piperidinylene, 1,3-azetidinylene, and benzo fused heterocycloalkyl groups such as:

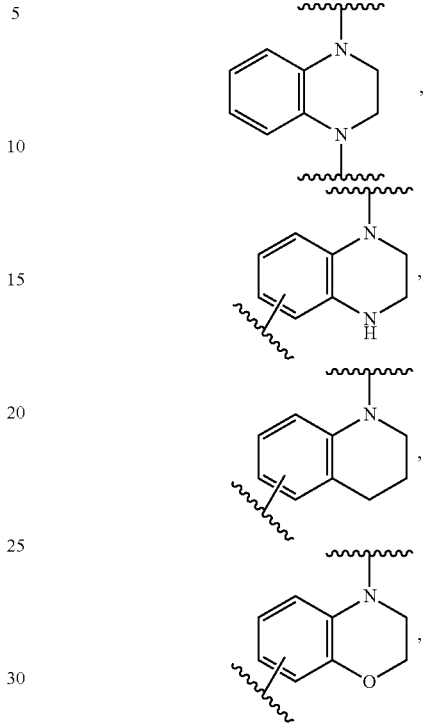

and the like.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, and 7-membered heterocycloalkyl groups. Heterocycloalkyl groups can also include spirocycles. Example heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo (=O). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl has 4-10, 4-7, or 4-6 ring atoms with 1 or 2 heteroatoms independently selected from nitrogen, oxygen, or sulfur.

As used herein, the term "linking heterocycloalkyl" refers to a divalent heterocyclic linking group. Exemplary divalent heterocycloalkyl groups include, but are not limited to, and the like. In some embodiments, the linking heterocycloalkyl has 4-10, 4-7, or 4-6 ring atoms with 1 or 2 heteroatoms independently selected from nitrogen, oxygen, or sulfur.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone—enol pairs, amide—imidic acid pairs, lactam—lactim pairs, enamine—imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 11H- and 2H-pyrazole. Tautomeric forms can be in equilibrium or sterically locked into one form by appropriate substitution.

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

Example acids can be inorganic or organic acids and include, but are not limited to, strong and weak acids. Some example acids include hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Some weak acids include, but are not limited to acetic acid, propionic acid, butanoic acid, benzoic acid, tartaric acid, pentanoic acid, hexanoic acid, heptanoic acid, octanoic acid, nonanoic acid, and decanoic acid.

Example bases include lithium hydroxide, sodium hydroxide, potassium hydroxide, lithium carbonate, sodium carbonate, potassium carbonate, and sodium bicarbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, tert-butyl, trimethylsilyl and cyclohexyl substituted amides.

In some embodiments, the compounds and salts provided herein are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present application include the conventional non-toxic salts of the parent compound formed, for example, from non-toxic inorganic or organic acids. The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977). Conventional methods for preparing salt forms are described, for example, in *Handbook of Pharmaceutical Salts: Properties, Selection, and Use*, Wiley-VCH, 2002.

Methods of Use

The present application further provides a method of inhibiting an activity of a histone deacetylase (HDAC) enzyme in a cell sample, a tissue sample, or a subject. In some embodiments, the method is an in vitro method. In some embodiments, the method is an in vivo method. In some embodiments, the method comprises contacting a cell or tissue (e.g., a cell sample or a tissue sample) having an HDAC enzyme with a compound provided herein (e.g. a compound of any of Formulas I-VI), or a pharmaceutically acceptable salt thereof. In some embodiments, the method comprises administering to a subject a compound provided herein, or a pharmaceutically acceptable salt thereof. In some embodiments, inhibiting an activity of a histone deacetylase (HDAC) enzyme comprises deregulating the histone deacetylase (HDAC) enzyme.

In some embodiments, the HDAC enzyme is a class IIb HDAC enzyme. In some embodiments, the histone deacetylase (HDAC) enzyme is HDAC6.

As used herein, the term "subject," refers to any animal, including mammals. Example subjects include, but are not limited to, mice, rats, rabbits, dogs, cats, swine, cattle, sheep, horses, primates, and humans. In some embodiments, the subject is a human. In some embodiments, the method comprises administering to the subject a therapeutically effective amount of a compound provided herein (e.g., a compound of any of Formulas I-VI), or a pharmaceutically acceptable salt thereof.

The compounds provided herein can be selective HDAC inhibitors. As used, the term "selective" means that the compound binds to or inhibits a particular enzyme with greater affinity or potency, respectively, as compared to at least one other enzyme. In some embodiments, selectivity comprises about 2-fold to about 1000-fold selectivity for a particular enzyme as compared to at least one other enzyme, for example, about 2-fold to about 1000-fold, about 2-fold to about 500-fold, about 2-fold to about 100-fold, about 2-fold to about 50-fold, about 2-fold to about 20-fold, about 2-fold to about 10-fold, about 10-fold to about 1000-fold, about 10-fold to about 500-fold, about 10-fold to about 100-fold, about 10-fold to about 50-fold, about 10-fold to about 20-fold, about 20-fold to about 1000-fold, about 20-fold to about 500-fold, about 20-fold to about 100-fold, about 20-fold to about 50-fold, about 50-fold to about 1000-fold, about 50-fold to about 500-fold, about 50-fold to about 100-fold, about 100-fold to about 1000-fold, about 100-fold to about 500-fold, or about 500-fold to about 1000-fold.

In some embodiments, the compound provided herein, or a pharmaceutically acceptable salt thereof, selectively inhibits HDAC6 over one or more of HDAC1, HDAC2, HDAC3, HDAC4, HDAC5, HDAC7, HDAC8, HDAC9, HDAC10, and HDAC111.

The present application further provides a method of imaging a subject, comprising:
i) administering to the subject a radiolabeled compound provided herein (e.g., a radiolabeled compound of any of Formulas I-VI), or a pharmaceutically acceptable salt thereof; and
ii) imaging the subject with an imaging technique.

The present application further provides a method of imaging a histone deacetylase (HDAC) enzyme in a cell or tissue, comprising:
i) contacting the cell or tissue with a radiolabeled compound provided herein, or a pharmaceutically acceptable salt thereof; and ii) imaging the cell or tissue with an imaging technique.

The present application further provides a method of imaging a histone deacetylase (HDAC) enzyme in a subject, comprising:
i) administering to the subject a radiolabeled compound provided herein, or a pharmaceutically acceptable salt thereof; and
ii) imaging the subject with an imaging technique.

The present application further provides a method of imaging a disease (e.g., a tumor) in a subject, the method comprising:
i) administering to the subject a radiolabeled compound provided herein, or a pharmaceutically acceptable salt thereof; and
ii) imaging the subject with an imaging technique.

The present application further provides a method of monitoring treatment of a disease in a subject, comprising:
i) imaging the subject with an imaging technique;
ii) administering to the subject a therapeutically effective amount of a compound provided herein, or a pharmaceutically acceptable salt thereof;
iii) imaging the subject with an imaging technique; and
iv) comparing the image of step i) and the image of step iii).

In some embodiments, the method further comprises administering to the subject an imaging agent prior to the imaging of step i). In some embodiments, the method further comprises administering to the subject an imaging agent prior to the imaging of step iii). In some embodiments, the imaging agent is a radiolabeled compound provided herein (e.g., a radiolabeled compound of any of Formulas I-VI). In some embodiments, the compound administered in step ii) further comprises an imaging agent (e.g., a fluorescent moiety or a radioisotope capable of being imaged with an imaging technique).

In some embodiments, the disease is associated with abnormal expression or abnormal activity of a histone deacetylase (HDAC) enzyme in a subject. In some embodiments, the disease to be imaged is associated with abnormal expression or abnormal activity of HDAC6.

The present application further provides a method of imaging the brain in a subject, comprising:
i) administering to the subject a radiolabeled compound provided herein, or a pharmaceutically acceptable salt thereof; and
ii) imaging the subject with an imaging technique.

In some embodiments, the imaging technique is a non-invasive imaging technique. In some embodiments, the imaging technique is a minimally invasive imaging technique. As used herein, the term "minimally invasive imaging technique" comprises imaging techniques employing the use of an internal probe or injection of a compound (e.g., a radiolabeled compound) via syringe.

Example imaging techniques include, but are not limited to, magnetic resonance imaging (MRI), ultrasound imaging, tomographic imaging, positron emission tomography imaging, computed tomography, positron emission tomography with computed tomography imaging, and positron emission tomography with magnetic resonance imaging.

In some embodiments, the imaging technique is selected from the group consisting of single-photon emission computed tomography, positron emission tomography imaging, computed tomography, positron emission tomography with computed tomography imaging, positron emission tomography with magnetic resonance imaging. In some embodiments, the imaging technique is positron emission tomography imaging.

The present application further provides a method of treating a disease in a subject in need thereof, the method comprising administering to the subject a therapeutically effective amount of a compound provided herein, or a pharmaceutically acceptable salt thereof. In some embodiments, the disease is associated with abnormal expression or abnormal activity of a histone deacetylase (HDAC) enzyme. In some embodiments, the disease is selected from the group consisting of cancer, a disease of the central nervous system, and an inflammatory autoimmune disease.

In some embodiments, the disease is cancer. In some embodiments, the cancer is selected from the group consisting of breast cancer, prostate cancer, colon cancer, endometrial cancer, brain cancer (e.g., glioblastoma multiforme), bladder cancer, skin cancer, cancer of the uterus, cancer of the ovary, lung cancer, pancreatic cancer, renal cancer, gastric cancer, and hematological cancer. In some embodiments, the cancer comprises a solid tumor. In some embodiments, the cancer is selected from the group consisting of glioma, glioblastoma, non-small cell lung cancer, and hematological cancer.

In some embodiments, the cancer is a hematological cancer. In some embodiments, the hematological cancer is selected from the group consisting of leukemia and lymphoma. In some embodiments, a hematological cancer is selected from the group consisting of acute myeloblastic leukemia, chronic myeloid leukemia, B cell lymphoma, chronic lymphocytic leukemia (CLL), Non-Hodgkins lymphoma, hairy cell leukemia, Mantle cell lymphoma, Burkitt lymphoma, small lymphocytic lymphoma, follicular lymphoma, lymphoplasmacytic lymphoma, extranodal marginal zone lymphoma, activated B-cell like (ABC) diffuse large B cell lymphoma, and germinal center B cell (GCB) diffuse large B cell lymphoma. In some embodiments, the cancer is associated with abnormal expression or abnormal activity of HDAC6.

In some embodiments, the present application provides a method of treating a cancer in a subject, comprising:
i) identifying the cancer as being associated with abnormal activity or abnormal expression of a histone deacetylase (HDAC) enzyme (e.g., HDAC6); and
ii) if the cancer is identified as being associated with abnormal activity of a histone deacetylase (HDAC) enzyme, then administering to the subject a therapeutically effective amount of a compound provided herein, or a pharmaceutically acceptable salt thereof.

In some embodiments, the disease to be treated is a disease of the central nervous system. In some embodiments, the disease of the central nervous system is selected from the group consisting of Alzehimer's disease, attention deficit/hyperactivity disorder (ADHD), Bell's Palsy, bipolar disorder, catalepsy, Cerebal Palsy, epilepsy, encephalitis, Huntington's disease, locked-in syndrome, meningitis, migraine, multiple sclerosis (MS), Parkinson's disease, Rett syndrome, schizophrenia, tropical spastic paraparesis, and Tourette's syndrome. In some embodiments, the disease of the central nervous system is selected from the group consisting of Alzheimer's disease, bipolar disorder, depression, Huntington's disease, and schizophrenia. In some embodiments, the disease of the central nervous system comprises a neurodegenerative disease (e.g., amyotrophic lateral sclerosis (ALS), Parkinson's disease, Alzheimer's disease, Huntington's disease, and the like). In some embodiments, the disease of the central nervous system is selected from the group consisting of schizophrenia, bipolar disorder, Alzheimer's disease, and Huntington's disease. In some embodiments, the disease of the central nervous system further comprises depression. In some embodiments, the disease of the central nervous system is depression. In some embodiments, the disease of the central nervous system is associated with abnormal expression or abnormal activity of HDAC6.

In some embodiments, the present application provides a method of treating a disease of the central nervous in a subject, comprising:
i) identifying the disease of the central nervous system as being associated with abnormal activity or abnormal expression of a histone deacetylase (HDAC) enzyme (e.g., HDAC6); and
ii) if the disease of the central nervous system is identified as being associated with abnormal activity or abnormal expression of a histone deacetylase (HDAC) enzyme, then administering to the subject a therapeutically effective amount of a compound provided herein, or a pharmaceutically acceptable salt thereof.

In some embodiments, the disease to be treated is an inflammatory autoimmune disease. In some embodiments, the inflammatory autoimmune disease is selected from the group consisting of alopecia areata, autoimmune hemolytic anemia, autoimmune hepatitis, dermatomyositis, diabetes (type 1), juvenile idiopathic arthritis, glomerulonephritis, Graves' disease, Guillain-Barré syndrome, idiopathic thrombocytopenic purpura, myasthenia gravis, myocarditis, pemphigus/pemphigoid, pernicious anemia, polyarteritis nodosa, polymyositis, primary biliary cirrhosis, psoriasis, rheumatoid arthritis, sclerodenna/systemic sclerosis, Sjögren's syndrome, systemic lupus erythematosus, thyroiditis, uveitis, vitiligo, and granulomatosis with polyangiitis (Wegener's granulomatosis). In some embodiments, the inflammatory autoimmune disease is associated with abnormal expression or abnormal activity of HDAC6.

In some embodiments, the present application provides a method of treating an inflammatory autoimmune disease in a subject, the method comprising:
i) identifying the inflammatory autoimmune disease as being associated with abnormal activity or abnormal expression of a histone deacetylase (HDAC) enzyme (e.g., HDAC6); and
ii) if the inflammatory autoimmune disease is identified as being associated with abnormal activity or abnormal expression of a histone deacetylase (HDAC) enzyme, then administering to the subject a therapeutically effective amount of a compound provided herein, or a pharmaceutically acceptable salt thereof.

In some embodiments, about 0.1% to about 5% of the compound or salt administered to the subject crosses the blood brain barrier, for example, from about 0.1% to about 4%, from about 0.1% to about 3%, from about 0.1% to about 2%, from about 0.1% to about 1%, from about 0.1% to about 0.75%, from about 0.1% to about 0.5%, from about 0.1% to about 0.25%, from about 0.25% to about 5%, from about 0.25% to about 4%, from about 0.25% to about 3%, from about 0.25% to about 2%, from about 0.25% to about 1%, from about 0.25% to about 0.75%, from about 0.25% to about 0.5%, from about 0.5% to about 5%, from about 0.5% to about 4%, from about 0.5% to about 3%, from about 0.5% to about 2%, from about 0.5% to about 1%, from about 0.5% to about 0.75%, from about 0.75% to about 5%, from about 0.75% to about 4%, from about 0.75% to about 3%, from about 0.75% to about 2%, from about 0.75% to about 1%, from about 1% to about 5%, from about 1% to about 4%, from about 1% to about 3%, from about 1% to about 2%, from about 2% to about 5%, from about 2% to about 4%, from about 2% to about 3%, from about 3% to about 5%, from about 3% to about 4%, or from about 4% to about 5%.

In some embodiments, the compound administering to the subject has a blood:plasma ratio of from about 1:1 to about 100:1, for example, from about 1:1 to about 2:1, from about 1:1 to about 3:1, from about 1:1 to about 4:1, from about 1:1 to about 5:1, from about 1:1 to about 10:1, from about 1:1 to about 15:1, from about 1:1 to about 20:1, from about 1:1 to about 30:1, from about 1:1 to about 1:40, from about 1:1 to about 50:1, from about 1:1 to about 60:1, from about 1:1 to about 70:1, from about 1:1 to about 80:1, from about 1:1 to about 90:1, from about 1:1 to about 100:1, from about 1:1 to about 3:2, or from about 1:1 to about 4:3. In some embodiments, the blood:plasma ratio is from about 1:100 to about 1:1, for example, from about 1:100 to about 1:1, from about 1:100 to about 1:2, from about 1:100 to about 1:3, from about 1:100 to about 1:4, from about 1:100 to about 1:5, from about 1:100 to about 1:10, from about 1:100 to about 1:15, from about 1:100 to about 1:20, from about 1:100 to about 1:30, from about 1:100 to about 1:40, from about 1:100 to about 1:50, from about 1:100 to about 1:60, from about 1:100 to about 1:70, from about 1:100 to about 1:80, from about 1:100 to about 1:90, at least about 1:100, from about 1:100 to about 2:3, from about 1:100 to about 2:5, from about 1:100 to about 3:4, from about 1:100 to about 3:5, or from about 1:100 to about 4:5. In some embodiments, the compound administered has a brain:plasma ratio of from about 1:1 to about 50:1.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to one or more of (1) inhibiting the disease; for example, inhibiting a disease, condition or disorder in an individual who is experiencing or displaying the pathology or symptomatology of the disease, condition or disorder (i.e., arresting further development of the pathology and/or symptomatology); and (2) ameliorating the disease; for example, ameliorating a disease, condition or disorder in an individual who is experiencing or displaying the pathology or symptomatology of the disease, condition or disorder (i.e., reversing the pathology and/or symptomatology) such as decreasing the severity of disease or reducing or alleviating one or more symptoms of the disease.

Combination Therapies

One or more additional therapeutic agents such as, for example, chemotherapeutic agents, anti-inflammatory agents, steroids, immunosuppressants, therapeutic antibodies, and/or anesthetics, can be used in combination with the compounds and salts provided herein for treatment of HDAC associated diseases, disorders, or conditions.

Example chemotherapeutic agents include proteosome inhibitors (e.g., bortezomib), thalidomide, revlimid, and DNA-damaging agents such as melphalan, doxorubicin, cyclophosphamide, vincristine, etoposide, carmustine, and the like.

Example anti-inflammatory agents include, but are not limited to, aspirin, choline salicylates, celecoxib, diclofenac potassium, diclofenac sodium, diclofenac sodium with misoprostol, diflunisal, etodolac, fenoprofen, flurbiprofen, ibuprofen, ketoprofen, meclofenamate sodium, mefenamic acid, nabumetone, naproxen, naproxen sodium, oxaprozin, piroxican, rofecoxib, salsalate, sodium salicylate, sulindac, tolmetin sodium, and valdecoxib.

Example steroids include, but are not limited to, corticosteroids such as cortisone, dexamethasone, hydrocortisone, methylprednisolone, prednisolone, and prednisone.

Example immunosuppressants include, but are not limited to, azathioprine, chlorambucil, cyclophosphamide, cyclosporine, daclizumab, infliximab, methotrexate, and tacrolimus.

Example anesthetics include, but are not limited, to local anesthetics (e.g., lidocaine, procain, ropivacaine) and general anesthetics (e.g., desflurane, enflurane, halothane, isoflurane, methoxyflurane, nitrous oxide, sevoflurane, mmobarbital, methohexital, thiamylal, thiopental, diazepam, lorazepam, midazolam, etomidate, ketamine, propofol, alfentanil, fentanyl, remifentanil, buprenorphine, butorphanol, hydromorphone levorphanol, meperidine, methadone, morphine, nalbuphine, oxymorphone, pentazocine).

In some embodiments, the additional therapeutic agent is administered simultaneously with a compound or salt provided herein. In some embodiments, the additional therapeutic agent is administered after administration of the compound or salt provided herein. In some embodiments, the additional therapeutic agent is administered prior to administration of the compound or salt provided herein. In some embodiments, the compound or salt provided herein is administered during a surgical procedure. In some embodiments, the compound or salt provided herein is administered in combination with an additional therapeutic agent during a surgical procedure.

Pharmaceutical Compositions and Formulations

When employed as pharmaceuticals, the compounds and salts provided herein can be administered in the form of pharmaceutical compositions. These compositions can be prepared as described herein or elsewhere, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral, or parenteral. Parenteral administration includes intravenous, intraarterial, subcutaneous, intraperitoneal intramuscular or injection or infusion; or intracranial, (e.g., intrathecal or intraventricular, administration). Parenteral administration can be in the form of a single bolus dose, or may be, for example, by a continuous perfusion pump. In some embodiments, the compounds, salts, and pharmaceutical compositions provided herein are suitable for parenteral administration. In some embodiments, the compounds, salts, and pharmaceutical compositions provided herein are suitable for intravenous administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also provided are pharmaceutical compositions which contain, as the active ingredient, a compound provided herein, or a pharmaceutically acceptable salt thereof, in combination with one or more pharmaceutically acceptable carriers (e.g., excipients). In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders.

Some examples of suitable excipients include, without limitation, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include, without limitation, lubricating agents such as talc, magnesium stearate, and mineral oil; wetting agents; emulsifying and suspending agents; preserving agents such as methyl- and propylhydroxy-benzoates; sweetening agents; flavoring agents, or combinations thereof.

The active ingredient can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual subject, the severity of the subject's symptoms, and the like.

EXAMPLES

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

General Materials and Methods

All air- and moisture-insensitive reactions were carried out under an ambient atmosphere and magnetically stirred. Tetrahydrofuran was distilled from deep purple sodium benzophenone ketyl. Dry DMF and dry DMSO were purchased from Acros Organics. Other anhydrous solvents (acetonitrile, diethyl ether, dichloromethane, pentane, and toluene) were obtained by filtration through drying columns (see e.g., Pangborn et al, *Organometallics,* 1996, 15:1518-1520) on an mBraun system. All air- and moisture-sensitive manipulations were performed using oven-dried glassware, under nitrogen atmosphere.

Thin layer chromatography (TLC) was performed by EMD TLC plates pre-coated with 250 µm thickness silica gel 60 $F_{254}$ plates and visualized by fluorescence quenching under UV light and $KMnO_4$ stain. Flash chromatography was performed on an Isolera One (Biotage) using Silicycle columns as recommended based on $R_f$ and mass of analyte. Anhydrous acetonitrile was purchased from VWR, anhydrous acetone was purchased from Acros and sparged with nitrogen for 30 min before use. Silica gel (230-400 mesh) purchased from Silicycle Inc., or, where stated, flash chromatography was performed using spherical silica gel cartridges (ZIP sphere) from Biotage with an Isolera purification system.

All deuterated solvents were purchased from Cambridge Isotope Laboratories. NMR spectra were recorded on either a Varian Unity/Inova 600 spectrometer operating at 600 MHz for $^1H$ acquisitions, a Varian Unity/Inova 500 spectrometer operating at 500 MHz, 471 MHz, and 125 MHz for $^1H$, $^{19}F$ and $^{13}C$ acquisitions, respectively or a Varian Mercury 400 spectrometer operating at 375 MHz for $^{19}$F acquisitions. Chemical shifts are reported in ppm with the solvent resonance as the internal standard ($^1$H: Chloroform-d, δ 7.26; DMSO-d$_6$, δ 2.50), ($^{13}$C: CDCl$_3$, δ 77.16; DMSO-d$_6$, δ 39.52). Data is reported as follows: s=singlet, d=doublet, t=triplet, m=multiplet; coupling constants in Hz; integration; carbon signals are singlets unless otherwise noted. All substrates were used as received from commercial suppliers, unless otherwise stated. Ru(cod)(cp)Cl was synthesized as previously described.

Intermediate 1. Methyl-4-((((adamantan-1-yl)methyl)amino)methyl)-2-fluorobenzoate

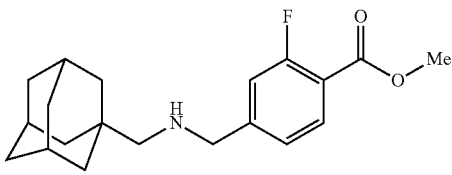 [SMILES: COC(=O)c1ccc(CNCC23CC4CC(CC(C4)C2)C3)cc1F]

A solution of methyl 2-fluoro-4-formylbenzoate (100 mg, 0.549 mol 1.0 eq.) and 1-adamantanemethylamine (100 mg, 0.606 mol, 1.1 eq.) in 2 mL methanol was stirred for 2 h at room temperature. Next, 50 mg sodium borohydride was added and the reaction mixture was stirred until no starting material remained. The mixture was concentrated in vacuo, partitioned between ethyl acetate and water, the aqueous layer extracted two more times with ethyl acetate and the combined organic phases were dried over sodium sulfate. The solvent was removed under reduced pressure and the product was purified by column chromatography. The title product (153 mg, 0.461 mmol, 92%) was obtained as a clear oil that solidified upon standing. $^1$H NMR (500 MHz, Chloroform-d) δ 7.88 (td, J=7.7, 1.0 Hz, 1H), 7.24-7.09 (m, 2H), 3.92 (d, J=1.2 Hz, 3H), 3.82 (s, 2H), 2.21 (d, J=1.0 Hz, 2H), 1.97 (t, J=3.1 Hz, 3H), 1.74-1.60 (m, 6H), 1.52 (d, J=2.9 Hz, 6H).

Intermediate 2. Methyl-4-((((adamantan-1-yl)methyl)amino)methyl)-3,5-difluorobenzoate

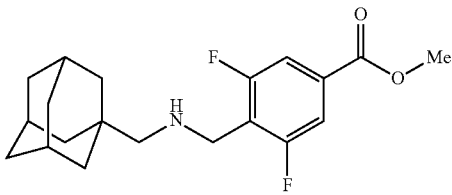 [SMILES: COC(=O)c1cc(F)c(CNCC23CC4CC(CC(C4)C2)C3)c(F)c1]

A solution of methyl 3,5-difluoro-4-formylbenzoate (100 mg, 0.500 mol 1.0 eq.) and 1-adamantanemethylamine (100 mg, 0.606 mol, 1.2 eq.) in 2 mL methanol was stirred for 2 h at room temperature. Next, 150 mg sodium triacetoxyborohydride was added and the reaction mixture was stirred until no starting material remained. The mixture was concentrated in vacuo, partitioned between ethyl acetate and water, the aqueous layer extracted two more times with ethyl acetate and the combined organic phases were dried over sodium sulfate. The solvent was removed under reduced pressure and the product was purified by column chromatography. The title product (62 mg, 0.177 mmol, 35%) was obtained as a clear oil. $^1$H NMR (500 MHz, Chloroform-d) δ 6.90 (d, J=7.4 Hz, 2H), 4.69 (s, 3H), 3.88 (d, J=1.2 Hz, 2H), 2.19 (s, 2H), 1.95 (s, 3H), 1.77-1.54 (m, 6H), 1.48 (d, J=2.8 Hz, 6H).

Intermediate 3. Methyl-4-((((adamantan-1-yl)methyl)amino)methyl)-3-trifluoromethylbenzoate

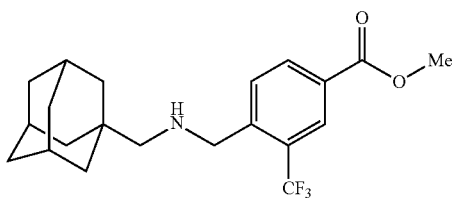 [SMILES: COC(=O)c1ccc(CNCC23CC4CC(CC(C4)C2)C3)c(C(F)(F)F)c1]

A solution of methyl 3-trifluoromethyl-4-formylbenzoate (100 mg, 0.431 mol 1.0 eq.) and 1-adamantanemethylamine (100 mg, 0.606 mol, 1.4 eq.) in 2 mL methanol was stirred for 2 h at room temperature. Next, 50 mg sodium borohydride was added and the reaction mixture was stirred until no starting material remained. The mixture was concentrated in vacuo, partitioned between ethyl acetate and water, the aqueous layer extracted two more times with ethyl acetate and the combined organic phases were dried over sodium sulfate. The solvent was removed under reduced pressure and the product was purified by column chromatography. The title product (65.2 mg, 0.171 mmol, 39.7%) was obtained as a clear oil that solidified upon standing. $^1$H NMR (500 MHz, Chloroform-d) δ 8.31 (d, J=2.0 Hz, 11H), 8.20 (d, J=8.1 Hz, 11H), 7.87 (d, J=8.1 Hz, 1H), 4.01 (s, 2H), 3.96 (d, J=1.9 Hz, 3H), 2.26 (d, J=1.6 Hz, 2H), 1.99 (s, 3H), 1.78-1.60 (m, 6H), 1.55 (s, 6H).

Intermediate 4. Methyl-4-((((adamantan-1-yl)methyl)amino)methyl)-3-methylbenzoate

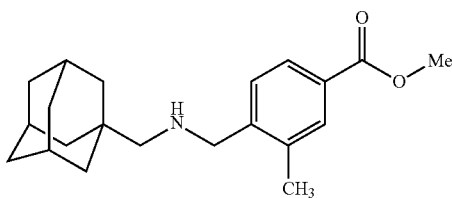 [SMILES: COC(=O)c1ccc(CNCC23CC4CC(CC(C4)C2)C3)c(C)c1]

A solution of methyl 3-methyl-4-formylbenzoate (100 mg, 0.561 mol 1.0 eq.) and 1-adamantanemethylamine (100 mg, 0.606 mol, 1.1 eq.) in 2 mL methanol was stirred for 2 h at room temperature. Next, 50 mg sodium borohydride was added and the reaction mixture was stirred until no starting material remained. The mixture was concentrated in vacuo, partitioned between ethyl acetate and water, the aqueous layer extracted two more times with ethyl acetate and the combined organic phases were dried over sodium sulfate. The solvent was removed under reduced pressure and the product was purified by column chromatography. The title product (131 mg, 0.400 mmol, 71.3%) was obtained as a clear oil that solidified upon standing. $^1$H NMR (500 MHz, Chloroform-d) δ 7.91-7.78 (m, 2H), 7.42 (d, J=7.8 Hz, 1H), 3.91 (d, J=1.2 Hz, 3H), 3.79 (s, 2H), 2.38 (s, 3H), 2.29 (d, J=1.4 Hz, 2H), 1.98 (s, 3H), 1.80-1.49 (m, 12H).

Intermediate 5. Methyl-6-((((adamantan-1-yl)methyl)amino)methyl)-nicotinic acid

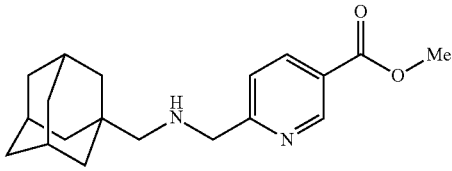 [SMILES: COC(=O)c1ccc(CNCC23CC4CC(CC(C4)C2)C3)nc1]

A solution of methyl 4-formylnicotinic acid (100 mg, 0.606 mol 1.0 eq.) and 1-adamantanemethylamine (100 mg, 0.606 mol, 1.0 eq.) in 2 mL methanol was stirred for 2 h at room temperature. Next, 150 mg sodium triacetoxyborohydride was added and the reaction mixture was stirred until no starting material remained. The mixture was concentrated in vacuo, partitioned between ethyl acetate and water, the aqueous layer extracted two more times with ethyl acetate and the combined organic phases were dried over sodium sulfate. The solvent was removed under reduced pressure and the product was purified by column chromatography. The title product (75 mg, 0.239 mmol, 39%) was obtained as a clear oil. 1H NMR (500 MHz, Chloroform-d) δ 9.15 (d, J=2.2 Hz, 1H), 8.26 (dd, J=8.2, 2.1 Hz, 1H), 7.47 (d, J=8.2 Hz, 1H), 3.97 (s, 2H), 3.96 (d, J=1.6 Hz, 3H), 2.27 (s, 2H), 1.98 (s, 3H), 1.80-1.61 (m, 6H), 1.55 (d, J=2.8 Hz, 6H).

Intermediate 6. methyl 4-((((adamantan-1-yl)methyl)amino)methyl)-3-chlorobenzoate

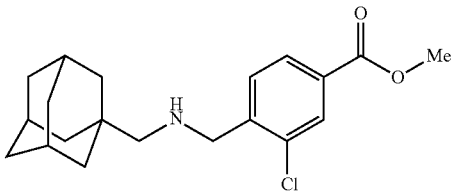 [SMILES: COC(=O)c1ccc(CNCC23CC4CC(CC(C4)C2)C3)c(Cl)c1]

A solution of methyl 3-chloro-4-formylbenzoate (100 mg, 0.505 mmol, 1.0 eq.) and 1-adamantanemethylamine (100 mg, 0.606 mol, 1.2 eq.) in 2 mL methanol was stirred for 2 h at room temperature. Next, 150 mg sodium triacetoxyborohydride was added and the reaction was stirred until no starting material remained. The mixture was concentrated in vacuo, partitioned between ethyl acetate and water, the aqueous layer extracted two more times with ethyl acetate and the combined organic phases were dried over sodium sulfate. The solvent was removed under reduced pressure and the product was purified by column chromatography. The title product (72 mg, 0.207 mmol, 41%) was obtained as a clear oil. 1H NMR (500 MHz, Chloroform-d) δ 8.02 (t, J=1.6 Hz, 1H), 7.96-7.87 (m, 1H), 7.54 (d, J=8.0 Hz, 1H), 3.93 (s, 3H), 3.92 (s, 2H), 2.24 (s, 2H), 2.18 (s, 1H), 1.98 (s, 3H), 1.76-1.62 (m, 6H), 1.54 (d, J=2.7 Hz, 6H).

Intermediate 7. methyl 4-((((adamantan-1-yl)methyl)amino)methyl)-3-bromobenzoate

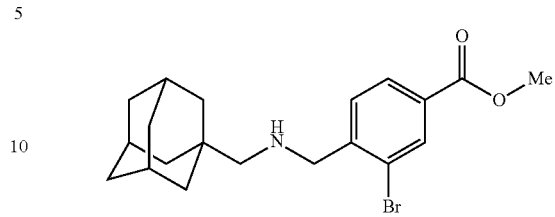

A solution of methyl 3-bromo-4-formylbenzoate (100 mg, 0.412 mmol 1.0 eq.) and 1-adamantanemethylamine (100 mg, 0.606 mol, 1.5 eq.) in 2 mL methanol was stirred for 2 h at room temperature. Next, 150 mg sodium triacetoxyborohydride was added and the reaction was stirred until no starting material remained. The mixture was concentrated in vacuo, partitioned between ethyl acetate and water, the aqueous layer extracted two more times with ethyl acetate and the combined organic phases were dried over sodium sulfate. The solvent was removed under reduced pressure and the product was purified by column chromatography. The title product (104 mg, 0.265 mmol, 64%) was obtained as a clear oil. 1H NMR (500 MHz, Chloroform-d) δ 8.21 (d, J=1.7 Hz, 1H), 8.06-7.86 (m, 1H), 7.53 (d, J=8.0 Hz, 1H), 3.93 (s, 3H), 3.89 (s, 2H), 2.24 (s, 2H), 2.18 (s, 1H), 1.98 (s, 3H), 1.82-1.60 (m, 6H), 1.54 (d, J=2.6 Hz, 6H).

Intermediate 8. Methyl 4-(((((3r,5r,7r)-adamantan-1-yl)methyl)amino)methyl)benzoate

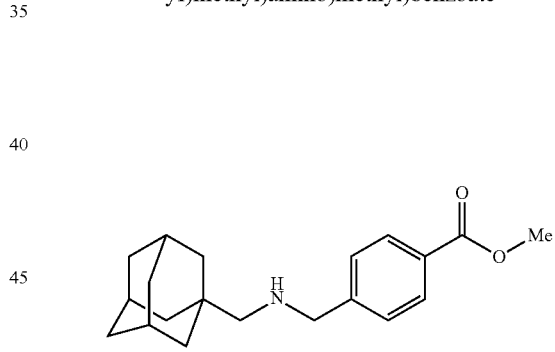

A solution of methyl 4-formylbenzoate (155 mg, 0.94 mol 1.1 eq.) and 1-adamantanemethylamine (140 mg, 0.85 mol, 1 eq.) in 3 mL methanol was stirred for 2 h at room temperature. Next, 210 mg sodium borohydride was added portionwise and the reaction was stirred until no starting material remained, approximately 3.5 h. The mixture was concentrated in vacuo, partitioned between ethyl acetate and water, the aqueous layer extracted two more times with ethyl acetate and the combined organic phases were dried over sodium sulfate. The solvent was removed under reduced pressure and the product was purified by column chromatography. The title product (221 mg, 0.71 mmol, 75%) was obtained as a clear oil that solidified upon standing. 1H NMR (chloroform-d) δ 7.99 (d, 2H), 7.41 (d, 2H), 3.90 (s, 1H), 3.86 (s, 5H), 2.23 (s, 2H), 1.97 (s, 3H), 1.82-1.59 (m, 7H), 1.59-1.44 (m, 7H). MS (m/z) calc'd for $C_{20}H_{27}NO_2$ [M+H]$^+$ 313.20; found, 313.7.

Intermediate 9. Methyl 4-((((3s,5s,7s)-adamantan-1-yl)amino)methyl)benzoate

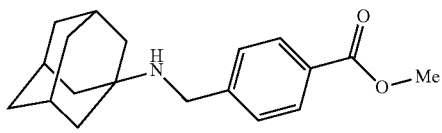 [SMILES: COC(=O)c1ccc(CNC23CC4CC(CC(C4)C2)C3)cc1]

A solution of methyl 4-bromomethylbenzoate (300 mg, 1.83 mmol, 1.4 eq.) and 1-adamantanamine (201 mg, 1.33 mol, 1 eq.) in 1.5 mL DMSO, 200 μL N,N-diisopropylethylamine was added and the mixture was stirred for 12 h at 60° C. The mixture was diluted with water, partitioned between ethyl acetate and water, the aqueous layer extracted two more times with ethyl acetate and the combined organic phases were then extracted with three time with water. Next, the organic phase was dried over sodium sulfate. The solvent was removed under reduced pressure and the product was purified by column chromatography. The title product (44.6 mg, 0.15 mmol, 11%) was obtained as a clear oil that solidified upon standing. 1H NMR (chloroform-d) δ 7.98 (d, 2H), 7.43 (d, 2H), 3.89 (s, 5H), 2.12 (s, 3H), 1.79-1.51 (m, 13H). MS (m/z) calc'd for $C_{19}H_{25}NO_2$ [M+H]$^+$ 299.2; found, 299.7.

Intermediate 10. Methyl 4-(((1-((3r,5r,7r)-adamantan-1-yl)propan-2-yl)amino)methyl)benzoate

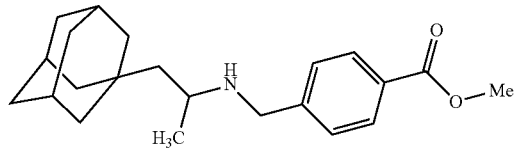 [SMILES: COC(=O)c1ccc(CNC(C)CC23CC4CC(CC(C4)C2)C3)cc1]

A solution of methyl 4-formylbenzoate (198 mg, 1.21 mmol 1.75 eq.) and 1-(1-adamantyl)propan-1-amine) (134 mg, 0.69 mmol, 1 eq.) in 6 mL methanol was stirred for 40 min at room temperature. Next, 200 mg sodium borohydride was added portionwise and the reaction was stirred until no starting material remained, approximately 3 h. The mixture was concentrated in vacuo, partitioned between ethyl acetate and water, the aqueous layer extracted two more times with ethyl acetate and the combined organic phases were dried over sodium sulfate. The solvent was removed under reduced pressure and the product was purified by column chromatography. The title product (339 mg, 0.41 mmol, 60%) was obtained as a clear gel. 1H NMR (chloroform-d6) δ 8.00 (d, 2H), 7.42 (d, 2H), 3.84 (s, 5H), 2,80 (m, 111), 1.93 (s, 3H), 1.82-1.42 (m, 14H), 1.34-1.20 (m, 2H), 1.20-1.01 (m, 4H). MS (m/z) calc'd for $C_{22}H_{31}NO_2$ [M+H]$^+$ 341.24; found, 341.7.

Intermediate 11. Methyl 4-(((1-((3r,5r,7r)-adamantan-1-yl)propyl)amino)methyl)benzoate

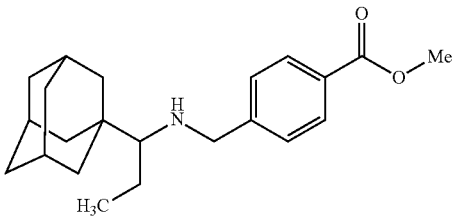 [SMILES: CCC(NCc1ccc(C(=O)OC)cc1)C12CC3CC(CC(C3)C1)C2]

A solution of methyl 4-formylbenzoate (202 mg, 1.23 mmol, 1 eq.) and 1-(1-adamantyl)propan-1-amine) (232 mg, 1.20 mmol, 1 eq.) in 6 mL methanol was stirred for 45 min at room temperature. Next, 200 mg sodium borohydride was added portionwise and the reaction was stirred until no starting material remained, approximately 3 h. The mixture was concentrated in vacuo, partitioned between ethyl acetate and water, the aqueous layer extracted two more times with ethyl acetate and the combined organic phases were dried over sodium sulfate. The solvent was removed under reduced pressure and the product was purified by column chromatography. The title product (136 mg, 0.413 mmol, 74.3%) was obtained as a clear oil that solidified upon standing. 1H NMR (chloroform-d6) δ 7.9 (d, 2H), 7.4 (d, 2H), 4.08 (m, 4H), 3.8 (m, 1H), 1.99 (m, 3H), 1.85 (m, 1H), 1.78-1.44 (m, 15H), 1.24-1.06 (m, 2H), 1.06-0.87 (m, 4H). MS (m/z) calc'd for $C_{22}H_{31}NO_2$ [M+H]$^+$ 341.2; found, 341.7.

Intermediate 12. Methyl 4-(((((6,6-dimethylbicyclo[3.1.1]heptan-2-yl)methyl)amino)methyl)benzoate

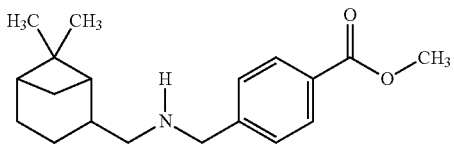 [SMILES: COC(=O)c1ccc(CNCC2CCC3CC2C3(C)C)cc1]

A solution of methyl 4-formylbenzoate (0.306 mg, 1.86 mmol, mole 1.1 eq.) and (−)-cis-Myrtanylamine (247 mg, 1.62 mmol, 1 eq.) in 5 mL methanol was stirred for 1.5 h at room temperature. Next, 175 mg sodium borohydride was added portionwise and the reaction was stirred until no starting material remained, approximately 4 h. The mixture was concentrated in vacuo, partitioned between ethyl acetate and water, the aqueous layer extracted two more times with ethyl acetate and the combined organic phases were dried over sodium sulfate. The solvent was removed under reduced pressure and the product was purified by column chromatography. The title product (463 mg, 1.54 mmol, 94%) was obtained as a yellowish oil. 11H NMR (chloroform-d) δ 8.0 (d, 211), 7.6 (d, 2H), 4.17-3.77 (m, 3H), 3.98 (s, 2H), 2.77-1.65 (m, 11H), 1.65-0.43 (m, 11H). MS (m/z) calc'd for $C_{19}H_{27}NO_2$ [M+H]$^+$ 301.20; found, 301.7.

Intermediate 13. Methyl 4-(((cyclohexylmethyl)amino)methyl)benzoate

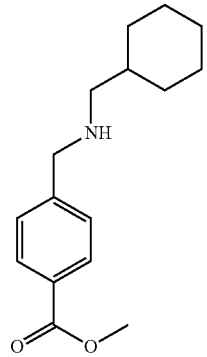 [SMILES: COC(=O)c1ccc(CNCC2CCCCC2)cc1]

A solution of methyl 4-formylbenzoate (0.303 mg, 1.84 mmol, mole 1.2 eq.) and cyclohexanemethylamine (174 mg, 1.53 mmol, 1 eq.) in 5 mL methanol was stirred for 0.5 h at room temperature. Next, 170 mg sodium borohydride was added portionwise and the reaction was stirred until no starting material remained, approximately 3 h. The mixture was concentrated in vacuo, partitioned between ethyl acetate and water, the aqueous layer extracted two more times with ethyl acetate and the combined organic phases were dried over sodium sulfate. The solvent was removed under reduced pressure and the product was purified by column chromatography. The title product (363 mg, 1.39 mmol, 91%) was obtained as a yellowish oil. 1H NMR (chloroform-d) δ 8.0 (d, 2H), 7.4 (d, 3H), 4.0 (s, 2H), 2.45-1.97 (m, 2H), 1.97-1.44 (m, 7H), 1.44-0.92 (m, 6H), 0.93-0.53 (m, 2H). MS (m/z) calc'd for $C_{16}H_{23}NO_2$ [M+H]$^+$ 261.17; found, 261.7.

Intermediate 14. [CpRu(cod)Cl]

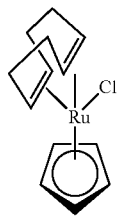

Step 1. [RuCl$_2$(cod)]$_n$

A two-neck round bottom flask was flame-dried and purged with N$_2$. Ruthenium trichloride hydrate (RuCl$_3$·xH$_2$O, 7.4 g, 0.03 mol, 1 eq; RuCl·xH$_2$O contained variable water content, the total ruthenium content was 40-43%) was added to the flask. The flask was evacuated and kept under vacuum for 1 h and then was purged with N$_2$. To the flask was added 1,5-cyclooctadiene (20 mL, 18 g, 0.16 mol, 5 eq.) and ethanol (0.14 L, c=0.2 M) to give a dark brown solution. The reaction mixture was stirred and heated at reflux at 95° C. for 48 h and subsequently cooled to 23° C. The resulting brown precipitate was filtered off through a sintered glass funnel under air, and washed thoroughly with ethanol (50 mL). The brown solid was dried under vacuum for 48 h to afford [RuCl$_2$(cod)]$_n$ (8.2 g). The material was used in subsequent steps without further purification.

Step 2. [(cod)RuH(NH$_2$NMe$_2$)$_3$]PF$_6$

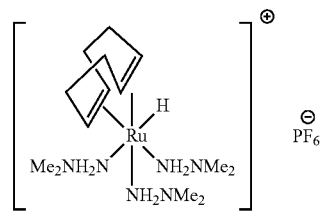

To an oven dried 250 mL two-neck round bottom flask equipped with a magnetic stir bar was added [RuCl$_2$(cod)]$_n$ (5.50 g) under N$_2$. To the flask were added degassed methanol (55 mL), degassed water (13.8 mL) and freshly distilled degassed N,N'-dimethyl hydrazine (55 mL, 43 g, 0.72 mol). The mixture was heated at 95° C. and stirred at the same temperature for 45 min. The resulting mixture was subsequently cooled to 23° C. over 60 min with stirring. Under N$_2$, to the above reaction mixture was added a degassed solution of NH$_4$PF$_6$ (5.5 g, 34 mmol) in H$_2$O (55 mL). The slurry was maintained at −20° C. for 12 h under N$_2$. The resulting colorless precipitate was filtered through a sintered glass funnel under air. Then the filtrate was concentrated under reduced pressure to half of the volume and was kept at −20° C. for 60 min. The resulting colorless precipitate was filtered through a sintered glass funnel to afford a second crop of product, which was combined with the previous fraction. The combined colorless precipitate was washed thoroughly with ice-cold water (200 mL) and dried under vacuum for 48 h to afford [(cod)RuH(NH$_2$NMe$_2$)$_3$]PF$_6$ (4.9 g). The material was used in subsequent steps without further purification.

Step 3. [CpRu(cod)Cl]

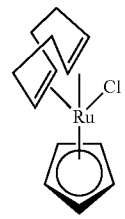

Inside a nitrogen-filled glovebox, a 250 mL two necked round bottom flask equipped with a magnetic stir-bar and a rubber septum was charged with [(cod)RuH(Me$_2$NNH$_2$)$_3$]PF$_6$ (5.00 g) and thallium cyclopentadienide (2.78 g, 10.3 mmol). The flask was sealed with a second rubber septum and was brought outside the glovebox. Degassed acetone (88 mL) was added to the flask under N$_2$. The mixture was heated at 65° C. and stirred at the same temperature for 30 min. The resulting mixture was subsequently cooled to 23° C. over 20 min. The mixture was transferred with a cannula into a Schlenck flask, sealed, and brought inside a glovebox. The mixture was filtered through a pad of celite under vacuum. The resulting filtrate was concentrated in vacuo to afford a brown solid. Pentane (30 mL) was added to the brown solid and the mixture was shaken vigorously for 10 min. The resulting mixture was drawn into a syringe and filtered through a 0.2 nm PTFE syringe filter into a separate 50 mL flask containing CCl$_4$ (1.93 mL). A yellow precipitate was observed. The above sequence of pentane (30 mL) addition to the brown solid was repeated. The supernatant was filtered again and added to the CCl$_4$ containing flask. The mixture was stirred inside a glove box for 30 min. Then the flask was removed from the glove box, and the mixture was filtered through a sintered glass funnel under air. The resulting solid was washed with pentane (30 mL) and dried under vacuum to afford [CpRu(cod)Cl] (1.21 g, 3.27 mmol, 16±1% from RuCl$_3$) as a dark yellow solid. $^1$H NMR (500 MHz, CDCl$_3$, 23° C., δ): 5.32-5.29 (m, 2H), 4.95 (s, 5H), 4.41-4.38 (m, 2H), 2.62-2.59 (m, 2H), 2.10-2.03 (m, 4H), 2.00-1.93 (m, 2H) (1H NMR spectroscopic data correspond to the data reported in the literature (see e.g., *Chem. Eur. J.* 2014, 20, 11101-11110). $^{13}$C NMR (125 MHz, CDCl$_3$, 23° C., δ): 128.8, 87.1, 85.9, 78.7, 32.6, 28.1, 28.0. HRMS (m/z) calc'd for C$_{13}$H$_{17}$ClRu [M-Cl]$^+$, 275.0374; found, 275.0367.

Example 1. 4-(((((3s)-Adamantan-1-yl)methyl) (methyl)amino)methyl)-3-fluoro-N-hydroxybenzamide

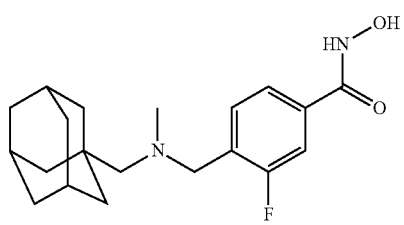 [SMILES: CN(Cc1ccc(C(=O)NO)cc1F)CC12CC3CC(CC(C3)C1)C2]

Step 1. Methyl 4-(((((3s)-adamantan-1-yl)methyl)amino) methyl)-3-fluorobenzoate

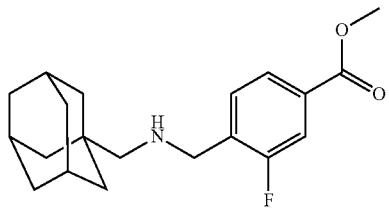 [SMILES: COC(=O)c1ccc(CNCC23CC4CC(CC(C4)C2)C3)c(F)c1]

A solution of 250 mg (1.37 mmol) of methyl 3-fluoro-4-formylbenzoate and 238 mg adamantanemethylamine (1.44 mmol, 1.05 eq) in 2 mL methanol was stirred for 30 min at room temperature. Then, 104 mg (2.74 mmol, 2.00 eq) sodium borohydride was added and the reaction was stirred until no starting material remained, approximately 3 h. The mixture was concentrated in vacuo, partitioned between ethyl acetate and water, the aqueous layer extracted two more times with ethyl acetate and the combined organic phases were dried over sodium sulfate. The solvent was removed under reduced pressure and the product was purified by column chromatography. 372 mg (1.12 mmol, 82%) of the methyl 4-((((adamantan-1-yl)methyl)amino)methyl)-3-fluorobenzoate were obtained as a clear oil that solidified upon standing. R$_f$(25% EtOAc, 75% Hexanes)=0.49; $^1$H NMR (500 MHz, Chloroform-d) δ 7.79 (dd, J=7.9, 1.6 Hz, 1H), 7.66 (dd, J=10.5, 1.6 Hz, 1H), 7.49 (t, J=7.6 Hz, 1H), 3.90 (s, 3H), 3.88 (s, 2H), 2.22 (s, 2H), 1.94 (d, J=3.1 Hz, 2H), 1.80-1.65 (m, 3H), 1.65-1.57 (m, 3H), 1.51 (d, J=3.0 Hz, 6H). $^{13}$C NMR (126 MHz, Chloroform-d) δ 164.49, 160.85 (d, J=247.4 Hz), 132.34, 131.35, 129.58 (d, J=13.3 Hz), 122.45, 114.22 (d, J=24.8 Hz), 70.83, 56.96, 45.36, 40.88, 37.10, 34.97, 28.42. $^{19}$F NMR (471 MHz, Chloroform-d) δ-118.66. HRMS: m/z (+H$^+$) calc'd: 332.2020, found: 332.2068.

Step 2. Methyl 4-(((((3s)-adamantan-1-yl)methyl)(methyl) amino)methyl)-3-fluorobenzoate

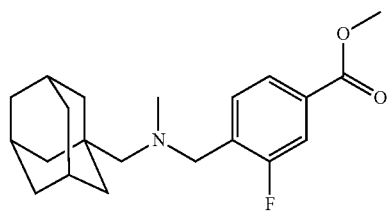 [SMILES: COC(=O)c1ccc(CN(C)CC23CC4CC(CC(C4)C2)C3)c(F)c1]

A solution of 350 mg (1.06 mmol) of methyl 4-((((adamantan-1-yl)methyl)amino)methyl)-3-fluorobenzoate in 3 mL methanol, 0.5 mL formalin and a drop of acetic acid were stirred for 2 h, then 80.2 mg (2.12 mmol, 2 eq) of sodium borohydride were added and the mixture stirred for another hour. The mixture was concentrated in vacuo, partitioned between ethyl acetate and water, the aqueous layer extracted two more times with ethyl acetate and the combined organic phases were dried over sodium sulfate. The solvent was removed under reduced pressure and the product was purified by column chromatography. 227 mg (0.657 mmol, 62%) of methyl 4-(((((3s)-adamantan-1-yl)methyl) (methyl)amino)methyl)-3-fluorobenzoate were obtained as a clear oil that solidified upon standing. R$_f$(25% EtOAc, 75% Hexanes)=0.75; $^1$H NMR (600 MHz, Chloroform-d) δ 7.73 (dd, J=7.9, 1.6 Hz, 1H), 7.64-7.44 (m, 2H), 3.83 (s, 3H), 3.56 (s, 2H), 2.16 (s, 3H), 2.06 (s, 2H), 1.90-1.80 (m, 3H), 1.63 (dd, J=12.2, 3.3 Hz, 3H), 1.59-1.52 (m, 3H), 1.46-1.35 (m, 6H). $^{13}$C NMR (126 MHz, Chloroform-d) δ 165.75, 160.66 (d, J=245.8 Hz), 132.49 (d, J=14.3 Hz), 130.62, 130.26, 124.94, 116.06 (d, J=24.0 Hz), 71.00, 57.15, 51.98, 45.52, 40.91, 37.12, 35.06, 28.42. $^{19}$F NMR (471 MHz, Chloroform-d) δ-117.64 HRMS: m/z (+H$^+$) calc'd: 346.2177, found: 346.2158.

Step 3. 4-(((((3s)-adamantan-1-yl)methyl)(methyl) amino)methyl)-3-fluoro-N-hydroxybenzamide

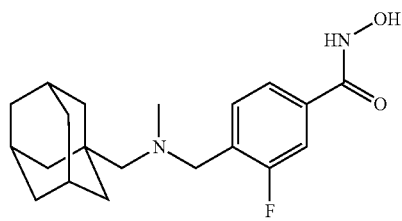 [SMILES: CN(Cc1ccc(C(=O)NO)cc1F)CC12CC3CC(CC(C3)C1)C2]

To a solution of 200 mg ester (0.580 mmol) in 2 mL 1:1 THF/MeOH at 0° C. was added 0.5 mL hydroxylamine (50% aq) and 0.1 mL 5M NaOH. The reaction mixture was stirred for 2 h, then partitioned between DCM and water. The aqueous layer was extracted another three times with DCM, the combined organic phases were dried over sodium sulfate and concentrated in vacuo. The product was purified by preparative HPLC with a gradient of water and acetonitrile buffered with formic acid. The hydroxamate was obtained as a light yellow oil, which turned into 123 mg (0.355 mmol, 61%) of a light orange, foamy solid upon further drying in vacuo. ¹H NMR (600 MHz, Chloroform-d) δ 11.21 (s, 1H), 9.11 (s, 1H), 7.59-7.50 (m, 2H), 7.47 (dd, J=10.9, 1.6 Hz, 1H), 3.56 (s, 2H), 2.16 (s, 3H), 2.08 (s, 2H), 1.88 (s, 3H), 1.63 (d, J=12.3 Hz, 3H), 1.55 (d, J=12.2 Hz, 3H), 1.43 (s, 6H). ¹³C NMR (126 MHz, Chloroform-d) δ 164.49, 160.85 (d, J=247.4 Hz), 132.34, 131.35, 129.63, 122.45, 114.22 (d, J=24.8 Hz), 70.83, 56.96, 45.36, 40.88, 37.10, 34.97, 28.42. ¹⁹F NMR (471 MHz, Chloroform-d) δ -116.71. HRMS: m/z (+H*) calc'd: 347.2129, found: 347.2560.

Example 2. 4-((((Adamantan-1-yl)methyl)(methyl)amino)methyl)-3-[$^{18}$F]fluoro-N-hydroxybenzamide

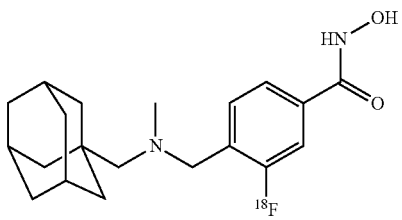 [SMILES: CN(Cc1ccc(C(=O)NO)cc1[18F])CC12CC3CC(CC(C3)C1)C2]

Step 1. Methyl 3-hydroxy-4-(hydroxymethyl)benzoate

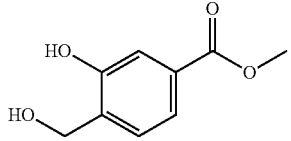

To a solution of 500 mg (2.38 mmol) dimethyl hydroxyterephthalate in 5 mL THF was added 180 mg (4.76 mmol, 2 eq) sodium borohydride and the resulting suspension was heated at reflux for 2 h. The solvent was removed in vacuo and 5 mL of water was added to the resulting residue. The solution was then acidified with 1M HCl and stored at 0° C. until crystallization was observed. The product was purified by column chromatography and 368 mg (2.02 mmol, 85%) of the product was obtained as a white solid. $R_f$(25% EtOAc, 75% Hexanes)=0.11; ¹H NMR (600 MHz, DMSO-d$_6$) δ 9.83 (s, 1H), 7.42 (dt, J=3.3, 1.9 Hz, 2H), 7.36 (q, J=1.6 Hz, 1H), 5.16 (s, 1H), 4.51 (s, 2H), 3.81 (dd, J=2.2, 1.1 Hz, 3H). ¹³C NMR (126 MHz, DMSO-d$_6$) δ 167.24, 154.83, 135.52, 129.49, 127.85, 120.75, 115.56, 58.90, 52.87. HRMS: m/z (+Na⁺). calc'd: 205.0471, found: 205.0471.

Step 2. Methyl 4-formyl-3-hydroxybenzoate

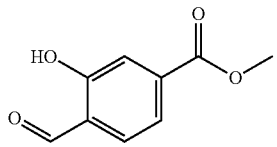

To a solution of 250 mg (1.37 mmol) methyl 3-hydroxy-4-(hydroxymethyl)benzoate in 3 mL 10% aqueous methanol was added 73 mg (10% loading, 0.034 mmol, 2.5 mol %) Pd/C, 567 mg (4.11 mmol, 3 eq) potassium carbonate, and 5.2 mg (0.137, 0.1 eq) sodium borohydride, and the mixture was stirred under an atmosphere of oxygen overnight. Then, the mixture was diluted with dichloromethane and filtered. The mixture was concentrated in vacuo, partitioned between ethyl acetate and water, and the aqueous layer extracted two more times with ethyl acetate. The combined organic phases were then dried over sodium sulfate. The solvent was removed under reduced pressure and the product was purified by column chromatography. 92 mg (0.506 mmol, 37%) of the methyl 4-formyl-3-hydroxybenzoate were obtained as a white solid. $R_f$(25% EtOAc, 75% Hexanes)=0.50; ¹H NMR (600 MHz, Chloroform-d) δ 10.94 (s, 1H), 9.98 (s, 1H), 7.69-7.63 (m, 3H), 3.94 (s, 3H). ¹³C NMR (126 MHz, Chloroform-d) δ 196.44, 165.67, 161.24, 137.30, 133.62, 122.86, 120.40, 119.12, 52.69. HRMS: m/z (+H⁺). calc'd: 181.0495, found: 181.0494.

Step 3. Methyl 4-((((adamantan-1-yl)methyl)amino)methyl)-3-hydroxybenzoate

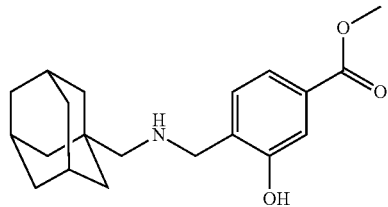 [SMILES: COC(=O)c1ccc(CNCC23CC4CC(CC(C4)C2)C3)c(O)c1]

A solution of 100 mg (0.556 mmol) of methyl 4-formyl-3-hydroxybenzoate and 96.4 mg adamantanemethylamine (0.583 mmol, 1.05 eq) in 2 mL methanol was stirred for 30 min at room temperature. Then, 37.8 mg (1.00 mmol, 1.80 eq) sodium borohydride was added and the reaction mixture was stirred for about 3 h. The mixture was concentrated in vacuo, partitioned between ethyl acetate and water, the aqueous layer extracted two more times with ethyl acetate and the combined organic phases were then dried over sodium sulfate. The solvent was removed under reduced pressure and the product was purified by column chromatography. 136 mg (0.413 mmol, 74%) of the methyl 4-((((adamantan-1-yl)methyl)amino)methyl)-3-hydroxybenzoate was obtained as a clear oil that solidified upon standing. $R_f$(25% EtOAc, 75% Hexanes)=0.46; ¹H NMR (600 MHz, Chloroform-d) δ 7.52-7.37 (m, 1H), 7.01 (d, J=7.8 Hz, OH), 3.98 (s, 1H), 3.86 (s, 1H), 2.30 (s, 1H), 1.99-1.93 (m, 2H), 1.70 (d, J=12.6 Hz, 1H), 1.62 (d, J=12.3 Hz, 1H), 1.56-1.44 (m, 3H). ¹³C NMR (126 MHz, Chloroform-d) δ 167.06, 158.36, 130.57, 128.19, 127.71, 120.16, 117.30, 61.77, 53.27, 51.99, 40.64, 36.97, 33.04, 28.25.

HRMS: m/z (+H⁺). calc'd: 330.2064, found: 330.1910.

Step 4. Methyl 4-((((adamantan-1-yl)methyl)(methyl)amino)methyl)-3-hydroxybenzoate

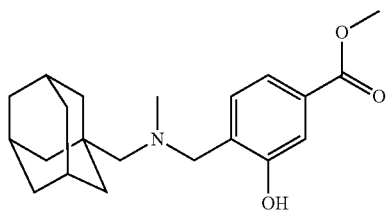 [SMILES: COC(=O)c1ccc(CN(C)CC23CC4CC(CC(C4)C2)C3)c(O)c1]

A solution of 100 mg (0.303 mmol) of methyl 4-(adamantan-1-yl)methyl)amino)methyl)-3-hydroxybenzoate in 3 mL methanol, 0.5 mL formalin, and a drop of acetic acid was stirred for 2 h, then 22.9 mg (0.606 mmol, 2 eq) of sodium borohydride was added and the mixture stirred for another hour. The mixture was concentrated in vacuo, partitioned between ethyl acetate and water, the aqueous layer extracted two more times with ethyl acetate, and the combined organic phases were dried over sodium sulfate. The solvent was removed under reduced pressure and the product was purified by column chromatography. 67.7 mg (0.197 mmol, 65%) of methyl 4-((((adamantan-1-yl)methyl)(methyl)amino)methyl)-3-hydroxybenzoate were obtained as a clear oil that solidified upon standing. $R_f$(25% EtOAc, 75% Hexanes)=0.64; $^1$H NMR (600 MHz, Chloroform-d) δ 7.46 (s, 1H), 7.43 (dd, J=7.8, 1.7 Hz, 2H), 6.99 (d, J=7.8 Hz, 2H), 3.87 (s, 7H), 3.76 (s, 4H), 2.26 (s, 7H), 2.23 (s, 4H), 1.76-1.68 (m, 6H), 1.69-1.60 (m, 7H), 1.56 (d, J=3.0 Hz, 12H). $^{13}$C NMR (126 MHz, Chloroform-d) δ 167.07, 157.93, 130.62, 128.28, 127.37, 120.21, 116.97, 72.04, 64.27, 52.02, 44.84, 41.11, 36.89, 34.44, 28.30. HRMS: m/z (+H$^+$). calc'd: 344.2220, found: 344.2230.

Step 5. 4-((((Adamantan-1-yl)methyl)(methyl)amino)methyl)-3-[F]fluoro-N-hydroxybenzamide

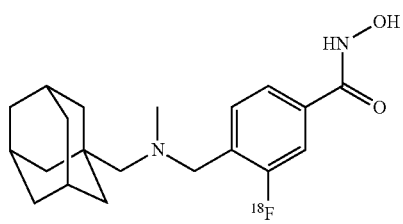

Aqueous [$^{18}$F]fluoride obtained from a cyclotron was passed through a SPE Chromafix 30-PS-HCO$_3$ cartridge that had been previously conditioned with 5.0 mg/mL aqueous potassium carbonate and then washed with 18 mL of Millipore Milli-Q water. The captured [$^{18}$F]fluoride was washed by passing 1 mL of ethanol through the cartridge. At the beginning of the synthesis, 657 mCi were measured on the cartridge. 5 mg of methyl 4-((((adamantan-1-yl)methyl)(methyl)amino)methyl)-3-hydroxybenzoate, 10 mg of Ru(cp)(cod)Cl, and 30 mg N,N-bis-(2,6-diisopropyl)phenyl-2-chloroimidazolium chloride were heated in 250 µL of ethanol at 85° C. for 30 minutes. The resulting solution was passed through the anion exchange cartridge and collected into a dram vial. The cartridge was flushed with 400 µL acetonitrile and 400 µL DMSO and collected into the same vial, which was subsequently sealed with a Teflon lined cap and heated at 130° C. for 30 minutes. Then, 1 mL of THF/MeOH (1:1), 0.4 mL 50% aq. NH$_2$OH, and 0.1 mL 5M NaOH were added at room temperature and the reaction mixture was stirred for 5 minutes. The solution was diluted with water to 10 mL and loaded onto an OASIS® MAX SPE cartridge (60 mg), washed with 5 mL of water and eluted with 2 mL ethanol/0.1M AcOH (1:1) and purified by semi-preparative HPLC (Agilent Eclipse C-18, 9.4×250 mm, 5 µm; flow ramp 0.5 mL/min to 5 mL/min from 0-4 min, then 5 mL/min; 5% ACN in 0.01N NaOH from 0-4 min, then ramp to 70% ACN in 0.01 NaOH at 45 min). The isolated fraction was reformulated on an OASIS® MAX SPE cartridge (60 mg), washed with 5 mL of water and eluted with 2 mL ethanol/0.1M AcOH (1:1), diluted with 8 mL 0.9% saline and neutralized with 0.1 N NaOH to pH 5. Overall, 53.3 mCi were isolated (8.1% non-decay-corrected radiochemical yield) within 94 min.

Example 2A. Purification of 4-((((Adamantan-1-yl)methyl)(methyl)amino)methyl)-3-[$^{18}$F]fluoro-N-hydroxybenzamide Semipreparative HPLC The radiolabeled compound of Example 2 was purified via semipreparative HPLC using the following system and conditions: Agilent Eclipse C-18, 9.4×250 mm, 5 µm; flow ramp 0.5 mL·min$^{-1}$ to 5 mL·min$^{-1}$ from 0-4 min, then 5 mL·min$^{-1}$, 5% ACN in 0.01 N NaOH from 0-4 min, then ramp to 70% ACN in 0.01 NaOH at 45 min.

Analytical HPLC

The radiolabeled compound of Example 2 was purified via analytical HPLC using the following system and conditions: Agilent Eclipse C-18, 4.6×10 mm, 5 µm, flow 2 mL·min$^{-1}$, gradient from 5% ACN/H$_2$O, 0.1% TFA at 0 min to 95% ACN/H$_2$O, 0.1% TFA at 10 min.

Analytical HPLC Co-Injection with Standard

The radiolabeled compound of Example 2 was analyzed via analytical HPLC co-injection with the compound of Example 1, using the following system and conditions: Agilent Eclipse C-18, 4.6×10 mm, 5 µm, flow 2 mL·min$^{-1}$, gradient from 5% ACN/H$_2$O, 0.1% TFA at 0 min to 95% ACN/H$_2$O, 0.1% TFA at 10 min.

Example 3. IC$_{50}$ Assay

IC$_{50}$ measurements were conducted by BPS Biosciences (Table 1) or by Nanosyn (Table 1A) with an established fluorescence assay. Table 1 shows representative IC$_{50}$ values measured for 4-(((((3s)-adamantan-1-yl)methyl)(methyl)amino)methyl)-3-fluoro-N-hydroxybenzamide (Example 1) compared to a known HDAC inhibitor, martinostat (structure shown below).

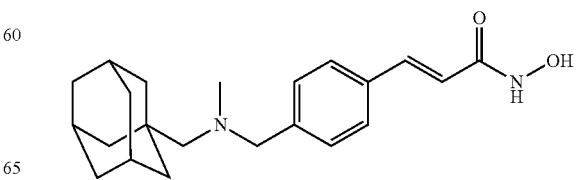

Martinostat

TABLE 1

| | Enzyme | Martinostat | Example 1 | Reference |
|---|---|---|---|---|
| $IC_{50}$ (µM) or Percentage Inhibition | HDAC1 | 0.0062 | >1 mM NI at 1 mM | 0.023* |
| | HDAC2 | 0.022 | >1 mM NI at 1 mM | 0.082* |
| | HDAC3 | 0.0071 | >1 mM NI at 1 mM | 0.013* |
| | HDAC4 | >1 39% at 1 µM | 11.3 | 2.9† |
| | HDAC5 | 0.98 | 19 | 1.7† |
| | HDAC6 | 0.048 | 0.06 | 0.01* |
| | HDAC7 | >1 NI* at 1 µM | 4.7 | 1.6† |
| | HDAC8 | >1 NI* at 1 µM | 8.5 | 0.546† |
| | HDAC9 | >1 12% at 1 µM | 5.2 | 3.8† |
| | HDAC10 | 0.0089 | >1 mM 21% at 1 mM | 0.03* |
| | HDAC11 | >1 17% at 1 µM | 10 | 10† |

*SAHA
†TSA

Table 1A shows HDAC6 $IC_{50}$ values measured for the compounds of Example 1 and 8-25.

TABLE 1A

| Example | HDAC6 $IC_{50}$ (µM) |
|---|---|
| 1 | 0.016(0.023,0.016) |
| 8 | 0.089 |
| 9 | 0.0136 |
| 10 | 1.02 |
| 11 | 0.574 |
| 12 | 0.081 |
| 13 | 0.0267 |
| 14 | 0.0748 |
| 15 | 0.0599 |
| 16 | 0.012 |
| 17 | 0.035 |
| 18 | 1.38 |
| 19 | 0.323 |
| 20 | 0.290 |

TABLE 1A-continued

| Example | HDAC6 $IC_{50}$ (µM) |
|---|---|
| 21 | 0.213 |
| 22 | 0.121 |
| 23 | 0.149 |
| 24 | 1.19 |
| 25 | 0.084 |

Table 1B shows a comparison of HDAC1-11 $IC_{50}$ values measured for the compounds of Example 1 compared to the following compounds:

A=Martinostat (Caliper (microfluidics mobility shift detection) by Nanosyn (same run, duplicates));

B=

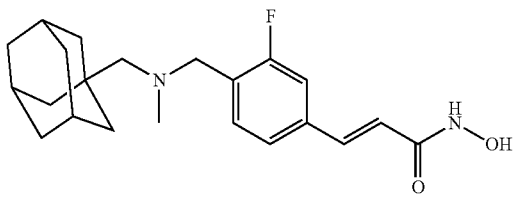 [SMILES: CN(Cc1ccc(/C=C/C(=O)NO)cc1F)CC12CC3CC(CC(C3)C1)C2]

(see e.g., WO 2015/058106; Fluorescent-intensity-based enzymatic assay, multiple runs; duplicates);

C=

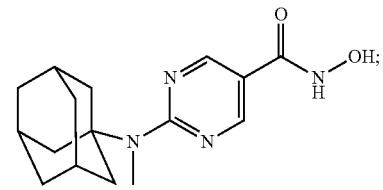 [SMILES: CN(c1ncc(C(=O)NO)cn1)C12CC3CC(CC(C3)C1)C2]

D=Tubastatin A (see e.g., Butler et al, *JACS* (2010) 132:10842-10846);

E=ACY-1215 (see e.g., Santo et al., *Blood* (2012) 119: 2579); and

F=CI-994 (see e.g., Seo et al., *ACS Chem. Neurosci.* 2014, 5(7):588-596).

TABLE 1B

| Class | HDAC | Ex. 1[a] | A | B | C | D | E | F | Ex. 1[b] |
|---|---|---|---|---|---|---|---|---|---|
| I | HDAC1 (nM) | >1000 | 1.2 | 17 | 20 | 16400 | 58 | 41 | >1000 |
| | HDAC2 (nM) | >1000 | 4.0 | 73 | 65 | >30 | 48 | 147 | >1000 |
| | HDAC3 (nM) | >1000 | 0.3 | 23 | 24 | >30 | 51 | 46 | >1000 |
| | HDAC8 (nM) | >1000 | 750 | >1000 | 364 | 850 | >1000 | >33 | 8500 |
| IIa | HDAC4 (nM) | >1000 | 240 | >1000 | 34 | >30 | >1000 | >33 | 11300 |
| | HDAC5 (nM) | >1000 | 75 | >1000 | 121 | >30 | >1000 | >33 | 19000 |
| | HDAC7 (nM) | >1000 | >1000 | >1000 | 36 | >30 | >1000 | >33 | 4700 |
| | HDAC9 (nM) | >1000 | >1000 | >1000 | 52 | >30 | >1000 | >33 | 5200 |

TABLE 1B-continued

| Class | HDAC | Ex. 1[a] | A | B | C | D | E | F | Ex. 1[b] |
|---|---|---|---|---|---|---|---|---|---|
| IIb | HDAC6 (nM) | 17 | 1.8 | 180 | 33 | 15 | 5.0 | >33 | 60 |
|  | HDAC10 (nM) | >1000 | 2.0 | 33 | 25 | >30 | >1000 | 1440 | >1000 |
| IV | HDAC11 (nM) | 900 | >1000 | >1000 | 3600 | >30 | >1000 | 2830 | 10000 |

[a] $IC_{50}$ measured by Nanosyn
[b] $IC_{50}$ measured by BPS

Table 1C shows a comparison of the HDAC6 selectivity and potency for the compound of Example 1 compared to known compounds Tubastatin A, ACY-1215 (ricolinostat), and CI-994 (i.e., tacedinaline). +++=verified brain-penetrant; +/−=modest to no brain uptake; −=no brain uptake.

TABLE 1C

| Compound | Selectivity (HDAC6 vs. Class I HDACs) | Potency (HDAC6 $IC_{50}$ in nM) | Brain-penetrant? |
|---|---|---|---|
| Example 1 | 140x | 60[b] | +++ |
| Tubastatin A | 57x | 15 | +/− |
| ACY-1215 | 10x | 5 | − |
| CI-994 | N/A[a] | >30,000 | − |

[a] pan-Class I HDAC inhibitor
[b] $IC_{50}$ measured by BPS

Table 1D shows additional pharmacokinetic data measured for the compound of Example 1.

TABLE 1D

| Parameter | Result | | | | | |
|---|---|---|---|---|---|---|
| Selectivity (MMPs) | No inhib of MMP-1,2,3,9,or -14 at 10 µM | | | | | |
| Safety (DiscoverX Safety47 Panel[a]) | No effect at 10 µM | | | | | |
| Microsome stability (half-life, min) | 19 (hu); <10 (rat); <10 (mouse) | | | | | |
| Hepatocyte stability (half-life, min) | 20 (hu) | | | | | |
| Oral Bioavailability | 10% | | | | | |
| PK (C57BL/6 mice; male; n) | iv (1 mg/kg) | | ip (5 mg/kg) | | po (5mg/kg) | |
|  | plasma | brain | plasma | brain | plasma | brain |
| AUC (µM/L*hr) | 0.12 | 1.33 | 0.14 | 1.08 | 0.06 | 0.08 |
| Cmax (µM) | 0.17 | 1.9 | 0.27 | 1.61 | 0.46 | 0.76 |
| $T_{1/2}$ (hr) | — | — | 0.08 | 0.08 | 0.25 | 0.25 |
| Brain:Plasma ratio (AUC) | 11 | 6 | 7.7 | | 8.2 | |

[a] DiscoverX Safety47 panel encompasses 78 assays: 24 GPCRs and 2 nuclear hormone receptors, in agonist and antagonist modes, 3 neurotransmitter transporters, 8 ion channels, 4 kinases and 6 other enzymes (e.g., COX1/2).

Example 4. Acetylation Level Assay

Human iPSC-derived neural progenitor cells from a healthy control subject fibroblast cell line GM08330 (Coriell Institute for Medical Research) were generated using previously reported methods and treated with DMSO or a solution of HDAC inhibitor (ACY1215, final concentration 5 µM; Example 1, CI-994, Tubastatin A, final concentration 10 µM) for 6 h at 37° C. Lysis of cell pellets (n=3 per condition) was performed in radioimmunoprecipitation assay (RIPA) buffer (Boston BioProducts #BP-115) with EDTA-free protease inhibitors (Sigma #4693159001). The lysates were centrifuged at 18,000 rpm at 4° C. for 15 min, and the supernatants were collected. The protein concentration was determined by BCA assay (Thermo Scientific #23227). Western blot analysis was conducted on samples adjusted to 6 µg of total protein/replicate.

To confirm the high selectivity suggested by the $IC_{50}$ values described in Example 3, the acetylation levels of a substrate and two non-substrates of HDAC6 in an IPS derived human neuroprogenitor cell line were investigated, as described above. Treatment with the compound of Example 1 in comparison to other tool compounds and quantification of the acetylation state of α-Tubulin and histones (specifically H3K9 and H4K12) confirmed the selectivity for HDAC6 on a functional level, as shown in FIG. 1.

Tubastatin A and ACY1215 have both been shown to inhibit HDAC6. Both compounds increased the amount of cellular acetyl-α-Tubulin, while a class-1 selective HDAC inhibitor, CI-994 did not increase tubulin acetylation. The compound of Example 1 also increased the amount of cellular acetyl tubulin, demonstrating its engagement with HDAC6, as shown in FIG. 1.

Histone acetylation remained unaltered for the compound of Example 1, as it does for the highly HDAC6 selective agent Tubastatin A. ACY1215 showed poor selectivity for HDAC6, leading to significantly increased acetylation of H4K12 through inhibition of other HDAC isoforms. Histone acetylation on both H3K9 and H4K12 was significantly increased in cells treated with CI-994. In conclusion, the changes in cellular protein acetylation in response to HDAC inhibitor treatment confirmed the functional selectivity of Example 1 for HDAC6, as shown in FIG. 1.

Example 5. Western Blotting

Proteins were separated on Criterion Stain-Free 4-20% gels (Biorad 567-8095) at 200V for 50 min. Proteins were transferred to low fluorescence PVDF membrane (Biorad 162-0264) at 0.14 amps for 60 min. Gels and membranes were imaged with a Chemidoc XRS system (Biorad 170-8265) for quality control purposes. Membranes were processed as follows: blocked in Tris buffered saline+Tween 20 (TBST, 0.1% Tween 20) containing 5% blocker (Biorad 170-6404) overnight at 4° C. The following steps were performed at room temperature: The membrane was washed in TBST, incubated with primary antibodies in TBST containing 1% blocker (acetyl histone H3 lysine 9: EMD Millipore 06-942-S 1:4000, acetyl histone H4 lysine 12: EMD Millipore 07-595 1:4000) for 60 min, washed in TBST, incubated with secondary antibody in TBST containing 1% blocker (anti-rabbit-HRP: Cell Signaling #7074S 1:5000, anti-mouse-HRP: Cell Signaling #7076S 1:5000) for 60 min, washed in TBST, developed with ECL prime western blotting detection reagent (GE RPN2232), and visualized with a Chemidoc XRS system. Western blot images were converted from Image Lab 5.2.1 (.scn) files to 600 dpi .tif files. The images were opened in ImageJ. Images were converted to 8-bit and background was subtracted with a rolling ball radius of 50.0 pixels. Images were inverted and mean band intensity was quantified with the measurement tool.

Example 6. Autoradiography

Figure 3:
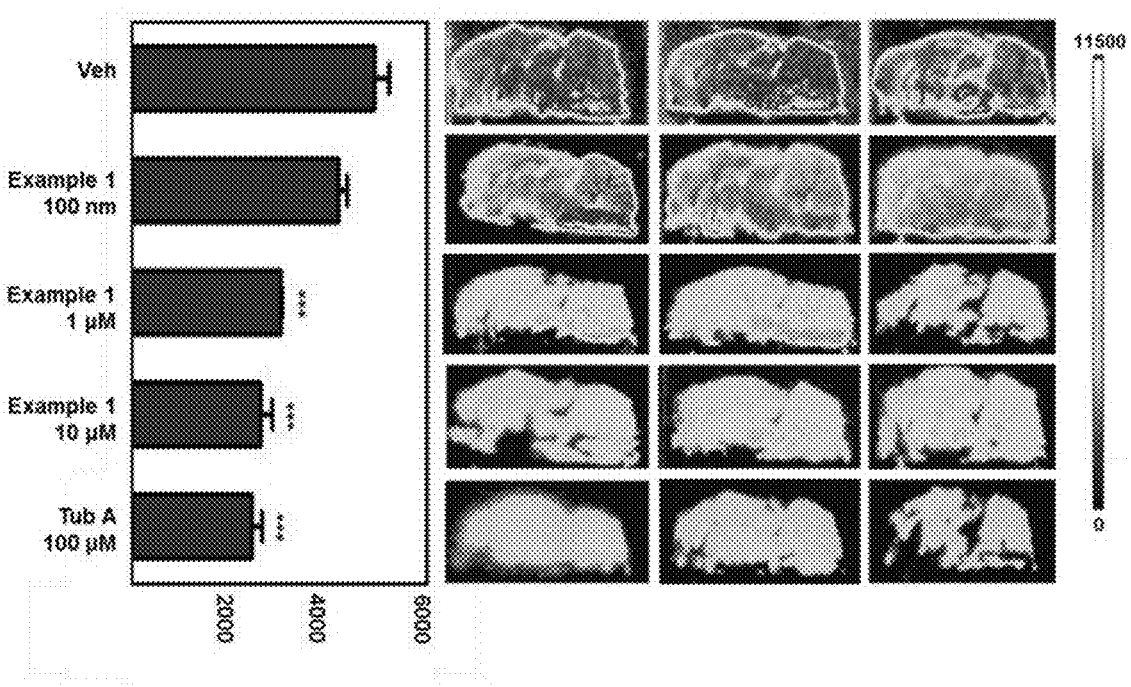
FIG. 3 shows representative autoradiography images of sagittal slices of Sprague-Dawley rat brains exposed to the radiolabeled compound of Example 2 in the presence of the compound of Example 1 or Tubastatin.

Selectivity of the Example 1 in brain tissue was demonstrated using autoradiography (FIG. 3). Sagittal slices of Sprague-Dawley rat brains were sectioned (10 μm) with a cryostat (Thermo Scientific HM550) and mounted onto ColorFrost Plus microscope slides (Fisher Scientific 12-550-18) and stored at −20° C. The slides were submerged in baths of 50 mL of buffer (100 mM Tris, 50 mM NaCl, pH 7.5) at room temperature containing either 50 μL of DMSO or a solution of blocking compound in DMSO (Example 1 at a final concentration of 100 nM, 1 μM and 10 μM, and Tubastatin A at a final concentration of 100 μM). After 15 min, 50 μCi of the radiolabeled compound of Example 2 was added to each bath. After 15 minutes, all slides were washed by dipping 10× into buffer and subsequently submerged in 50 mL baths of buffer at 4° C. for 5 minutes. The slides were dried at 35° C. in a vacuum chamber. A phosphorus screen (Perkin Elmer 7001723) was exposed with the slides for 45 minutes and subsequently imaged with a Cyclone Plus Storage Phosphor (Perkin Elmer) detector. ImageJ was used to apply a Gaussian blur (3.0 radius) smoothing and a lookup table (Royal) with equivalent thresholds for brightness was applied. Raw intensity values from gray and white matter were quantified with the ImageJ measurement tool.

Slices of rat brain tissue were exposed to the radiolabeled compound of Example 2 in the presence of Example 1 or Tubastatin. At 1 μM of Example 1, binding was significantly reduced. Tubastatin A, an HDAC6 selective compound, was able to reduce the amount of bound radioactivity to the same background as 10 μM Example 1. These data indicate that the binding to brain tissue occurs with selectivity for HDAC6.

Example 7. PET/CT Imaging

Rat Imaging 8 male Sprague-Dawley rats (Charles River Laboratories) were used for PET imaging. Anesthesia was achieved with isoflurane in medical oxygen carrier (3% for induction, 2% for maintenance). For intravenous administration, a catheter with an extension line was placed in a lateral tail vein. Each animal received a bolus injection of either vehicle (1:1:8 DMSO/Tween80/saline) or blocking agent in solution (1 mg/kg, 1 mg/mL in 1:1:8 DMSO/Tween80/saline) immediately prior to injection of the radiotracer.

After injection of a radiotracer bolus (~700 pCi Example 2) a 90 min dynamic PET scan was acquired in pairs for all animals. PET scans were performed on a GammaMedica Triumph PET/CT/SPECT scanner, corrected for attenuation with a μ-map derived from the corresponding CT image, which was acquired immediately following the PET scan. The dynamic PET data was binned into 38 timeframes (8×15 s, 8×1 min, 10×2 min, 12×5) and reconstructed individually via an iterative MLEM (maximum likelihood expectation maximization) algorithm in 16 iterations.

PET images were coregistered to the CT image acquired from the same animal using AMIDE Data sets were cropped and all further image analysis was conducted using PMOD 3.3 (PMOD Technologies, Zurich, Switzerland). For maximum consistency, the data were coregistered to the Schiffer Px Rat rat brain template and data was derived from a whole brain VOI (volumes of interest) for time activity curves.

Primate Imaging

PET-MR imaging was performed in anesthetized (ketamine, isoflurane) baboon (*Papio anubis*) to minimize discomfort. Audio, video, and tactile enrichment was provided on a daily basis to promote psychological well-being. No nonhuman primates were euthanized to accomplish the research presented.

PET-MR images were acquired in a Biograph mMR scanner (Siemens, Munich, Germany) and PET compatible 8-channel coil arrays for nonhuman primate brain imaging with a PET resolution of 5 mm and field of view of 59.4 and 25.8 cm (transaxial and axial, respectively). Dynamic PET image acquisition was initiated followed by administration of the radiotracer, intravenously. An MEMPRAGE sequence began after 30 min of the baseline scan for anatomic co-registration. To characterize the specific binding, a second imaging experiment was carried out in which unlabeled Example 1 was co-administered intravenously at the start of acquisition. Dynamic data from the PET scans were recorded in list mode and corrected for attenuation. Baboon data were reconstructed using a 3D-OSEM method resulting in a fwhm resolution of 4 mm.

Figure 4:
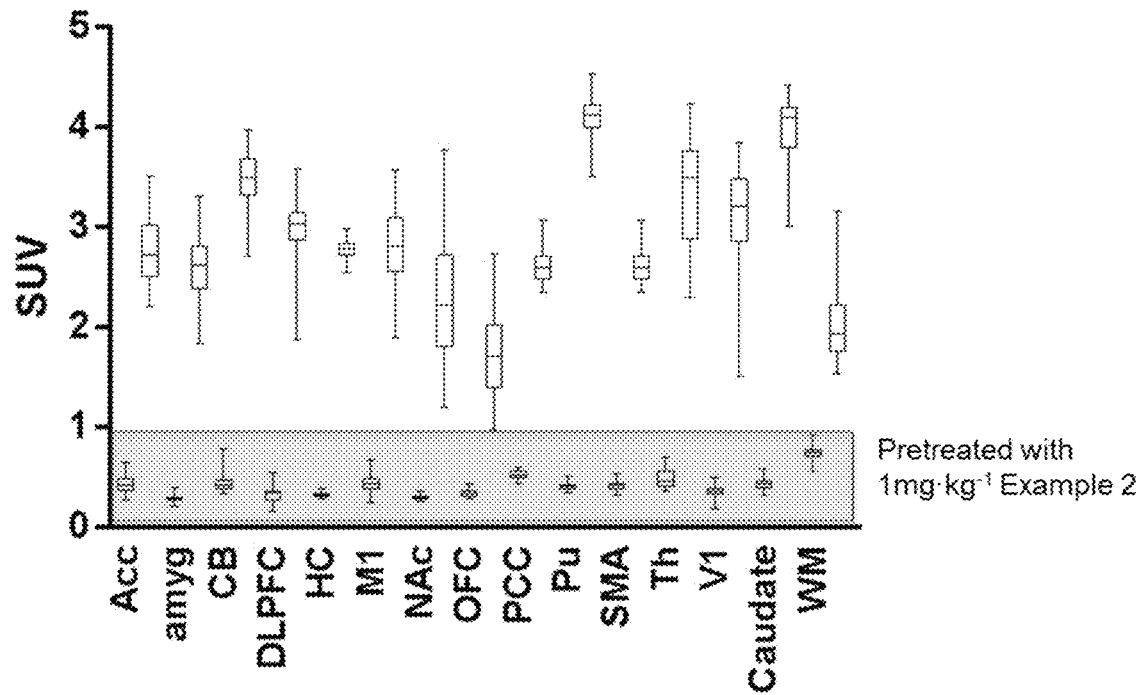
FIG. 4 shows SUV analysis of 15 regions within the baboon brain using the black baboon atlas, comparison of baseline and pretreated distribution. Each region of interest (ROI) is shown as a distribution of SUV values (averaged 60-120 min) of each voxel within the ROI. ACC=Anterior cingulate cortex, amgyg=amygdala, CB=cerebellum, DLPFC=dorsolateral prefrontal cortex, HC=hippocampus, M1=primary motor area, NAc=Nucleus accumbens, OFC=orbitofrontal cortex, PCC=posterior cingulate cortex, Pu=putamen, SMA=supplementary motor area, Th=Thalamus, V1=primary visual cortex, WM=white matter.
Figure 5:
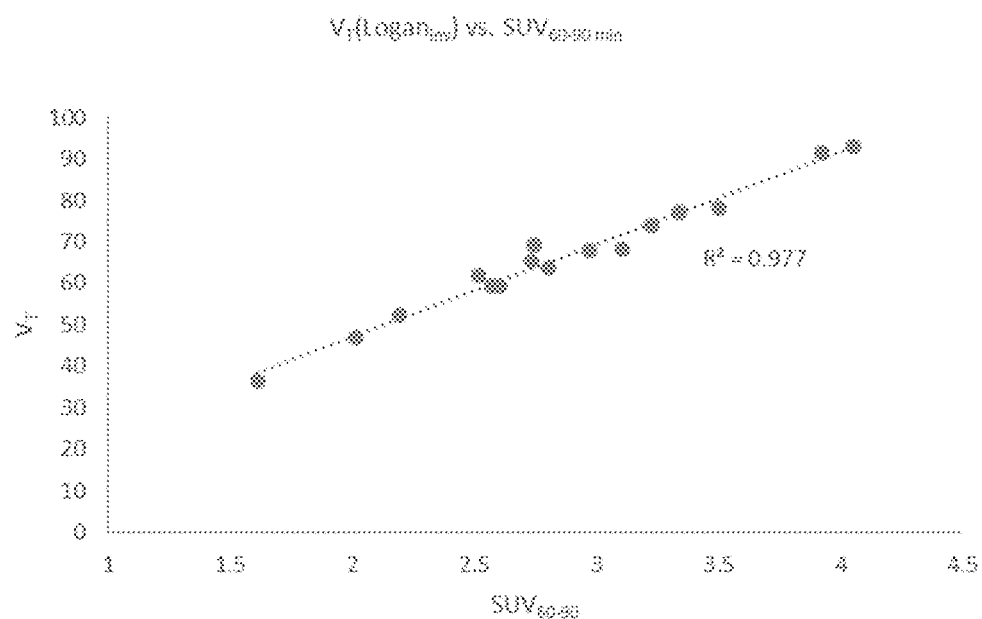
FIG. 5 shows SUV and VT comparison. Region of interest data for Example 2 are plotted as SUV values (averaged 60-120 min) versus distribution volume (Vt) to show the linearity of the two measures. This data supports the potential use of a reference strategy for quantification of signal.
Figures 6A, 6B:
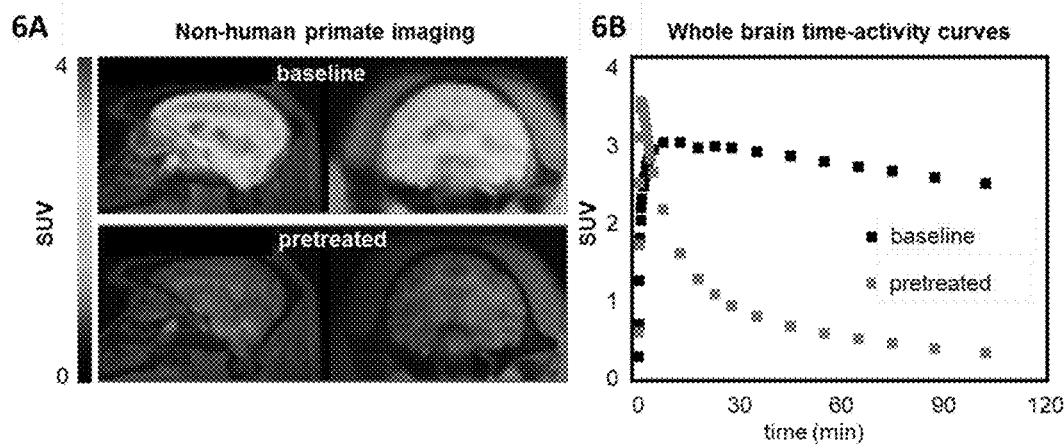
FIGS. 6A-6B show the average uptake images and time-activity curves for the comparison between baseline (Example 2) PET scan and pretreated PET scan, where the target was presaturated by administration of the non-radiolabeled form of Example 1.
Figures 7A, 7B:
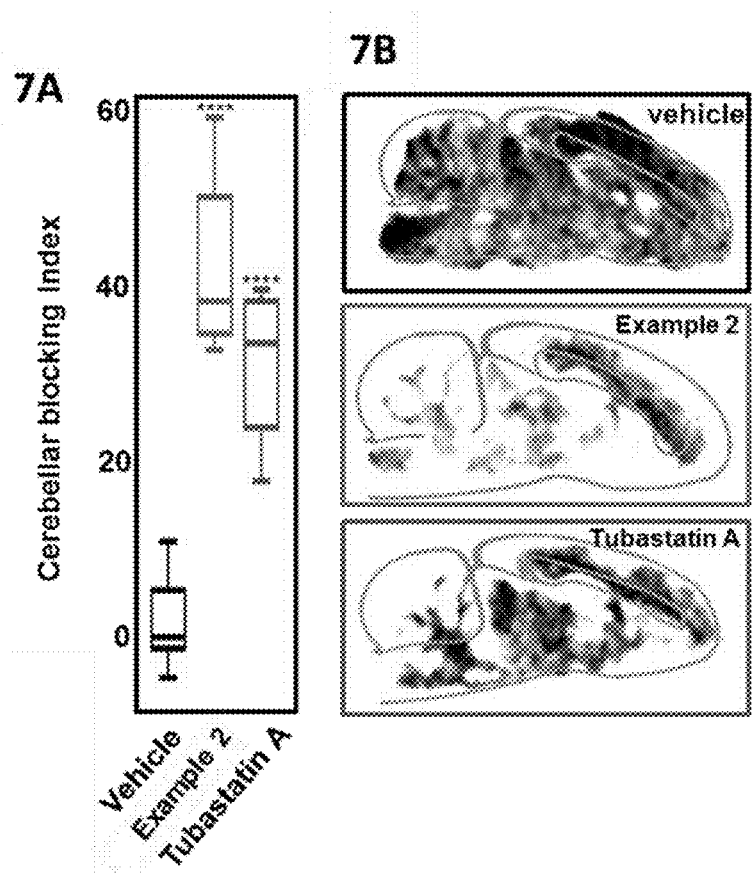
FIGS. 7A-7B shows in vitro autoradiography data from competition assays.

PET imaging was additionally performed in baboon brain. FIG. 4 shows analysis of 15 regions within baboon brain using the black baboon atlas, comparison of baseline and pretreated distribution. Each region of interest (ROI) is shown as a distribution of SUV values (averaged 60-120 min) of each voxel within the ROI. ACC=Anterior cingulate cortex, amgyg=amygdala, CB=cerebellum, DLPFC=dorsolateral prefrontal cortex, HC=hippocampus, M1=primary motor area, NAc=Nucleus accumbens, OFC=orbitofrontal cortex, PCC=posterior cingulate cortex, Pu=putamen, SMA=supplementary motor area, Th=Thalamus, V1=primary visual cortex, WM=white matter. FIG. 5 shows a comparison of SUV and VT derived from a metabolite corrected arterial plasma input function (Feng interpolation) and calculated via an invasive Logan plot.

Statistical Analysis

Figure 2A:
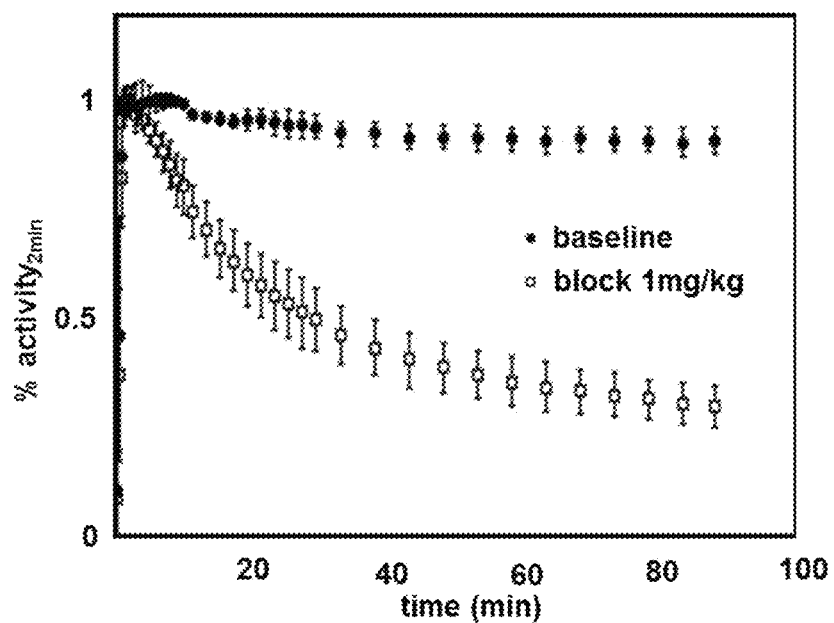
FIG. 2A shows averaged (n=3) time-activity curves of a whole-brain ROI of Sprague-Dawley rats injected with [$^{18}$F] radiolabeled 4-(((((3s)-adamantan-1-yl)methyl)(methyl)amino)methyl)-3-fluoro-N-hydroxybenzamide (Example 2). In the blocked animals, 1 mg/kg of unlabeled 4-(((((3s)-adamantan-1-yl)methyl)(methyl)amino)methyl)-3-fluoro-N-hydroxybenzamide (Example 1) was injected immediately prior to radiotracer administration, baseline animals treated with vehicle.
Figure 2B:
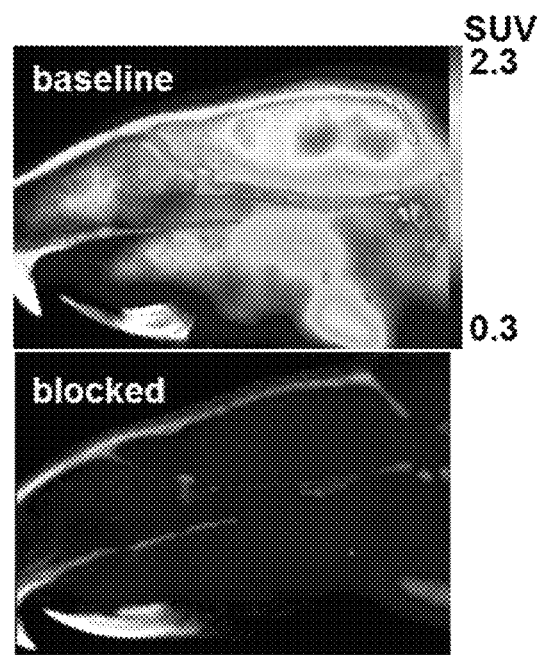
FIG. 2B shows PET images of Sprague-Dawley rats injected with [$^{18}$F] radiolabeled 4-(((((3s)-adamantan-1-yl)methyl)(methyl)amino)methyl)-3-fluoro-N-hydroxybenzamide (Example 2). The images show sagittal slices summed from 30-90 minutes.

Statistical tests were performed using GraphPad Prism (Prism6, GraphPad Software Inc.). For PET imaging analyses, a nonparametric Friedman test (a=0.05 with Dunn's multiple comparisons correction) was performed to compare SUV60-90 min between brain regions (FIGS. 2A-2B). A Pearson correlation analysis was performed between VT and SUV 60-90 min values for the 14 VOIs (FIG. 2B) to evaluate whether an image-based outcome measurement (SUV60-90 min) was an appropriate surrogate to that estimated with the full kinetic modeling data (VT). Differences in postmortem HDAC expression levels as well as differences in nuclear density, size, and total area between the SFG and the CC were evaluated with an unpaired t-test. Differences in postmortem HDAC expression levels between the dorsolateral prefrontal cortex, hippocampus, and anterior cingulate were evaluated with an ordinary one-way ANOVA (a=0.05 with Tukey's multiple comparisons correction). Differences in histone acetylation and gene expression levels as compared to vehicle were evaluated with a repeated-measures two-way ANOVA (a=0.05 with Dunnett's multiple comparisons correction). In autoradiographic assays, differences between [$^{11}$C]Martinostat baseline and blocking intensity values, in gray matter and white matter, were evaluated with an ordinary two-way ANOVA (a=0.05 with Sidak's multiple comparisons correction).

The radiolabeled compound of Example 2 exhibited excellent brain uptake and retention. Treatment of the animals with non-radioactive compound of Example 1 at 1 mg/kg led to blocking of brain uptake, indicative of specific binding. Treatment of the animals with 1 mg/kg the compound of Example 1, 30-minutes post radiotracer administration, demonstrated a clear deflection of the time activity curve, indicating the reversibility of target engagement. The off-rate in preclinical PET appeared to be slow, but within the range of known, kinetically well-characterized radiotracers such as [$^{11}$C]Martinostat.

Example 8. 4-((((Adamantan-1-yl)methyl)amino)methyl)-2-fluoro-N-hydroxybenzamide

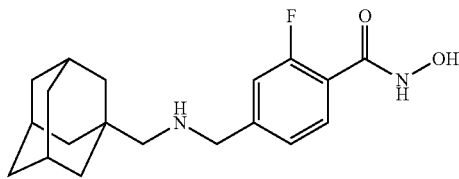 [SMILES: O=C(NO)c1ccc(CNCC23CC4CC(CC(C4)C2)C3)cc1F]

To a solution of Intermediate 1 (10 mg, 30 μmol, 1.0 eq) in 0.4 mL 1:1 THF/MeOH was added 0.1 mL hydroxylamine (50% aq) and aqueous NaOH (5.0 M, 0.05 mL). The reaction mixture was stirred for 35 min, then diluted to 1 mL with water and purified by semipreparative HPLC (gradient: 20% MeOH in 0.025% TFA to 95% MeOH over 45 min at 5 mL/min, Luna C-18). The methanol was removed in vacuo and the residual aqueous solution was lyophilized to yield the 9.7 mg (22 μmol, 72%) of the title product as a white, fluffy solid. $^1$H NMR (500 MHz, DMSO-d$_6$) δ 11.06 (s, 1H), 9.30 (s, 1H), 8.64 (s, 2H), 7.61 (t, J=7.6 Hz, 1H), 7.48 (d, J=10.9 Hz, $^1$H), 7.40 (d, J=7.9 Hz, 1H), 4.20 (s, 2H), 2.77 (s, 2H), 1.96 (d, J=4.8 Hz, 3H), 1.72-1.55 (m, 6H), 1.52 (d, J=2.9 Hz, 6H).

Example 9. 4-((((Adamantan-1-yl)methyl)amino)methyl)-3,5-difluoro-N-hydroxybenzamide

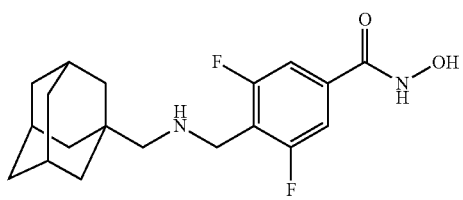 [SMILES: O=C(NO)c1cc(F)c(CNCC23CC4CC(CC(C4)C2)C3)c(F)c1]

To a solution of Intermediate 2 (10 mg, 30 μmol, 1.0 eq) in 0.4 mL 1:1 THF/MeOH was added 0.1 mL hydroxylamine (50% aq) and aqueous NaOH (5.0 M, 0.05 mL). The reaction mixture was stirred for 35 min, then diluted to 1 mL with water and purified by semipreparative HPLC (gradient: 20% MeOH in 0.025% TFA to 95% MeOH over 45 min at 5 mL/min, Luna C-18). The methanol was removed in vacuo and the residual aqueous solution was lyophilized to yield the 5.2 mg (11 μmol, 37%) of the title product as a white, fluffy solid. $^1$H NMR (500 MHz, DMSO-d$_6$) δ 11.53 (s, 1H), 9.38 (s, 1H), 8.63 (s, 2H), 7.56 (d, J=8.2 Hz, 2H), 4.25 (s, 2H), 2.77 (s, 2H), 1.96 (s, 3H), 1.70-1.52 (m, 12H).

Example 10. 4-((((adamantan-1-yl)methyl)amino)methyl)-3-trifluoromethyl-N-hydroxybenzamide

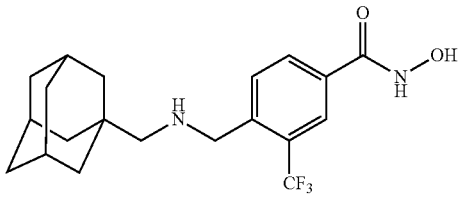 [SMILES: O=C(NO)c1ccc(CNCC23CC4CC(CC(C4)C2)C3)c(C(F)(F)F)c1]

To a solution of Intermediate 3 (10 mg, 26 μmol, 1.0 eq) in 0.4 mL 1:1 THF/MeOH was added 0.1 mL hydroxylamine (50% aq) and aqueous NaOH (5.0 M, 0.05 mL). The reaction mixture was stirred for 35 min, then diluted to 1 mL with water and purified by semipreparative HPLC (gradient: 20% MeOH in 0.025% TFA to 95% MeOH over 45 min at 5 mL/min, Luna C-18). The methanol was removed in vacuo and the residual aqueous solution was lyophilized to yield the 7.3 mg (15 μmol, 57%) of the title product as a white, fluffy solid. $^1$H NMR (500 MHz, DMSO-d$_6$) δ 11.59 (s, 1H), 9.32 (s, 1H), 8.75 (s, 2H), 8.15 (d, J=8.9 Hz, 2H), 7.94 (d, J=8.1 Hz, 1H), 4.34 (s, 2H), 2.76 (s, 2H), 1.96 (s, 3H), 1.78-1.34 (m, 12H).

Example 11. 4-((((adamantan-1-yl)methyl)amino)methyl)-3-methyl-N-hydroxybenzamide

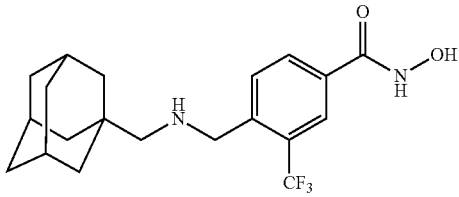 [SMILES: O=C(NO)c1ccc(CNCC23CC4CC(CC(C4)C2)C3)c(C(F)(F)F)c1]

To a solution of Intermediate 4 (10 mg, 30 μmol, 1.0 eq) in 0.8 mL 1:1 THF/MeOH was added 0.1 mL hydroxylamine (50% aq) and aqueous NaOH (5.0 M, 0.05 mL). The reaction mixture was stirred for 35 min, then diluted to 1 mL with water and purified by semipreparative HPLC (gradient: 20% MeOH in 0.025% TFA to 95% MeOH over 45 min at 5 mL/min, Luna C-18). The methanol was removed in vacuo and the residual aqueous solution was lyophilized to yield the 8.3 mg (19 μmol, 63%) of the title product as a white, fluffy solid. $^1$H NMR (500 MHz, DMSO-d$_6$) δ 11.26 (s, 1H), 9.09 (s, 1H), 8.50 (s, 2H), 7.71-7.59 (m, 2H), 7.55 (d, J=7.9 Hz, 1H), 4.19 (d, J=5.9 Hz, 2H), 2.70 (d, J=7.6 Hz, 2H), 2.38 (s, 3H), 1.96 (s, 3H), 1.75-1.50 (m, 12H).

Example 12. 4-(((((3r,5r,7r)-adamantan-1-yl)methyl)(methyl)amino)methyl)-N-hydroxybenzamide

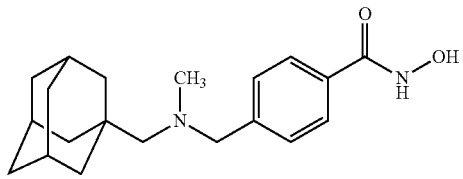 [SMILES: CN(Cc1ccc(C(=O)NO)cc1)CC12CC3CC(CC(C3)C1)C2]

Step 1. methyl 4-(((((3r,5r,7r)-adamantan-1-yl)methyl)(methyl)amino)methyl)benzoate A solution of Intermediate 8 (0.20 g, 0.64 mmol) in 3 ml 0.5 mL formalin and a drop of acetic acid were stirred for 2 h, then 200 mg sodium borohydride was added portionwise and the reaction was stirred 2 h. The mixture was concentrated in vacuo, partitioned between ethyl acetate and water, the aqueous layer extracted two more times with ethyl acetate and the combined organic phases were dried over sodium sulfate. The solvent was removed under reduced pressure and the product was purified by column chromatography. Methyl 4-(((((3r,5r,7r)-adamantan-1-yl)methyl)(methyl)amino)methyl)benzoate (80 mg, 0.26 mmol, 41%) was obtained as a clear oil that solidified upon standing.

Step 2. 4-(((((3r,5r,7r)-adamantan-1-yl)methyl)(methyl)amino)methyl)-N-hydroxybenzamide

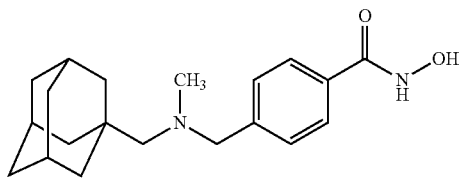 [SMILES: CN(Cc1ccc(C(=O)NO)cc1)CC12CC3CC(CC(C3)C1)C2]

To a solution of methyl 4-(((((3r,5r,7r)-adamantan-1-yl)methyl)(methyl)amino)methyl)benzoate (50 mg, 0.15 mmol, 1 eq) in 2 mL 1:1 THF/MeOH was added 0.50 mL hydroxylamine (50% aq) and aqueous NaOH (5.0 M, 0.10 mL). The reaction mixture was stirred for 2 h at room temperature (RT), then 80 μL 6N HCl was added. The product was extracted with DCM, the organic layer washed with water, dried over sodium sulfate and concentrated in vacuo. The oily residue was triturated with ether. $^1$H NMR (500 MHz, DMSO-$d_6$) δ 11.34 (s, 1H), 9.14 (s, 1H), 8.77 (s, 1H), 7.83 (d, J=8.0 Hz, 2H), 7.64 (d, J=8.0 Hz, 2H), 4.48-4.23 (m, 2H), 2.88 (d, J=4.8 Hz, 5H), 1.90 (s, 3H), 1.66-1.42 (m, 12H).

Example 13. 6-((((adamantan-1-yl)methyl)amino)methyl)-N-hydroxynicotinamide

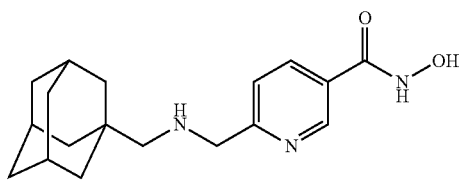 [SMILES: O=C(NO)c1ccc(CNCC23CC4CC(CC(C4)C2)C3)nc1]

To a solution of Intermediate 5 (10 mg, 31 μmol, 1.0 eq) in 0.4 mL 1:1 THF/MeOH was added 0.1 mL hydroxylamine (50% aq) and aqueous NaOH (5.0 M, 0.05 mL). The reaction mixture was stirred for 35 min, then diluted to 1 mL with water and purified by semipreparative HPLC (gradient: 20% MeOH in 0.025% TFA to 95% MeOH over 45 min at 5 mL/min, Luna C-18). The methanol was removed in vacuo and the residual aqueous solution was lyophilized to yield the 12 mg (28 μmol, 90%) of the title product as a white, fluffy solid. 1H NMR (500 MHz, DMSO-d6) δ 11.50 (s, 1H), 10.14 (s, 1H), 8.96 (s, 2H), 8.82 (s, 1H), 8.23-8.15 (m, 1H), 7.60 (d, J=8.2 Hz, 1H), 4.37 (d, J=12.5 Hz, 2H), 2.63 (s, 2H), 1.97 (s, 3H), 1.70-1.58 (m, 6H), 1.56 (d, J=2.7 Hz, 6H).

Example 14. 4-((((adamantan-1-yl)methyl)amino)methyl)-3-chloro-N-hydroxybenzamide

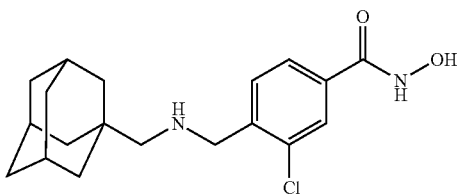 [SMILES: O=C(NO)c1ccc(CNCC23CC4CC(CC(C4)C2)C3)c(Cl)c1]

To a solution of Intermediate 6 (10 mg, 29 μmol, 1.0 eq) in 0.4 mL 1:1 THF/MeOH was added 0.1 mL hydroxylamine (50% aq) and aqueous NaOH (5.0 M, 0.05 mL). The reaction mixture was stirred for 35 min, then diluted to 1 mL with water and purified by semipreparative HPLC (gradient: 20% MeOH in 0.025% TFA to 95% MeOH over 45 min at 5 mL/min, Luna C-18). The methanol was removed in vacuo and the residual aqueous solution was lyophilized to yield the 8.7 mg (25 μmol, 86%) of the title product as a white, fluffy solid. 1H NMR (500 MHz, DMSO-d6) δ 11.45 (s, 1H), 9.25 (s, 1H), 8.63 (s, 2H), 7.85 (d, J=45.4 Hz, 3H), 4.31 (s, 2H), 2.74 (s, 2H), 1.96 (s, 3H), 1.74-1.47 (m, 12H).

Example 15. 4-((((adamantan-1-yl)methyl)amino)methyl)-3-bromo-N-hydroxybenzamide

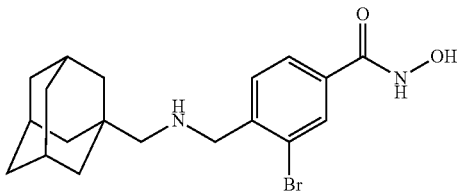 [SMILES: O=C(NO)c1ccc(CNCC23CC4CC(CC(C4)C2)C3)c(F)c1]

To a solution of Intermediate 7 (10 mg, 26 μmol, 1.0 eq) in 0.4 mL 1:1 THF/MeOH was added 0.1 mL hydroxylamine (50% aq) and aqueous NaOH (5.0 M, 0.05 mL). The reaction mixture was stirred for 35 min, then diluted to 1 mL with water and purified by semipreparative HPLC (gradient: 20% MeOH in 0.025% TFA to 95% MeOH over 45 min at 5 mL/min, Luna C-18). The methanol was removed in vacuo and the residual aqueous solution was lyophilized to yield the 11 mg (22 μmol, 85%) of the title product as a white, fluffy solid. 11H NMR (500 MHz, DMSO-d6) δ 11.45 (s, 1H), 9.25 (s, 1H), 8.73 (s, 2H), 8.05 (s, 1H), 7.80 (m, 2H), 4.30 (s, 2H), 2.74 (s, 2H), 1.96 (s, 3H), 1.74-1.52 (m, 12H).

Example 16. 4-(((((3r,5r,7r)-adamantan-1-yl)methyl) amino)methyl)-3-fluoro-N-hydroxybenzamide

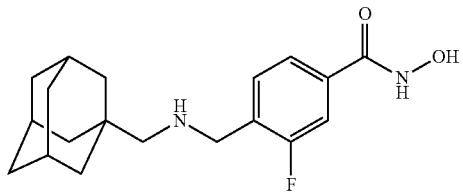

To a solution of methyl 4-(((((3s)-adamantan-1-yl) methyl)amino)methyl)-3-fluorobenzoate (see e.g., Strebl et al., *ACS Cent. Sci.* 2017, 3(9):1006-1014); 102 mg, 0.31 mmol, 1eq) in 2 mL 1:1 THF/MeOH was added 0.50 mL hydroxylamine (50% aq, 0.25 g, 3.6 mmol, 12 eq) and aqueous NaOH (5.0 M, 0.10 mL, 0.50 mmol, 1.6 eq). The reaction mixture was stirred for 7 h, then 100 µL 2.5N HCl was added. The product was purified by preparative HPLC with a gradient of 0.025% TFA in water and methanol. Upon drying in vacuo, the title product (50.3 mg, 0.15 mmol, 48%) was obtained as a white, foamy solid. 1H NMR (DMSO-$d_6$) δ 11.3 (s, 1H), 9.9 (s, 1H), 8.69 (m, 2H), 7.80-7.53 (m, 3H), 4.23 (s, 2H), 3.34 (s, 8H), 2.67 (s, 2H), 2.49 (m, 12H), 1.93 (m, 3H), 1.76-1.44 (m, 14H). MS (m/z) calc'd for $C_{19}H_{25}FN_2O_2$ [M+H]$^+$ 332.19; found, 332.7.

Example 17. 4-(((((3r,5r,7r)-adamantan-1-yl)methyl) amino)methyl)-N-hydroxybenzamide

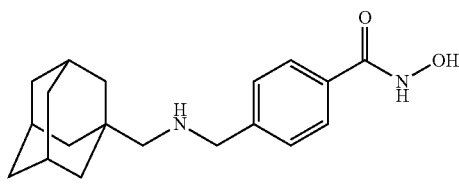 [SMILES: O=C(NO)c1ccc(CNCC23CC4CC(CC(C4)C2)C3)cc1]

To a solution of Intermediate 8 (92 mg, 0.29 mmol, 1 eq) in 2 mL 1:1 THF/MeOH was added 0.50 mL hydroxylanine (50% aq, 0.25 g, 3.6 mmol, 12 eq) and aqueous NaOH (5.0 M, 0.10 mL, 0.50 mmol, 2 eq). The reaction mixture was stirred for 5 h, then 100 µL 2.5N HCl was added. The product was purified by preparative HPLC with a gradient of 0.025% TFA in water and methanol. Upon drying in vacuo the title product (49.7 mg, 0.16 mmol, 55%) was obtained as a white solid. $^1$H NMR (DMSO-d6) δ 11.3 (s, 1H), 8.8 (m, 2H), 7.79 (d, 2H), 7.58 (d, 2H), 4.19 (s, 2H), 3.49 (s, 5H), 2.55 (m, 7H), 1.91 (m, 4H), 1.78-1.39 (m, 17H). MS (m/z) calc'd for $C_{19}H_{26}N_2O_2$ [M+H]$^+$ 314.2; found, 314.7.

Example 18. 4-(((((3s,5s,7s)-adamantan-1-yl)amino) methyl)-N-hydroxybenzamide

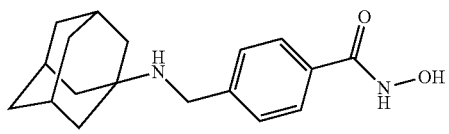 [SMILES: O=C(NO)c1ccc(CNC23CC4CC(CC(C4)C2)C3)cc1]

To a solution of Intermediate 9 (34 mg, 0.11 mmol, 1 eq) in 2 mL 1:1 THF/MeOH at 0° C. was added 0.50 mL hydroxylamine (50% aq, 0.25 g, 3.6 mmol, 32 eq) and aqueous NaOH (5.0 M, 0.10 mL, 0.50 mmol, 5 eq). The reaction mixture was stirred for 2 h. The product was purified by preparative HPLC with a gradient of 0.025% TFA in water and methanol. Upon drying in vacuo, the title product (32 mg, 0.1 mmol, 95%) was obtained as a white, foamy solid. 11H NMR (DMSO-d6) δ 11.3 (s, 1H), 9.0 (s, 1H), 8.8 (d, 2H), 7.8 (d, 2H), 4.1 (s, 2H), 3.34 (s, 8H), 2.49 (m, 8H), 2.49 (m, 10H), 2.16 (m, 3H), 2.04-1.84 (m, 6H), 1.76-1.51 (m, 6H). MS (m/z) calc'd for $C_{18}H_{24}N_2O_2$ [M+H]$^+$, 300.40; found, 300.7.

Example 19. 4-(((1-(adamantan-1-yl)propan-2-yl) amino)methyl)-N-hydroxybenzamide

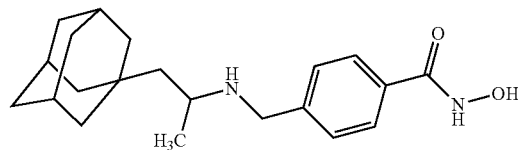 [SMILES: CC(CC12CC3CC(CC(C3)C1)C2)NCc1ccc(C(=O)NO)cc1]

To a solution of Intermediate 10 (191 mg, 0.56 mmol, 6.4 eq) in 2 mL 1:1 THF/MeOH at 0° C. was added 0.50 mL hydroxylamine (50% aq, 0.25 g, 3.6 mmol, 6.4 eq) and aqueous NaOH (5.0 M, 0.10 mL, 0.50 mmol, 1 eq). The reaction mixture was stirred for 3 h, then 80 µL 6N HCl was added. The product was purified by preparative HPLC with a gradient of 0.025% TFA in water and methanol. Upon drying in vacuo product (103 mg, 0.30 mmol, 53%) was obtained as a white solid. 1H NMR (DMSO-$d_6$) δ 11.3 (s, 1H), 8.8 (d, 2H), 7.8 (d, 2H), 7.5 (d, 2H), 4.1 (s, 2H), 3.39 (s, 6H), 2.49 (m, 7H), 1.92 (m, 3H), 1.76-1.39 (m, 15H), 1.39-1.21 (m, 5H). MS (m/z) calc'd for $C_{21}H_{30}N_2O_2$ [M+H]$^+$ 342.23; found, 342.7.

Example 20. 4-(((1-(adamantan-1-yl)propan-2-yl) amino)methyl)-N-hydroxybenzamide

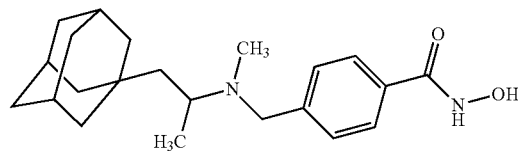

Step 1. methyl 4-(((1-((3r,5r,7r)-adamantan-1-yl) propan-2-yl)(methyl)amino)methyl)benzoate

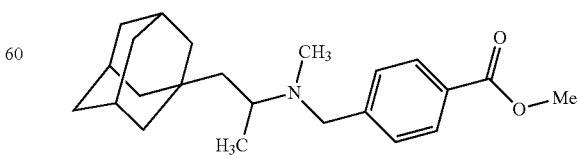

A solution of Intermediate 10 (97 mg, 0.28 mmol) in 3 mL 0.5 mL formalin and a drop of acetic acid were stirred for 2 h, then 184 mg sodium borohydride was added portionwise and the reaction was stirred 2 h. The mixture was concentrated in vacuo, partitioned between ethyl acetate and water, the aqueous layer extracted two more times with ethyl acetate and the combined organic phases were dried over sodium sulfate. The solvent was removed under reduced pressure and the product was purified by column chromatography. Methyl 4-(((1-((3r,5r,7r)-adamantan-1-yl)propan-2-yl)(methyl)amino)methyl)benzoate (33 mg, 0.09 mmol, 33%) was obtained as a clear oil that solidified upon standing. MS (m/z) calc'd for $C_{23}H_{22}NO_2$ [M+H]$^+$, 355.25; found, 355.8.

Step 2. 4-(((1-(adamantan-1-yl)propan-2-yl)amino)methyl)-N-hydroxybenzamide

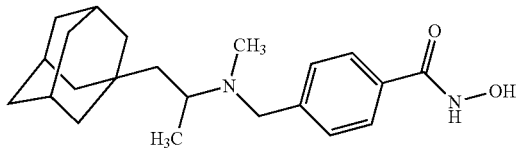 [SMILES: CC(CC12CC3CC(CC(C3)C1)C2)N(C)Cc1ccc(C(=O)NO)cc1]

To a solution of methyl 4-(((1-((3r,5r,7r)-adamantan-1-yl)propan-2-yl)(methyl)amino)methyl)benzoate (33 mg, 0.09 mmol, 1 eq) in 2 mL 1:1 THF/MeOH was added 0.50 mL hydroxylamine (50% aq, 0.25 g, 3.6 mmol, 37 eq) and aqueous NaOH (5.0 M, 0.10 mL, 0.50 mmol, 5 eq). The reaction mixture was stirred for 2 h RT, then 80 μL 6N HCl was added. The product was purified by preparative HPLC with a gradient of 0.025% TFA in water and methanol. Upon drying in vacuo, the title product (31 mg, 0.087 mmol, 90%) was obtained as a white solid. 1H NMR (DMSO-d6) δ 11.3 (s, 1H), 7.8 (d, 2H), 7.6 (d, 2H), 4.4 (m, 1H), 4.2 (m, 1H), 3.6 (m, 11H), 2.70-2.39 (m, 16H), 2.05-1.82 (m, 4H), 1.82-1.20 (m, 24H). MS (m/z) calc'd for $C_{22}H_{32}N_2O_2$ [M+H]$^+$ 356.51; found, 356.7.

Example 21. 4-(((1-((3r,5r,7r)-adamantan-1-yl)propyl)amino)methyl)-N-hydroxybenzamide

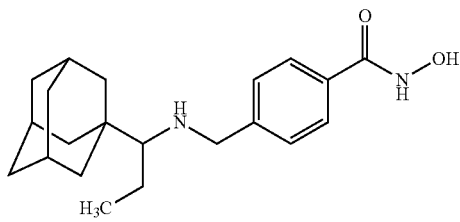

To a solution of Intermediate 11 (89.7 mg, 0.26 mmol, 1 eq) in 2 mL 1:1 THF/MeOH at 0° C. was added 0.50 mL hydroxylamine (50% aq, 0.25 g, 3.6 mmol, 13.8 eq) and aqueous NaOH (5.0 M, 0.10 mL, 0.50 mmol, 1.92 eq). The reaction mixture was stirred for 5 h, then 80 μL 6N HCl was added. The product was purified by preparative HPLC with a gradient of 0.025% TFA in water and methanol. Upon drying in vacuo, the title product (84 mg, 0.24 mmol, 93%) was obtained as a white, foamy solid. 1H NMR (DMSO-d6) δ 11.3 (s, 1H), 9.1 (s, 1H), 8.9 (s, 1H), 7.8 (d, 2H), 7.6 (d, 2H), 4.4 (m, 2H), 3.3 (m, 7H), 2.5 (s, 9H), 2.2 (m, 1H), 2.02-1.87 (m, 3H), 1.87-1.72 (m, 1H), 1.72-1.46 (m, 12H), 1.45-1.34 (m, 3H), 1.03-0.80 (m, 3H). MS (m/z) calc'd for $C_{22}H_{31}N_2O_2$ [M+H]$^+$ 342.23; found, 342.9.

Example 22. 4-(((1-((3r,5r,7r)-adamantan-1-yl)propyl)(methyl)amino)methyl)-N-hydroxybenzamide

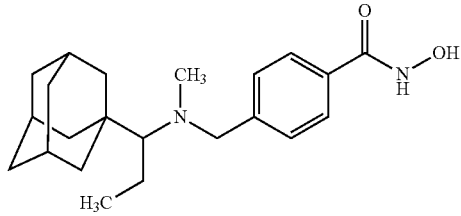 [SMILES: CCC(N(C)Cc1ccc(C(=O)NO)cc1)C12CC3CC(CC(C3)C1)C2]

Step 1. methyl 4-(((1-((3r,5r,7r)-adamantan-1-yl)propyl)(methyl)amino)methyl)benzoate

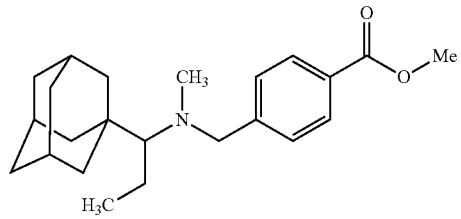 [SMILES: CCC(N(C)Cc1ccc(C(=O)OC)cc1)C12CC3CC(CC(C3)C1)C2]

To a solution of Intermediate 11 (95 mg, 0.29 mmol) in 3 mL, 0.5 mL formalin and a drop of acetic acid were stirred for 2 h, then 215 mg sodium borohydride was added portionwise and the reaction was stirred 2 h. The mixture was concentrated in vacuo, partitioned between ethyl acetate and water, the aqueous layer extracted two more times with ethyl acetate and the combined organic phases were dried over sodium sulfate. The solvent was removed under reduced pressure and the product was purified by column chromatography. Methyl 4-(((1-((3r,5r,7r)-adamantan-1-yl)propyl)(methyl)amino)methyl)benzoate (79.7 mg, 0.23 mmol, 79%) was obtained as a clear oil that solidified upon standing. MS (m/z) calc'd for $C_{23}H_{33}NO_2$ [M+H]$^+$ 355.2; found, 355.7.

Step 2. 4-(((1-((3r,5r,7r)-adamantan-1-yl)propyl)(methyl)amino)methyl)-N-hydroxybenzamide

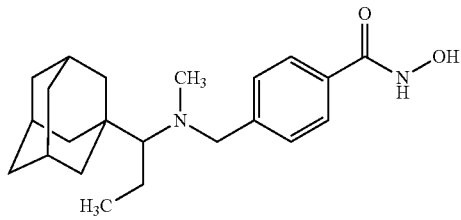 [SMILES: CCC(N(C)Cc1ccc(C(=O)NO)cc1)C12CC3CC(CC(C3)C1)C2]

To a solution of methyl 4-(((1-((3r,5r,7r)-adamantan-1-yl)propyl)(methyl)amino)methyl)benzoate (79 mg, 0.22 mmol, 1 eq.) in 2 mL 1:1 THF/MeOH at 0° C. was added 0.50 mL hydroxylamine (50% aq, 0.25 g, 3.6 mmol, 16 eq) and aqueous NaOH (5.0 M, 0.10 mL, 0.50 mmol, 2 eq). The reaction mixture was stirred for 3.5 h RT, then 80 µL 6N HCl was added. The product was purified by preparative HPLC with a gradient of 0.025% TFA in water and methanol. Upon drying in vacuo product (45 mg, 0.13 mmol, 59%) was obtained as a white solid. 1H NMR (DMF-d6) δ 8.9 (s, 1H), 8.14-7.73 (m, 7H), 4.84-4.47 (m, 2H), 3.23-3.00 (m, 3H), 3.00-2.66 (m, 8H), 2.2 (m, 1H), 2.07-1.33 (m, 27H), 1.31-0.91 (m, 4H). MS (m/z) calc'd for $C_{22}H_{32}N_2O_2$ [M+H]$^+$ 356.25; found, 356.7.

Example 23. 4-((((6,6-dimethylbicyclo[3.1.1]heptan-2-yl)methyl)amino)methyl)-N-hydroxybenzamide

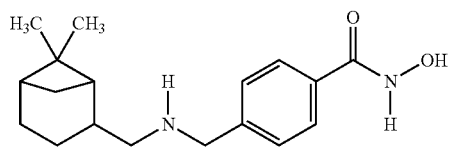 [SMILES: CC1(C)C2CCC(CNCc3ccc(C(=O)NO)cc3)C1C2]

To a solution of Intermediate 12 (73 mg, 0.24 mmol, 1 eq) in 2 mL 1:1 THF/MeOH was added 0.50 mL hydroxylamine (50% aq, 0.25 g, 3.6 mmol, 15 eq) and aqueous NaOH (5.0 M, 0.10 mL, 0.50 mmol, 2 eq). The reaction mixture was stirred for 3 h RT, then the product was purified by preparative HPLC with a gradient of 0.025% TFA in water and methanol. Upon drying in vacuo, the title product (29 mg, 0.096 mmol, 40%) was obtained as a white solid. 1H NMR (DMSO-d6) δ 11.3 (s, 1H), 9.1 (s, 1H), 9.0 (s, 2H), 7.78 (d, 2H), 7.54 (d, 2H), 4.2 (m, 2H), 3.34 (s, 2H), 2.91 (s, 2H), 2.58-2.23 (m, 7H), 2.03-1.71 (m, 5H), 1.73-1.38 (m, 4H), 1.59-1.37 (m, 1H), 1.23-1.07 (m, 3H), 0.99-0.72 (m, 4H). MS (m/z) calc'd for $C_{18}H_{26}N_2O_2$ [M+H]$^+$ 302.2; found, 302.7.

Example 24. 4-(((((6,6-dimethylbicyclo[3.1.1]heptan-2-yl)methyl)(pentyl)amino)methyl)-N-hydroxybenzamide

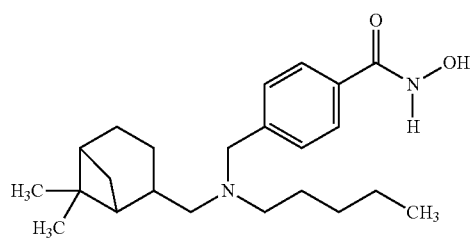 [SMILES: CCCCCN(Cc1ccc(C(=O)NO)cc1)CC1CCC2CC1C2(C)C]

Step 1. methyl 4-(((((6,6-dimethylbicyclo[3.1.1]heptan-2-yl)methyl)(pentyl)amino)methyl)benzoate

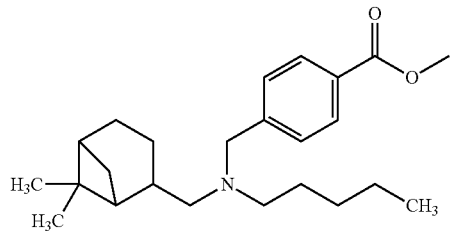

A solution of Intermediate 12 (56 mg, 0.19 mmol) in 0.2 ml DMSO, 23 µL 1-bromopentane and 44 µL N,N-diisopropylethylamine was added and the mixture was stirred for 12 h at 60° C. The mixture was diluted with water, partitioned between ethyl acetate and water, the aqueous layer extracted two more times with ethyl acetate and the combined organic phases were then extracted with three time with water. Next, the organic phase was dried over sodium sulfate. The solvent was removed under reduced pressure and the product was purified by column chromatography. Methyl 4-(((((6,6-dimethylbicyclo[3.1.1]heptan-2-yl)methyl)(pentyl)amino)methyl)benzoate (25.8 mg, 0.07 mmol, 36%) was obtained as a yellowish oil. MS (m/z) calc'd for $C_{24}H_{37}NO_2$ [M+H]$^+$ 371.3; found, 313.7.

Step 2. 4-(((((6,6-dimethylbicyclo[3.1.1]heptan-2-yl)methyl)(pentyl)amino)methyl)-N-hydroxybenzamide

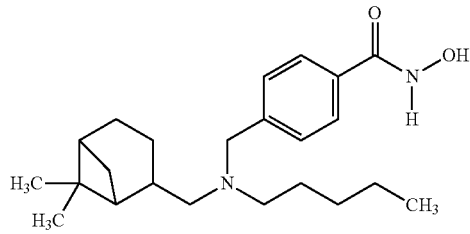 [SMILES: CCCCCN(Cc1ccc(C(=O)NO)cc1)CC1CCC2CC1C2(C)C]

To a solution of methyl 4-(((((6,6-dimethylbicyclo[3.1.1]heptan-2-yl)methyl)(pentyl)amino)methyl)benzoate (~25 mg, 0.07 mmol, 1 eq) in 2 mL 1:1 THF/MeOH at was added 0.50 mL hydroxylamine (50% aq, 0.25 g, 3.6 mmol, 51 eq) and aqueous NaOH (5.0 M, 0.10 mL, 0.50 mmol, 7 eq). The reaction mixture was stirred for 3.5 h RT, then concentrated in vacuo, partitioned between dichloromethane and water, the aqueous layer extracted two more times with dichloromethane. The organic phase was dried over sodium sulfate. The solvent was removed under reduced pressure and the product was purified by preparative HPLC with a gradient of 0.025% TFA in water and methanol. Upon drying in vacuo, the title product (9 mg, 0.024 mmol, 34%) was obtained as a yellowish oil. 1H NMR (DMSO-d6) δ 7.83-7.33 (m, 1H), 3.71-3.20 (m, 18H), 2.85-2.23 (m, 72H), 1.37-1.07 (m, 4H), 1.07-0.73 (m, 3H), 0.73-0.44 (m, 1H). MS (m/z) calc'd for $C_{23}H_{36}N_2O_2$ [M+H]$^+$ 372.3; found, 372.8.

Example 25. 4-(((cyclohexylmethyl)amino)methyl)-N-hydroxybenzamide

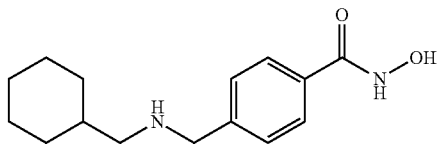 [SMILES: O=C(NO)c1ccc(CNCC2CCCCC2)cc1]

To a solution of Intermediate 13 (196 mg, 0.75 mmol 1 eq) in 2 mL 1:1 THF/MeOH at was added 0.50 mL hydroxylamine (50% aq, 0.25 g, 3.6 mmol, 4.8 eq) and aqueous NaOH (5.0 M, 0.10 mL, 0.50 mmol, 0.67 eq). The reaction mixture was stirred for 4 h RT, then the product was purified by preparative HPLC with a gradient of 0.025% TFA in water and methanol. Upon drying in vacuo, the title product (108 mg, 0.41 mmol, 55%) was obtained as a white, little brownish solid. 1H NMR (DMSO-d6) δ 11.3 (s, 1H), 8.9 (m, 2H), 7.77 (d, 2H), 7.55 (d, 2H), 4.18 (s, 2H), 3.42 (s, 3H), 2.77 (m, 2H), 2.50 (m, 4H), 1.83-1.49 (m, 6H), 1.31-1.02 (m, 3H), 1.02-0.79 (m, 2H). MS (m/z) calc'd for $C_{15}H_{22}N_2O_2$ [M+H]$^+$ 262.17; found, 262.7.

Figures 8A, 8B:
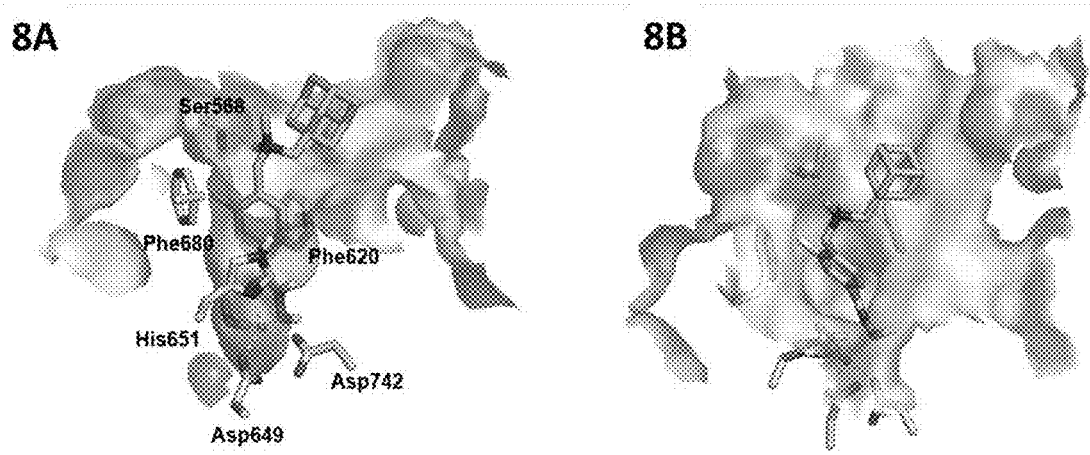
FIGS. 8A-8B the compound of Example 2 docked into the CD2 hHDAC6 complex.

Example 26. Docking Studies 4-(((((3s)-Adamantan-1-yl)methyl)(methyl)amino)methyl)-3-fluoro-N-hydroxybenzamide was docked into the CD2 hHDAC6 complex described in the methods section. FIG. 8A shows the complex hydrogen bond network between the catalytic zinc (purple sphere); the protein and the ligand are shown as yellow dashed lines. The fluorine substituent on the linker phenyl ring of 4-(((((3s)-adamantan-1-yl)methyl)(methyl)amino)methyl)-3-fluoro-N-hydroxybenzamide was modelled to vector in a hollow divot/cleft in the hHDAC6 10 Å channel leading to the protein surface, as shown in FIG. 8B.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising a radiolabeled compound of the formula

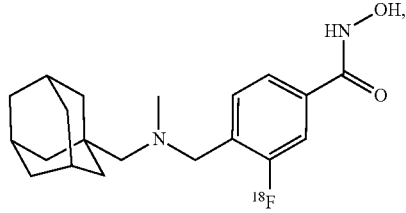 [SMILES: CN(Cc1ccc(C(=O)NO)cc1[18F])CC12CC3CC(CC(C3)C1)C2]

or a pharmaceutically acceptable salt thereof and one or more pharmaceutically acceptable carriers.

2. The imaging composition of claim 1, further comprising a mixture of the radiolabeled compound and a compound of the formula

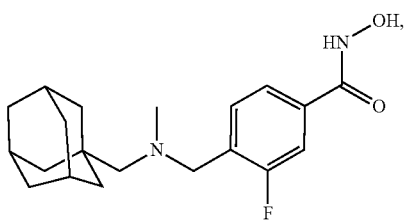 [SMILES: CN(Cc1ccc(C(=O)NO)cc1F)CC12CC3CC(CC(C3)C1)C2]

or a pharmaceutically acceptable salt thereof.

3. The composition of claim 2, wherein the composition is a formulated as a liquid.

4. The composition of claim 1, wherein the composition is formulated as a sterile injectable solution.

5. The composition of claim 1, wherein the composition is formulated for intravenous administration.

6. The composition of claim 1, wherein the radiolabeled compound is obtained by a process comprising a step of contacting a phenol precursor compound with an air-stable Ruthenium-complex.

7. The composition of claim 6, wherein a. the phenol precursor compound is a compound of formula

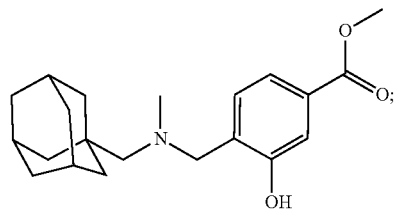 [SMILES: COC(=O)c1ccc(CN(C)CC23CC4CC(CC(C4)C2)C3)c(O)c1]

and b. the air-stable Ruthenium-complex is Ru(cp)(cod)Cl.

8. The composition of claim 7, wherein the reaction of the phenol precursor and the air-stable ruthenium complex forms an η$^6$-ruthenium complex of the formula:

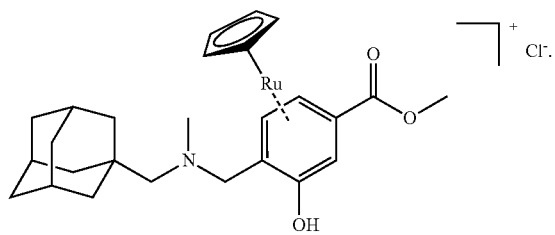

9. The composition of claim 8, wherein the radiolabeled compound is obtained by a process further comprising the step of using the η$^6$-ruthenium complex as an eluent to elute $^{18}$F from an anion exchange column or cartridge to obtain an $^{18}$F phenol precursor of the formula

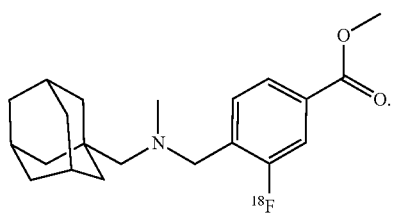 [SMILES: COC(=O)c1ccc(CN(C)CC23CC4CC(CC(C4)C2)C3)c([18F])c1]

10. The composition of claim 9, wherein the radiolabeled compound is obtained by a process further comprising the subsequent transacylation of the $^{18}$F phenol precursor to obtain the radiolabeled compound of the formula

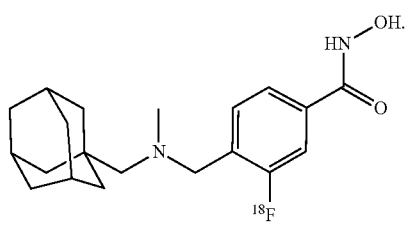

11. The composition of claim 1, wherein the radiolabeled compound is obtained by a process comprising the steps of contacting a precursor compound of the formula

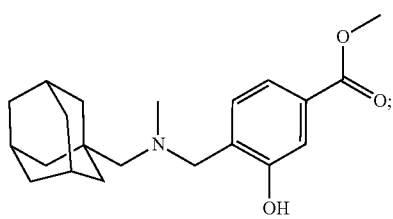 [SMILES: COC(=O)c1ccc(CN(C)CC23CC4CC(CC(C4)C2)C3)c(O)c1]

or a pharmaceutically salt thereof,
with an air-stable Ruthenium-complex, transacylation and elution of $^{18}$F from an anion exchange column or cartridge to obtain the radiolabeled compound of claim 1.

12. The composition of claim 1, wherein the radiolabeled compound is obtained by a process comprising the step of contacting a precursor compound of the formula

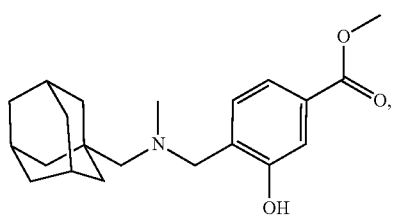 [SMILES: COC(=O)c1ccc(CN(C)CC23CC4CC(CC(C4)C2)C3)c(O)c1]

or a pharmaceutically salt thereof,
with Ru(cp)(cod)Cl, N,N-bis-(2,6-diisopropyl)phenyl-2-chloroimidazolium chloride and $^{18}$F radioisotope, in one or more steps under conditions effective to form the radiolabeled compound.

13. The composition of claim 5, the radiolabeled compound is obtained by a process comprising the steps of a. contacting a phenol precursor compound of formula

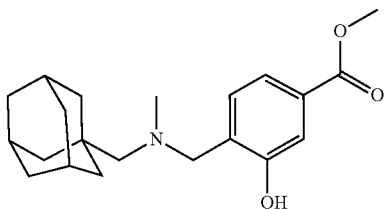 [SMILES: COC(=O)c1ccc(CN(C)CC23CC4CC(CC(C4)C2)C3)c(O)c1]

with Ru(cp)(cod)Cl;

b. using the compound resulting from step (a) in an eluent to elute $^{18}$F from an anion exchange column or cartridge; and c. using the compound resulting from step (b) in a transacylation reaction to obtain the radiolabeled compound.

14. The composition of claim 1, wherein the radiolabeled compound is obtained by a process comprising the steps of a. contacting a precursor compound of the formula

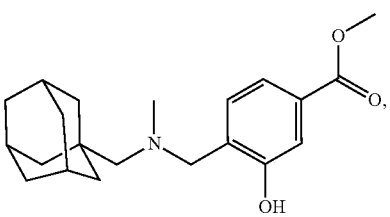 [SMILES: COC(=O)c1ccc(CN(C)CC23CC4CC(CC(C4)C2)C3)c(O)c1]

or a salt thereof,
with Ru(cp)(cod)Cl;

b. contacting the product of step (a) with N,N-bis-(2,6-diisopropyl)phenyl-2-chloroimidazolium chloride and $^{18}$F radioisotope; and c.1 transacetylating the product of step (b) to obtain the radiolabeled compound of claim 1.

15. A method comprising the steps of a. administering the composition of claim 1 a subject; and b. obtaining an image of the brain of the subject with an imaging technique to detect the radiolabeled imaging composition in the brain of the subject.

16. The method of claim 15, wherein the composition of claim 1 is detected using positron emission tomography (PET) imaging technique.

17. The composition of claim 1, wherein the composition provides PET-detectable level of

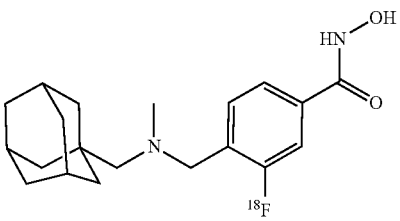 [SMILES: CN(Cc1ccc(C(=O)NO)cc1[18F])CC12CC3CC(CC(C3)C1)C2]

in the brain of a subject.

* * * * *

UNITED STATES PATENT AND TRADEMARK OFFICE
CERTIFICATE OF CORRECTION

PATENT NO. : 11,890,356 B2
APPLICATION NO. : 17/455170
DATED : February 6, 2024
INVENTOR(S) : Jacob Hooker et al.

It is certified that error appears in the above-identified patent and that said Letters Patent is hereby corrected as shown below:

In the Claims

Column 70, Line 1, Claim 2:
After "The" delete "imaging"

Column 70, Line 19, Claim 3:
After "is" delete "a"

Column 71, Lines 31-39 (approx.), Claim 11:
In the Formula, delete "O;" and insert -- O, --

Column 72, Line 40 (approx.), Claim 14:
After "c." delete "1"

Column 72, Line 43 (approx.), Claim 15:
After "claim 1" insert -- to --

Signed and Sealed this
Twenty-eighth Day of May, 2024

*Katherine Kelly Vidal*

Katherine Kelly Vidal
*Director of the United States Patent and Trademark Office*